(12) United States Patent
Lupold et al.

(10) Patent No.: US 9,029,340 B2
(45) Date of Patent: May 12, 2015

(54) RADIATION SENSITIZATION AGENTS FOR PROSTATE CANCER

(75) Inventors: Shawn Edward Lupold, Ellicott City, MD (US); Theodore L. DeWeese, Baltimore, MD (US); Xiaohua Ni, Baltimore, MD (US); Yonggang Zhang, Nottingham, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/811,442

(22) PCT Filed: Jul. 22, 2011

(86) PCT No.: PCT/US2011/044997
§ 371 (c)(1),
(2), (4) Date: Jan. 22, 2013

(87) PCT Pub. No.: WO2012/012710
PCT Pub. Date: Jan. 26, 2012

(65) Prior Publication Data
US 2013/0123566 A1 May 16, 2013

Related U.S. Application Data

(60) Provisional application No. 61/366,734, filed on Jul. 22, 2010.

(51) Int. Cl.
*A61K 48/00* (2006.01)
*C07H 21/02* (2006.01)
*C07H 21/04* (2006.01)
*A61K 38/00* (2006.01)
*A61P 35/00* (2006.01)

(52) U.S. Cl.
CPC .................................. *A61K 48/005* (2013.01)

(58) Field of Classification Search
USPC ............................................ 514/44; 536/24.5
See application file for complete search history.

(56) References Cited

U.S. PATENT DOCUMENTS 7,314,855 B2    1/2008   Ronai
2008/0262286 A1 10/2008  Hallahan et al.

OTHER PUBLICATIONS

Collis et al. (Cancer Res. 2003; 63(7):1550-1554).*
DeWeese et al., "PSMA Aptamer-Targeted siRNAs Selectively Enhance Prostate Cancer Radiation Sensitivity", ASTRO 2009 Annual Meeting (Radiation Oncology in 2020), (Nov. 4, 2009).
Shaw et al., "Boranophosphate siRNA-aptamer chimeras for tumor-specific downregulation of cancer receptors and modulators", Nucleic Acids Symposium Series, No. 52, pp. 655-656 (2008).

(Continued)

*Primary Examiner* — Terra Cotta Gibbs
(74) *Attorney, Agent, or Firm* — Mintz Levin Cohn Ferris Glovsky and Popeo, P.C.; Peter F. Corless, Esq.

(57) ABSTRACT

Compositions and methods are provided for sensitizing neoplastic cells to radiotherapy. The invention provides aptamer-inhibitory nucleic acid chimeras that selectively inliibit the expression of radiosensitizing genes in neoplastic cells expressing a cell surface molecule that binds the aptamer.

10 Claims, 21 Drawing Sheets

(56) References Cited

OTHER PUBLICATIONS

Dassie et al., "Systemic administration of optimized aptamer-siRNA chimeras promotes regression of PSMA-expressing tumors", Nature Biotechnology, vol. 27, No. 9, pp. 839-849 (2009).

Winden et al., "Early diagnostic protein biomarkers for breast cancer: how far have we come?", Breast Cancer Res. Treat., vol. 134, pp. 1-12 (2012).

Keefe et al., "SELEX with modified nucleotides," Current Opinion in Chemical Biology (2008), 12:448-456.

* cited by examiner

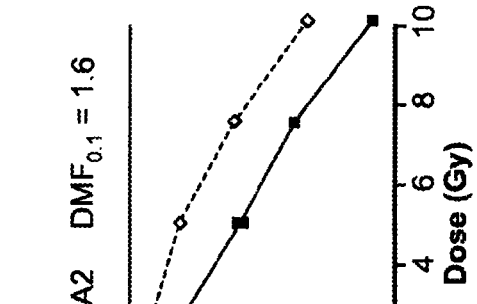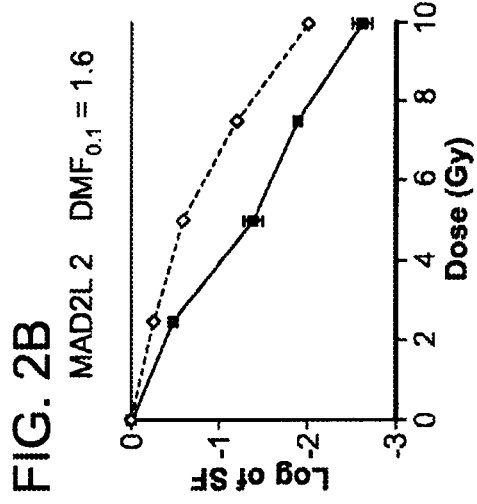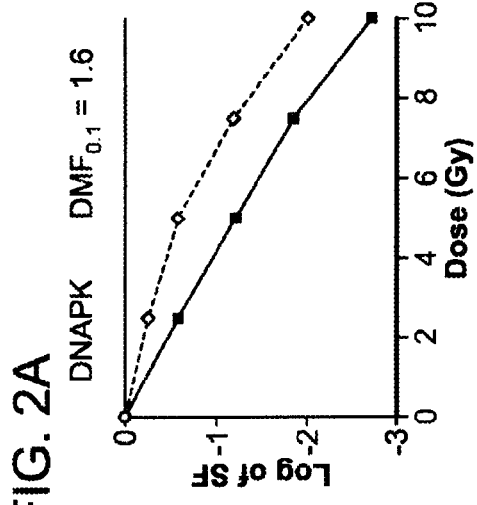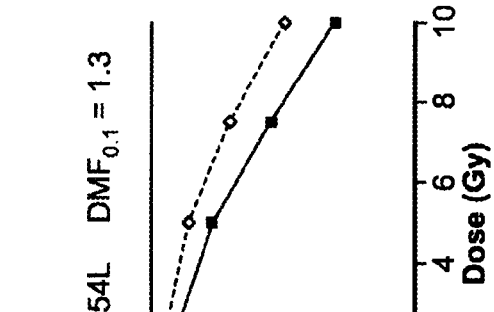

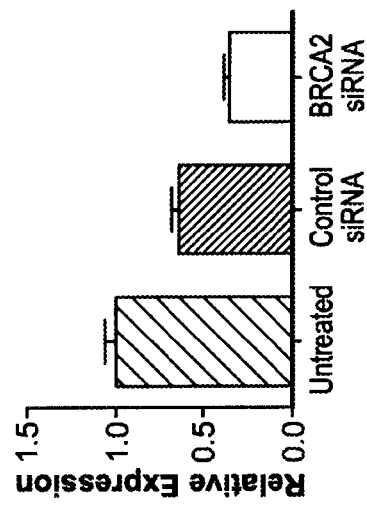
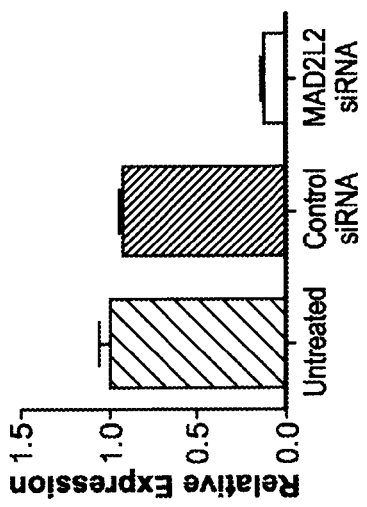
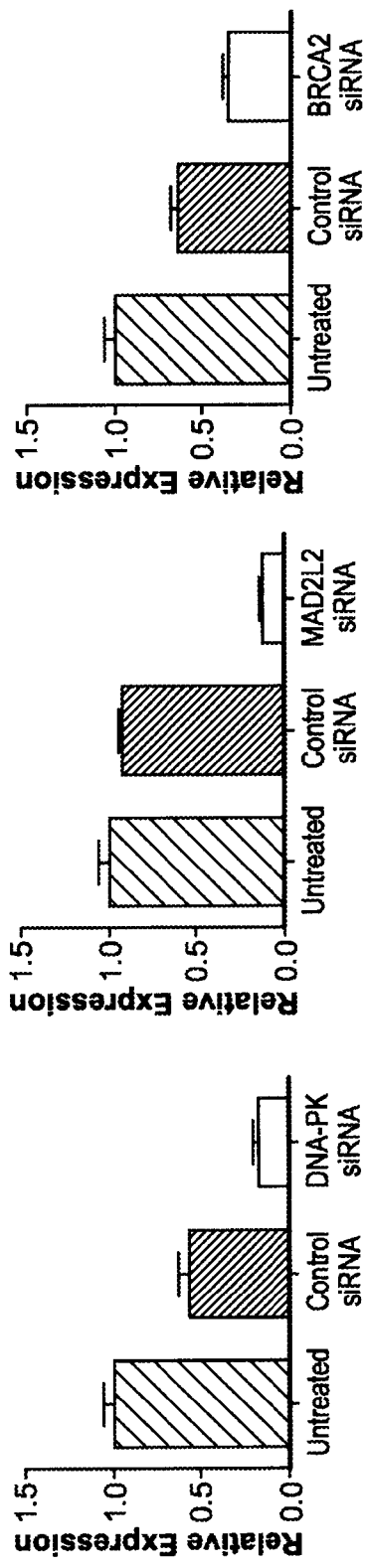
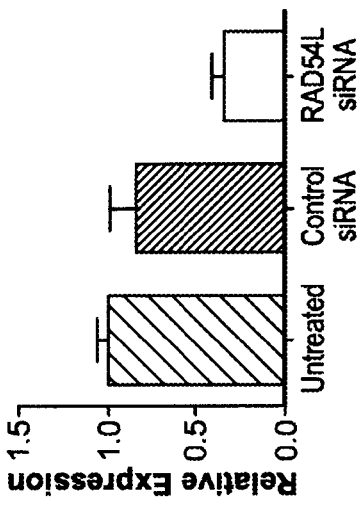
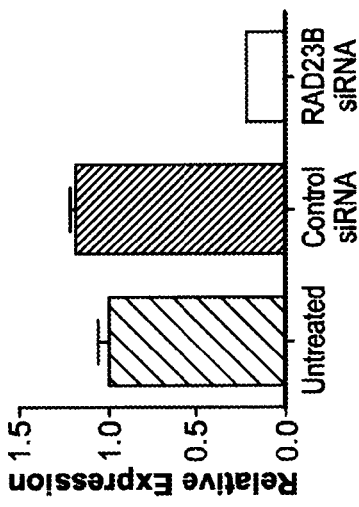
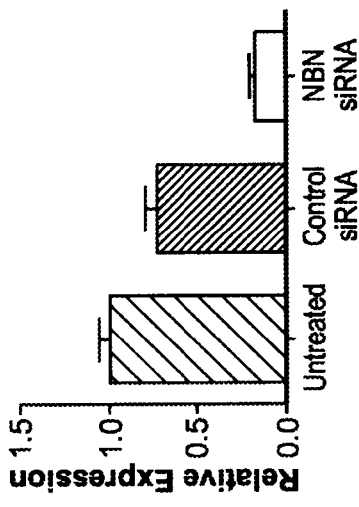

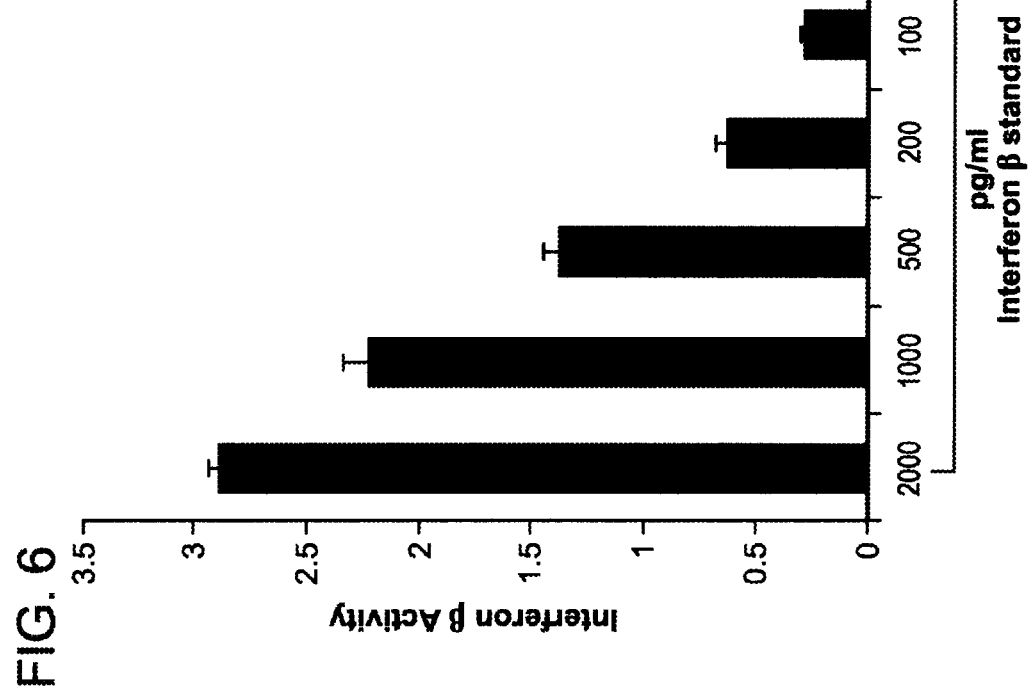

| Name | Sequence |
|---|---|
| A10-3 | GGGAGGACGAUGCGGAUCAGCCAUGUUACGUCACUCCUGUCAAUCCUCAUCGGC |
| DNAPK antisence (AS-siRNA) | UAAACUGGGCGAGUUAGCCGAAUU |
| DNAPK sence (S-siRNA) | UUCGGCUAACUCGCCAGUUUAGCCGAUGAGGAUU |

SEQUENCE LISTING

<160> NUMBER OF SEQ ID NOS: 65

<210> SEQ ID NO 1
<211> LENGTH: 4360
<212> TYPE: DNA
<213> ORGANISM: Homo sapiens

<400> SEQUENCE: 1
agccgatggg ggcggggaaa agtccggctg ggccgggaca aaagccggat cccgggaagc    60

```
taccggctgc tggggtgctc cggattttgc ggggttcgtc gggcctgtgg aagaagcgcc      120
gcgcacggac ttcggcagag gtagagcagg tctctctgca gccatgtcgg ccaaggcaat      180
ttcagagcag acgggcaaag aactcctttta caagttcatc tgtaccacct cagccatcca    240
gaatcggttc aagtatgctc gggtcactcc tgacacagac tgggcccgct tgctgcagga     300
ccacccctgg ctgctcagcc agaacttggt agtcaagcca gaccagctga tcaaacgtcg     360
tggaaaactt ggtctcgttg ggtcaacct cactctggat ggggtcaagt cctggctgaa      420
gccacggctg gacaggaag ccacagttgg caaggccaca ggcttcctca gaactttct       480 gatcgagccc ttcgtccccc acagtcaggc tgaggagttc tatgtctgca tctatgccac     540
ccgagaaggg gactacgtcc tgttccacca cgagggggggt gtggacgtgg gtgatgtgga    600
cgccaaggcc cagaagctgc ttgttggcgt ggatgagaaa ctgaatcctg aggacatcaa    660
aaaacacctg ttggtccacg cccctgaaga caagaaagaa attctggcca gttttatctc     720
cggcctcttc aatttctacg aggacttgta cttcacctac ctcgagatca atccccttgt     780
agtgaccaaa gatggagtct atgtccttga cttggcggcc aaggtggacg ccactgccga    840
ctacatctgc aaagtgaagt gggtgacat cgagttccct ccccccttcg gcgggaggc      900 atatccagag aagcctaca ttgcagacct cgatgccaaa agtggggcaa gcctgaagct     960
gaccttgctg aaccccaaag ggaggatctg gaccatggtg gccggggtg gcgcctctgt    1020 cgtgtacagc gataccatct gtgatctagg gggtgtcaac gagctggcaa actatgggga    1080
gtactcaggc gcccccagcg agcagcagac ctatgactat gccaagacta tcctctccct    1140
catgacccga gagaagcacc cagatggcaa gatcctcatc attggaggca gcatcgcaaa    1200
cttcaccaac gtggctgcca cgttcaaggg catcgtgaga gcaattcgag attaccaggg    1260 cccccctgaag gagcacgaag tcacaatctt tgtccgaaga ggtggcccca actatcagga   1320
gggcttacgg gtgatgggag aagtcgggaa gaccactggg atccccatcc atgtctttgg    1380
cacagagact cacatgacgg ccattgtggg catggccctg gccaccggc ccatccccaa     1440 ccagccaccc acagcggccc acactgcaaa cttcctcctc aacgccagcg ggagcacatc    1500
gacgccagcc cccagcagga cagcatcttt ttctgagtcc agggccgatg aggtggcgcc    1560
tgcaaagaag gccaagcctg ccatgccaca agattcagtc ccaagtccaa gatccctgca    1620
aggaaagagc accaccctct tcagccgcca caccaaggcc attgtgtggg gcatgcagac    1680
ccgggccgtg caaggcatgc tggactttga ctatgtctgc tcccgagacg agccctcagt    1740
ggctgccatg gtctacccctt tcactgggga ccacaagcag aagttttact gggggcacaa    1800
agagatcctg atccctgtct tcaagaacat ggctgatgcc atgaggaagc atccggaggt    1860
agatgtgctc atcaactttg cctctctccg ctctgcctat gacagcacca tggagaccat    1920
gaactatgcc cagatccgga ccatcgccat catagctgaa gcatccctg aggccctcac     1980 gagaaagctg atcaagaagg cggaccagaa gggagtgacc atcatcggac tgccactgt      2040 tggaggcatc aagcctgggt gctttaagat tgcaacaca ggtgggatgc tggacaacat     2100
cctggcctcc aaactgtacc gccaggcag cgtggcctat gtctcacgtt ccggaggcat     2160
gtccaacgag ctcaacaata tcatctctcg gaccacggat ggcgtctatg agggcgtggc    2220
cattggtggg gacaggtacc cgggctccac attcatggat catgtgttac gctatcagga    2280
cactccagga gtcaaaatga ttgtggttct tggagagatt gggggcactg aggaatataa    2340
gatttgccgg ggcatcaagg agggccgcct cactaagccc atcgtctgct ggtgcatcgg    2400
gacgtgtgcc accatgttct cctctgaggt ccagtttggc catgctggag cttgtgccaa    2460
```

```
ccaggcttct gaaactgcag tagccaagaa ccaggctttg aaggaagcag gagtgtttgt    2520
gccccggagc tttgatgagc ttggagagat catccagtct gtatacgaag atctcgtggc    2580
caatggagtc attgtacctg cccaggaggt gccgccccca accgtgccca tggactactc    2640
ctgggccagg gagcttggtt tgatccgcaa acctgcctcg ttcatgacca gcatctgcga    2700
tgagcgagga caggagctca tctacgcggg catgcccatc actgaggtct tcaaggaaga    2760
gatgggcatt ggcggggtcc tcggcctcct ctggttccag aaaaggttgc ctaagtactc    2820
ttgccagttc attgagatgt gtctgatggt gacagctgat cacgggccag ccgtctctgg    2880
agcccacaac accatcattt gtgcgcgagc tgggaaagac ctggtctcca gcctcacctc    2940
ggggctgctc accatcgggg atcggtttgg gggtgccttg gatgcagcag ccaagatgtt    3000
cagtaaagcc tttgacagtg gcattatccc catggagttt gtgaacaaga tgaagaagga    3060
agggaagctg atcatgggca ttggtcaccg agtgaagtcg ataaacaacc cagacatgcg    3120
agtgcagatc ctcaaagatt acgtcaggca gcacttccct gccactcctc tgctcgatta    3180
tgcactggaa gtagagaaga ttaccacctc gaagaagcca atcttatcc tgaatgtaga    3240 tggtctcatc ggagtcgcat tgtagacat gcttagaaac tgtgggtcct ttactcggga    3300
ggaagctgat gaatatattg acattggagc cctcaatggc atctttgtgc tgggaaggag    3360
tatggggttc attggacact atcttgatca gaagaggctg aagcaggggc tgtatcgtca    3420
tccgtgggat gatatttcat atgttcttcc ggaacacatg agcatgtaac agagccagga    3480
accctactgc agtaaactga agacaagatc tcttccccca agaaaagtg tacagacagc    3540 tggcagtgga gcctgcttta tttagcaggg gcctggaatg taaacagcca ctggggtaca    3600
ggcaccgaag accaacatcc acaggctaac accccttcag tccacacaaa gaagcttcat    3660
atttttttta taagcataga aataaaaacc aagccaatat ttgtgacttt gctctgctac    3720
ctgctgtatt tattatatgg aagcatctaa gtactgtcag gatgggggtct tcctcattgt    3780 agggcgttag gatgttgctt tcttttttcca ttagttaaac attttttttct cctttggagg    3840 aagggaatga acatttatg gcctcaagat actatacatt taaagcaccc caatgtctct    3900 ctttttttt ttttacttcc ctttcttctt ccttatataa catgaagaac attgtattaa    3960
tctgattttt aaagatcttt ttgtatgtta cgtgttaagg gcttgtttgg tatcccactg    4020
aaatgttctg tgttgcagac cagagtctgt ttatgtcagg gggatgggc cattgcatcc    4080 ttagccattg tcacaaaata tgtggagtag taacttaata tgtaaagttg taacatacat    4140
acatttaaaa tggaaatgca gaaagctgtg aaatgtcttg tgtcttatgt tctctgtatt    4200
tatgcagctg atttgtctgt ctgtaactga agtgtgggtc caaggactcc taactacttt    4260
gcatctgtaa tccacaaaga ttctgggcag ctgccacctc agtctcttct ctgtattatc    4320
atagtctggt ttaaataaac tatatagtaa caaaaaaaaa                          4360
```

<210> SEQ ID NO 2
<211> LENGTH: 11386
<212> TYPE: DNA
<213> ORGANISM: Homo sapiens

<400> SEQUENCE: 2

```
gtggcgcgag cttctgaaac taggcggcag aggcggagcc gctgtggcac tgctgcgcct     60
ctgctgcgcc tcgggtgtct tttgcggcgg tgggtcgccg ccgggagaag cgtgagggga    120
cagatttgtg accggcgcgg ttttttgtcag cttactccgg ccaaaaaaga actgcacctc    180
```

-continued

```
tggagcggac ttatttacca agcattggag gaatatcgta ggtaaaaatg cctattggat    240
ccaaagagag gccaacattt tttgaaattt ttaagacacg ctgcaacaaa gcagatttag    300
gaccaataag tcttaattgg tttgaagaac tttcttcaga agctccaccc tataattctg    360
aacctgcaga agaatctgaa cataaaaaca acaattacga accaaaccta tttaaaactc    420
cacaaaggaa accatcttat aatcagctgg cttcaactcc aataatattc aaagagcaag    480
ggctgactct gccgctgtac caatctcctg taaaagaatt agataaattc aaattagact    540
taggaaggaa tgttcccaat agtagacata aaagtcttcg cacagtgaaa actaaaatgg    600
atcaagcaga tgatgtttcc tgtccacttc taaattcttg tcttagtgaa agtcctgttg    660
ttctacaatg tacacatgta acaccacaaa gagataagtc agtggtatgt gggagtttgt    720
ttcatacacc aaagtttgtg aagggtcgtc agacaccaaa acatatttct gaaagtctag    780
gagctgaggt ggatcctgat atgtcttggt caagttcttt agctacacca cccacccttc    840
gttctactgt gctcatagtc agaaatgaag aagcatctga aactgtattt cctcatgata    900
ctactgctaa tgtgaaaagc tatttttcca atcatgatga aagtctgaag aaaaatgata    960
gatttatcgc ttctgtgaca gacagtgaaa acacaaatca aagagaagct gcaagtcatg   1020
gatttggaaa aacatcaggg aattcattta aagtaaatag ctgcaaagac cacattggaa   1080
agtcaatgcc aaatgtccta gaagatgaag tatatgaaac agttgtagat acctctgaag   1140
aagatagttt ttcattatgt ttttctaaat gtagaacaaa aaatctacaa aaagtaagaa   1200
ctagcaagac taggaaaaaa attttccatg aagcaaacgc tgatgaatgt gaaaaatcta   1260
aaaaccaagt gaaagaaaaa tactcatttg tatctgaagt ggaaccaaat gatactgatc   1320
cattagattc aaatgtagca aatcagaagc cctttgagag tggaagtgac aaaatctcca   1380
aggaagttgt accgtctttg gcctgtgaat ggtctcaact aacccttcca ggtctaaatg   1440
gagcccagat ggagaaaata cccctattgc atatttcttc atgtgaccaa atatttcag   1500 aaaaagacct attagacaca gagaacaaaa gaaagaaaga ttttcttact tcagagaatt   1560
ctttgccacg tatttctagc ctaccaaaat cagagaagcc attaaatgag gaaacagtgg   1620
taaataagag agatgaagag cagcatcttg aatctcatac agactgcatt cttgcagtaa   1680
agcaggcaat atctggaact tctccagtgg cttcttcatt tcagggtatc aaaaagtcta   1740
tattcagaat aagagaatca cctaaagaga ctttcaatgc aagttttttca ggtcatatga   1800 ctgatccaaa ctttaaaaaa gaaactgaag cctctgaaag tggactggaa atacatactg   1860
tttgctcaca gaaggaggac tcctatgtc caaatttaat tgataatgga agctggccag   1920
ccaccaccac acagaattct gtagctttga agaatgcagg tttaatatcc actttgaaaa   1980
agaaaacaaa taagtttatt tatgctatac atgatgaaac atcttataaa ggaaaaaaaa   2040
taccgaaaga ccaaaaatca gaactaatta actgttcagc ccagtttgaa gcaaatgctt   2100
ttgaagcacc acttacattt gcaaatgctg attcaggttt attgcattct tctgtgaaaa   2160
gaagctgttc acagaatgat tctgaagaac caactttgtc cttaactagc ctttttggga   2220
caattctgag gaaatgttct agaaatgaaa catgttctaa taatacagta atctctcagg   2280
atcttgatta taaagaagca aaatgtaata aggaaaaact acagttattt attaccccag   2340
aagctgattc tctgtcatgc ctgcaggaag acagtgtgaa aatgatcca aaaagcaaaa   2400 aagtttcaga tataaaagaa gaggtcttgg ctgcagcatg tcacccagta caacattcaa   2460
aagtggaata cagtgatact gactttcaat cccagaaaag tctttttatat gatcatgaaa   2520 atgccagcac tcttattttta actcctactt ccaaggatgt tctgtcaaac ctagtcatga   2580
```

```
tttctagagg caaagaatca tacaaaatgt cagacaagct caaaggtaac aattatgaat    2640
ctgatgttga attaaccaaa aatattccca tggaaaagaa tcaagatgta tgtgctttaa    2700
atgaaaatta taaaaacgtt gagctgttgc cacctgaaaa atacatgaga gtagcatcac    2760
cttcaagaaa ggtacaattc aaccaaaaca caaatctaag agtaatccaa aaaaatcaag    2820
aagaaactac ttcaatttca aaaataactg tcaatccaga ctctgaagaa cttttctcag    2880
acaatgagaa taattttgtc ttccaagtag ctaatgaaag gaataatctt gctttaggaa    2940
atactaagga acttcatgaa acagacttga cttgtgtaaa cgaacccatt ttcaagaact    3000
ctaccatggt tttatatgga gacacaggtg ataaacaagc aacccaagtg tcaattaaaa    3060
aagatttggt ttatgttctt gcagaggaga acaaaaatag tgtaaagcag catataaaaa    3120
tgactctagg tcaagattta aaatcggaca tctccttgaa tatagataaa ataccagaaa    3180
aaaataatga ttacatgaac aaatgggcag gactcttagg tccaatttca aatcacagtt    3240
ttggaggtag cttcagaaca gcttcaaata aggaaatcaa gctctctgaa cataacatta    3300
agaagagcaa aatgttcttc aaagatattg aagaacaata tcctactagt ttagcttgtg    3360
ttgaaattgt aaataccttg gcattagata atcaaaagaa actgagcaag cctcagtcaa    3420
ttaatactgt atctgcacat ttacagagta gtgtagttgt ttctgattgt aaaaatagtc    3480 atataaccccc tcagatgtta ttttccaagc aggattttaa ttcaaaccat aatttaacac    3540
ctagccaaaa ggcagaaatt acagaacttt ctactatatt agaagaatca ggaagtcagt    3600
ttgaatttac tcagtttaga aaaccaagct acatattgca gaagagtaca tttgaagtgc    3660
ctgaaaacca gatgactatc ttaaagacca cttctgagga atgcagagat gctgatcttc    3720
atgtcataat gaatgcccca tcgattggtc aggtagacag cagcaagcaa tttgaaggta    3780
cagttgaaat taaacggaag tttgctggcc tgttgaaaaa tgactgtaac aaaagtgctt    3840
ctggttattt aacagatgaa aatgaagtgg ggtttagggg cttttattct gctcatggca    3900
caaaactgaa tgtttctact gaagctctgc aaaaagctgt gaaactgttt agtgatattg    3960
agaatattag tgaggaaact tctgcagagg tacatccaat aagtttatct tcaagtaaat    4020
gtcatgattc tgttgtttca atgtttaaga tagaaaatca taatgataaa actgtaagtg    4080
aaaaaaataa taaatgccaa ctgatattac aaaataatat tgaaatgact actggcactt    4140
ttgttgaaga aattactgaa aattacaaga gaaatactga aaatgaagat aacaaatata    4200
ctgctgccag tagaaattct cataacttag aatttgatgg cagtgattca agtaaaaatg    4260
atactgtttg tattcataaa gatgaaacgg acttgctatt tactgatcag cacaacatat    4320
gtcttaaatt atctggccag tttatgaagg agggaaacac tcagattaaa gaagatttgt    4380
cagatttaac ttttttggaa gttgcgaaag ctcaagaagc atgtcatggt aatacttcaa    4440
ataaagaaca gttaactgct actaaaacgg agcaaaatat aaaagatttt gagacttctg    4500 atacatttt tcagactgca agtgggaaaa atattagtgt cgccaaagag tcatttaata    4560
aaattgtaaa tttctttgat cagaaaccag aagaattgca taacttttcc ttaaattctg    4620
aattacattc tgcataagaa aagaacaaaa tggacattct aagttatgag gaaacagaca    4680
tagttaaaca caaaatactg aaagaaagtg tcccagttgg tactgaaaat caactagtga    4740
ccttccaggg acaacccgaa cgtgatgaaa agatcaaaga acctactcta ttgggttttc    4800
atacagctag cggaaaaaaa gttaaaattg caaaggaatc tttggacaaa gtgaaaaacc    4860 ttttttgatga aaaagagcaa ggtactagtg aaatcaccag ttttagccat caatgggcaa    4920
```

-continued

```
agaccctaaa gtacagagag gcctgtaaag accttgaatt agcatgtgag accattgaga    4980
tcacagctgc cccaaagtgt aaagaaatgc agaattctct caataatgat aaaaaccttg    5040
tttctattga gactgtggtg ccacctaagc tcttaagtga taatttatgt agacaaactg    5100
aaaatctcaa aacatcaaaa agtatctttt tgaaagttaa agtacatgaa aatgtagaaa    5160
aagaaacagc aaaaagtcct gcaacttgtt acacaaatca gtccccttat tcagtcattg    5220
aaaattcagc cttagctttt tacacaagtt gtagtagaaa aacttctgtg agtcagactt    5280
cattacttga agcaaaaaaa tggcttagag aaggaatatt tgatggtcaa ccagaaagaa    5340
taaatactgc agattatgta ggaaattatt tgtatgaaaa taattcaaac agtactatag    5400
ctgaaaatga caaaaatcat ctctccgaaa aacaagatac ttatttaagt aacagtagca    5460
tgtctaacag ctattcctac cattctgatg aggtatataa tgattcagga tatctctcaa    5520
aaaataaact tgattctggt attgagccag tattgaagaa tgttgaagat caaaaaaaca    5580
ctagttttc caaagtaata tccaatgtaa aagatgcaaa tgcataccca caaactgtaa    5640
atgaagatat ttgcgttgag gaacttgtga ctagctcttc accctgcaaa aataaaaatg    5700
cagccattaa attgtccata tctaatagta ataattttga ggtagggcca cctgcattta    5760
ggatagccag tggtaaaatc gtttgtgttt cacatgaaac aattaaaaaa gtgaaagaca    5820
tatttacaga cagtttcagt aaagtaatta aggaaaacaa cgagaataaa tcaaaaattt    5880
gccaaacgaa aattatggca ggttgttacg aggcattgga tgattcagag atattcttc    5940
ataactctct agataatgat gaatgtagca cgcattcaca taaggttttt gctgacattc    6000
agagtgaaga aattttacaa cataaccaaa atatgtctgg attggagaaa gtttctaaaa    6060
tatcaccttg tgatgttagt ttggaaactt cagatatatg taaatgtagt atagggaagc    6120
ttcataagtc agtctcatct gcaaatactt gtgggatttt tagcacagca agtgaaaat    6180
ctgtccaggt atcagatgct tcattacaaa acgcaagaca agtgttttct gaaatagaag    6240
atagtaccaa gcaagtcttt tccaaagtat tgtttaaaag taacgaacat tcagaccagc    6300
tcacaagaga agaaaatact gctatacgta ctccagaaca tttaatatcc caaaaggct    6360
tttcatataa tgtggtaaat tcatctgctt tctctggatt tagtacagca agtggaaagc    6420
aagtttccat tttagaaagt ccttacacaa agttaagg agtgttagag aatttgatt    6480
taatcagaac tgagcatagt cttcactatt cacctacgtc tagacaaaat gtatcaaaaa    6540
tacttcctcg tgttgataag agaaacccag agcactgtgt aaactcagaa atggaaaaaa    6600
cctgcagtaa agaatttaaa ttatcaaata acttaaatgt tgaaggtggt tcttcagaaa    6660
ataatcactc tattaaagtt tctccatatc tctctcaatt tcaacaagac aaacaacagt    6720
tggtattagg aaccaaagtg tcacttgttg agaacattca tgttttggga aaagaacagg    6780
cttcacctaa aaacgtaaaa atggaaattg gtaaaactga aacttttct gatgttcctg    6840
tgaaaacaaa tatagaagtt tgttctactt actccaaaga ttcagaaaac tactttgaaa    6900
cagaagcagt agaaattgct aaagcttta tggaagatga tgaactgaca gattctaaac    6960
tgccaagtca tgccacacat tctctttta catgtccga aaatgaggaa atggttttgt    7020
caaattcaag aattggaaaa agaagaggag agcccttat cttagtggga gaaccctcaa    7080
tcaaaagaaa cttattaaat gaatttgaca ggataataga aaatcaagaa aaatccttaa    7140
aggcttcaaa aagcactcca gatggcacaa taaaagatcg aagattgttt atgcatcatg    7200
tttctttaga gccgattacc tgtgtaccct tcgcacaac taaggaacgt caagagatac    7260
agaatccaaa ttttaccgca cctggtcaag aatttctgtc taaatctcat ttgtatgaac    7320
```

```
atctgacttt ggaaaaatct tcaagcaatt tagcagtttc aggacatcca ttttatcaag    7380
tttctgctac aagaaatgaa aaaatgagac acttgattac tacaggcaga ccaaccaaag    7440
tctttgttcc acctttaaa actaaatcac attttcacag agttgaacag tgtgttagga    7500
atattaactt ggaggaaaac agacaaaagc aaaacattga tggacatggc tctgatgata    7560
gtaaaaataa gattaatgac aatgagattc atcagtttaa caaaaacaac tccaatcaag    7620
cagcagctgt aactttcaca aagtgtgaag aagaaccttt agatttaatt acaagtcttc    7680
agaatgccag agatatacag gatatgcgaa ttaagaagaa acaaaggcaa cgcgtctttc    7740
cacagccagg cagtctgtat cttgcaaaaa catccactct gcctcgaatc tctctgaaag    7800
cagcagtagg aggccaagtt ccctctgcgt gttctcataa acagctgtat acgtatggcg    7860
tttctaaaca ttgcataaaa attaacagca aaaatgcaga gtcttttcag tttcacactg    7920
aagattattt tggtaaggaa agtttatgga ctggaaaagg aatacagttg gctgatggtg    7980
gatggctcat accctccaat gatggaaagg ctggaaaaga agaattttat agggctctgt    8040
gtgacactcc aggtgtggat ccaaagctta tttctagaat ttgggtttat aatcactata    8100
gatggatcat atggaaactg gcagctatgg aatgtgcctt tcctaaggaa tttgctaata    8160
gatgcctaag cccagaaagg gtgcttcttc aactaaaata cagatatgat acggaaattg    8220
atagaagcag aagatcggct ataaaaaaga taatggaaag ggatgacaca gctgcaaaaa    8280
cacttgttct ctgtgtttct gacataattt cattgagcgc aaatatatct gaaacttcta    8340
gcaataaaac tagtagtgca gatacccaaa aagtggccat tattgaactt acagatgggt    8400
ggtatgctgt taaggcccag ttagatcctc ccctcttagc tgtcttaaag aatggcagac    8460
tgacagttgg tcagaagatt attcttcatg gagcagaact ggtgggctct cctgatgcct    8520
gtacacctct tgaagcccca gaatctctta tgttaaagat ttctgctaac agtactcggc    8580
ctgctcgctg gtataccaaa cttggattct ttcctgaccc tagacctttt cctctgccct    8640
tatcatcgct tttcagtgat ggaggaaatg ttggttgtgt tgatgtaatt attcaaagag    8700
catacccaat acagtggatg gagaagacat catctggatt atacatattt cgcaatgaaa    8760
gagaggaaga aaaggaagca gcaaaatatg tggaggccca acaaaagaga ctagaagcct    8820
tattcactaa aattcaggag gaatttgaag aacatgaaga aaacacaaca aaaccatatt    8880
taccatcacg tgcactaaca agacagcaag ttcgtgcttt gcaagatggt gcagagcttt    8940
atgaagcagt gaagaatgca gcagacccag cttaccttga gggttatttc agtgaagagc    9000
agttaagagc cttgaataat cacaggcaaa tgttgaatga taagaaacaa gctcagatcc    9060
agttggaaat taggaaggcc atggaatctg ctgaacaaaa ggaacaaggt ttatcaaggg    9120
atgtcacaac cgtgtggaag ttgcgtattg taagctattc aaaaaagaa aaagattcag    9180 ttatactgag tatttggcgt ccatcatcag atttatattc tctgttaaca gaaggaaaga    9240
gatacagaat ttatcatctt gcaacttcaa aatctaaaag taaatctgaa agagctaaca    9300
tacagttagc agcgacaaaa aaaactcagt atcaacaact accggtttca gatgaaattt    9360
tatttcagat ttaccagcca cgggagcccc ttcacttcag caaattttta gatccagact    9420
ttcagccatc ttgttctgag gtggacctaa taggatttgt cgtttctgtt gtgaaaaaaa    9480
caggacttgc ccctttcgtc tatttgtcag acgaatgtta caatttactg gcaataaagt    9540
tttggataga ccttaatgag gacattatta agcctcatat gttaattgct gcaagcaacc    9600
tccagtggcg accagaatcc aaatcaggcc ttcttacttt atttgctgga gattttctg    9660
```

-continued

| | |
|---|---|
| tgttttctgc tagtccaaaa gagggccact ttcaagagac attcaacaaa atgaaaaata | 9720 |
| ctgttgagaa tattgacata cttttgcaatg aagcagaaaa caagcttatg catatactgc | 9780 |
| atgcaaatga tcccaagtgg tccaccccaa ctaaagactg tacttcaggg ccgtacactg | 9840 |
| ctcaaatcat tcctggtaca ggaaacaagc ttctgatgtc ttctcctaat tgtgagatat | 9900 |
| attatcaaag tcctttatca cttttgtatgg ccaaaaggaa gtctgtttcc acacctgtct | 9960 |
| cagcccagat gacttcaaag tcttgtaaag gggagaaaga gattgatgac caaaagaact | 10020 |
| gcaaaaagag aagagccttg gatttcttga gtagactgcc tttacctcca cctgttagtc | 10080 |
| ccatttgtac atttgtttct ccggctgcac agaaggcatt tcagccacca aggagttgtg | 10140 |
| gcaccaaata cgaaacaccc ataaagaaaa aagaactgaa ttctcctcag atgactccat | 10200 |
| ttaaaaaatt caatgaaatt tctcttttgg aaagtaattc aatagctgac gaagaacttg | 10260 |
| cattgataaa tacccaagct cttttgtctg gttcaacagg agaaaaacaa tttatatctg | 10320 |
| tcagtgaatc cactaggact gctcccacca gttcagaaga ttatctcaga ctgaaacgac | 10380 |
| gttgtactac atctctgatc aaagaacagg agagttccca ggccagtacg gaagaatgtg | 10440 |
| agaaaaataa gcaggacaca attacaacta aaaaatatat ctaagcattt gcaaaggcga | 10500 |
| caataaatta ttgacgctta acctttccag tttataagac tggaatataa tttcaaacca | 10560 |
| cacattagta cttatgttgc acaatgagaa aagaaattag tttcaaattt acctcagcgt | 10620 |
| tgtgtatcg ggcaaaaatc gttttgcccg attccgtatt ggtatacttt tgcttcagtt | 10680 |
| gcatatctta aaactaaatg taatttatta actaatcaag aaaaacatct ttggctgagc | 10740 |
| tcggtggctc atgcctgtaa tcccaacact ttgagaagct gaggtgggag gagtgcttga | 10800 |
| ggccaggagt tcaagaccag cctgggcaac atagggagac ccccatcttt acaaagaaaa | 10860 |
| aaaaagggg aaaagaaaat cttttaaatc tttggatttg atcactacaa gtattatttt | 10920 |
| acaagtgaaa taaacatacc attttctttt agattgtgtc attaaatgga atgaggtctc | 10980 |
| ttagtacagt tattttgatg cagataattc cttttagttt agctactatt ttaggggatt | 11040 |
| tttttttagag gtaactcact atgaaatagt tctccttaat gcaaatatgt tggttctgct | 11100 |
| atagttccat cctgttcaaa agtcaggatg aatatgaaga gtggtgtttc cttttgagca | 11160 |
| attcttcatc cttaagtcag catgattata agaaaaatag aaccctcagt gtaactctaa | 11220 |
| ttccttttta ctattccagt gtgatctctg aaattaaatt acttcaacta aaaattcaaa | 11280 |
| tactttaaat cagaagattt catagttaat ttatttttt tttcaacaaa atggtcatcc | 11340 |
| aaactcaaac ttgagaaaat atcttgcttt caaattggca ctgatt | 11386 |

<210> SEQ ID NO 3
<211> LENGTH: 5425
<212> TYPE: DNA
<213> ORGANISM: Homo sapiens

<400> SEQUENCE: 3

| | |
|---|---|
| ggctccgttc catccttctg cacagggtat cgcctctctc cgtttggtac atcccctcct | 60 |
| cccccacgcc cggactgggg tggtagacgc cgcctccgct catcgcccct ccccatcggt | 120 |
| ttccgcgcga aaagccgggg cgcctgcgct gccgccgccg cgtctgctga agcctccgag | 180 |
| atgccggcgc gtaccgcccc agcccgggtg cccacactgg ccgtcccggc catctcgctg | 240 |
| cccgacgatg tccgcaggcg gctcaaagat ttggaaagag acagcttaac agaaaaggaa | 300 |
| tgtgtgaagg agaaattgaa tctcttgcac gaatttctgc aaacagaaat aagaatcag | 360 |
| ttatgtgact tggaaaccaa attacgtaaa gaagaattat ccgaggaggg ctacctggct | 420 |

```
aaagtcaaat ccctttaaa taaagatttg tccttggaga acggtgctca tgcttacaac    480
cgggaagtga atggacgtct agaaaacggg aaccaagcaa gaagtgaagc ccgtagagtg    540
ggaatggcag atgccaacag ccccccaaa cccctttcca aacctcgcac gcccaggagg     600
agcaagtccg atggagaggc taagcgttca agagaccctc ctgcctcagc ctcccaagta    660
actgggatta gagctgaacc ttcacctagc cccaggatta caaggaaaag caccaggcaa    720
accaccatca catctcattt tgcaaagggc cctgccaaac ggaaacctca ggaagagtct    780
gaaagagcca aatcggatga gtccatcaag gaagaagaca agaccagga tgagaagaga     840
cgtagagtta catccagaga acgagttgct agaccgcttc ctgcagaaga acctgaaaga    900
gcaaaatcag gaacgcgcac tgaaaaggaa gaagaaagag atgaaaaga gaaaagaga     960
ctccgaagtc aaaccaaaga accaacaccc aaacagaaac tgaaggagga gccggacaga   1020
gaagccaggg caggcgtgca ggctgacgag gacgaagatg gagacgagaa agatgagaag   1080
aagcacagaa gtcaacccaa agatctagct gccaaacgga ggcccgaaga aaaagaacct   1140
gaaaaagtaa atccacagat ttctgatgaa aaagacgagg atgaaaagga ggagaagaga   1200
cgcaaaacga cccccaaaga accaacggag aaaaaaatgg ctcgcgccaa aacagtcatg   1260
aactccaaga cccacccttc caagtgcatt cagtgcgggc agtacctgga cgaccctgac   1320
ctcaaatatg ggcagcaccc accagacgcg gtggatgagc cacagatgct gacaaatgag   1380
aagctgtcca tctttgatgc caacgagtct ggctttgaga gttatgaggc gcttccccag   1440
cacaaactga cctgcttcag tgtgtactgt aagcacggtc acctgtgtcc catcgacacc   1500
ggcctcatcg agaagaatat cgaactcttc ttttctggtt cagcaaaacc aatctatgat   1560
gatgacccat ctcttgaagg tggtgttaat ggcaaaaatc ttggccccat aaatgaatgg   1620
tggatcactg gctttgatgg aggtgaaaag gccctcatcg gcttcagcac ctcatttgcc   1680
gaatacattc tgatggatcc cagtcccgag tatgcgccca tatttgggct gatgcaggag   1740
aagatctaca tcagcaagat tgtggtggag ttcctgcaga gcaattccga ctcgacctat   1800
gaggacctga tcaacaagat cgagaccacg gttcctcctt ctggcctcaa cttgaaccgc   1860
ttcacagagg actccctcct gcgacacgcg cagtttgtgg tggagcaggt ggagagttat   1920
gacgaggccg gggacagtga tgagcagccc atcttcctga caccctgcat gcgggacctg   1980
atcaagctgg ctggggtcac gctggacag aggcgagccc aggcgaggcg cagaccatc    2040
aggcattcta ccagggagaa ggacagggga cccacgaaag ccaccaccac caagctggtc   2100
taccagatct tcgatacttt cttcgcagag caaattgaaa aggatgacag agaagacaag   2160
gagaacgcct ttaagcgccg gcgatgtggc gtctgtgagg tgtgtcagca gcctgagtgt   2220
gggaaatgta agcctgcaa ggacatggtt aaatttggtg gcagtggacg gagcaagcag   2280
gcttgccaag agcggaggtg tcccaatatg gccatgaagg aggcagatga cgatgaggaa   2340
gtcgatgata acatcccaga gatgccgtca cccaaaaaaa tgcaccaggg gaagaagaag   2400
aaacagaaca agaatcgcat ctcttgggtc ggagaagccg tcaagactga tgggaagaag   2460
agttactata agaaggtgtg cattgatgcg gaaaccctgg aagtggggga ctgtgtctct   2520
gttattccag atgattcctc aaaaccgctg tatctagcaa gggtcacggc gctgtgggag   2580
gacagcagca acgggcagat gtttcacgcc cactggttct gcgctgggac agacacagtc   2640
ctcggggcca cgtcggaccc tctggagctg ttccttggtgg atgaatgtga ggacatgcag   2700
cttttcatata tccacagcaa agtgaaagtc atctacaaag cccctccga aaactgggcc    2760
```

```
atggaggag gcatggatcc cgagtccctg ctggagggg acgacgggaa gacctacttc      2820
taccagctgt ggtatgatca agactacgcg agattcgagt cccctccaaa aacccagcca      2880
acagaggaca caagttcaa attctgtgtg agctgtgccc gtctggctga gatgaggcaa      2940
aaagaaatcc ccagggtcct ggagcagctc gaggacctgg atagccgggt cctctactac      3000
tcagccacca agaacggcat cctgtaccga gttggtgatg tgtgtacct gcccctgag       3060
gccttcacgt tcaacatcaa gctgtccagt cccgtgaaac gcccacgaa ggagcccgtg      3120
gatgaggacc tgtacccaga gcactaccgg aaatactccg actacatcaa aggcagcaac      3180
ctggatgccc ctgagcccta ccgaattggc cggatcaaag agatcttctg tcccaagaag      3240
agcaacggca ggcccaatga gactgacatc aaaatccggg tcaacaagtt ctacaggcct      3300
gagaacaccc acaagtccac tccagcgagc taccacgcag acatcaacct gctctactgg      3360
agcgacgagg aggccgtggt ggacttcaag gctgtgcagg gccgctgcac cgtggagtat      3420
ggggaggacc tgcccgagtg cgtccaggtg tactccatgg gcggcccaa ccgcttctac      3480
ttcctcgagg cctataatgc aaagagcaaa agctttgaag atcctcccaa ccatgcccgt      3540
agccctggaa acaaagggaa gggcaaggga aagggaagg gcaagcccaa gtcccaagcc      3600
tgtgagccga gcgagccaga gatagagatc aagctgccca gctgcggac cctggatgtg      3660
ttttctggct gcggggggtt gtcggaggga ttccaccaag caggcatctc tgacacgctg      3720
tgggccatcg agatgtggga ccctgcggcc caggcgttcc ggctgaacaa ccccggctcc      3780
acagtgttca cagaggactg caacatcctg ctgaagctgg tcatggctgg ggagaccacc      3840
aactcccgcg ccagcggct gccccagaag ggagacgtgg agatgctgtg cggcgggccg      3900
ccctgccagg gcttcagcgg catgaaccgc ttcaattcgc gcacctactc caagttcaaa      3960
aactctctgg tggtttcctt cctcagctac tgcgactact accggccccg gttcttcctc      4020
ctggagaatg tcaggaactt tgtctccttc aagcgctcca tggtcctgaa gctcacctc       4080
cgctgcctgt tccgcatggg ctatcagtgc accttcggcg tgctgcaggc cggtcagtac      4140
ggcgtggccc agactaggag gcgggccatc atcctggccg cggcccctgg agagaagctc      4200
cctctgttcc cggagccact gcacgtgttt gctccccggg cctgccagct gagcgtggtg      4260
gtggatgaca agaagtttgt gagcaacata accaggttga gctcgggtcc tttccggacc      4320
atcacggtgc gagacacgat gtccgacctg ccggaggtgc ggaatggagc ctcggcactg      4380
gagatctcct acaacgggga gcctcagtcc tggttccaga ggcagctccg gggcgcacag      4440
taccagccca tcctcaggga ccacatctgt aaggacatga gtgcattggt ggctgcccgc      4500
atgcggcaca tccccttggc cccagggtca gactggcgcg atctgcccaa catcgaggtg      4560
cggctctcag acggcaccat ggccaggaag ctgcggtata cccaccatga caggaagaac      4620
ggccgcagca gctctggggc cctccgtggg gtctgctcct gcgtggaagc cggcaaagcc      4680
tgcgaccccg cagccaggca gttcaacacc ctcatcccct ggtgcctgcc ccacaccggg      4740
aaccggcaca accactgggc tggcctctat ggaaggctcg agtgggacgg cttcttcagc      4800
acaaccgtca ccaaccccga gcccatgggc aagcagggcc gcgtgctcca cccagagcag      4860
caccgtgtgg tgagcgtgcg ggagtgtgcc cgctcccagg gcttccctga cacctaccgg      4920
ctcttcggca acatcctgga caagcaccgg caggtgggca atgccgtgcc accgcccctg      4980
gccaaagcca ttggcttgga gatcaagctt tgtatgttgg ccaaagcccg agagagtgcc      5040
tcagctaaaa taaggagga ggaagctgct aaggactagt tctgccctcc cgtcacccct      5100
gtttctggca ccaggaatcc ccaacatgca ctgatgttgt gttttttaaca tgtcaatctg      5160
```

```
tccgttcaca tgtgtggtac atggtgtttg tggccttggc tgacatgaag ctgttgtgtg      5220
aggttcgctt atcaactaat gatttagtga tcaaattgtg cagtactttg tgcattctgg      5280
attttaaaag ttttttatta tgcattatat caaatctacc actgtatgag tggaaattaa      5340
gactttatgt agttttata tgttgtaata tttcttcaaa taaatctctc ctataaacca       5400 aaaaaaaaa aaaaaaaaaa aaaaa                                              5425

<210> SEQ ID NO 4
<211> LENGTH: 2226
<212> TYPE: DNA
<213> ORGANISM: Homo sapiens

<400> SEQUENCE: 4
gtctgccggt cggttgtctg gctgcgcgcg ccacccgggc ctctccagtg ccccgcctgg        60
ctcggcatcc accccccagcc cgactcacac gtgggttccc gcacgtccgc cggccccccc      120
cgctgacgtc agcatagctg ttccacttaa ggcccctccc gcgcccagct cagagtgctg       180
cagccgctgc cgccgattcc ggatctcatt gccacgcgcc cccgacgacc gcccgacgtg       240
cattcccgat tccttttggt tccaagtcca atatggcaac tctaaaggat cagctgattt       300
ataatcttct aaaggaagaa cagacccccc agaataagat tacagttgtt ggggttggtg       360
ctgttggcat ggcctgtgcc atcagtatct taatgaagga cttggcagat gaacttgctc       420 tgttgatgt catcgaagac aaattgaagg gagagatgat ggatctccaa catggcagcc        480
ttttccttag aacaccaaag attgtctctg gcaaagacta taatgtaact gcaaactcca       540
agctggtcat tatcacggct ggggcacgtc agcaagaggg agaaagccgt cttaatttgg       600
tccagcgtaa cgtgaacatc tttaaattca tcattcctaa tgttgtaaaa tacagcccga       660
actgcaagtt gctattgtt tcaaatccag tggatatctt gacctacgtg gcttggaaga       720
taagtggttt tcccaaaaac cgtgttattg gaagcggttg caatctggat tcagcccgat       780
tccgttacct aatgggggaa aggctgggag ttcacccatt aagctgtcat gggtgggtcc       840
ttggggaaca tggagattcc agtgtgcctg tatggagtgg aatgaatgtt gctggtgtct       900
ctctgaagac tctgcaccca gatttaggga ctgataaaga taaggaacag tggaaagagg       960
ttcacaagca ggtggttgag agtgcttatg aggtgatcaa actcaaaggc tacacatcct      1020
gggctattgg actctctgta gcagatttgg cagagagtat aatgaagaat cttaggcggg      1080
tgcacccagt ttccaccatg attaagggtc tttacggaat aaaggatgat gtcttcctta      1140
gtgttccttg cattttggga cagaatggaa tctcagacct tgtgaaggtg actctgactt      1200
ctgaggaaga ggcccgtttg aagaagagtg cagatacact ttgggggatc caaaaggagc      1260 tgcaattta aagtcttctg atgtcatatc atttcactgt ctaggctaca acaggattct       1320
aggtggaggt tgtgcatgtt gtcctttta tctgatctgt gattaaagca gtaatatttt       1380
aagatggact gggaaaaaca tcaactcctg aagttagaaa taagaatggt ttgtaaaatc      1440
cacagctata tcctgatgct ggatggtatt aatcttgtgt agtcttcaac tggttagtgt      1500
gaaatagttc tgccacctct gacgcaccac tgccaatgct gtacgtactg catttgcccc      1560
ttgagccagg tggatgttta ccgtgtgtta tataacttcc tggctccttc actgaacatg      1620
cctagtccaa cattttttcc cagtgagtca catcctggga tccagtgtat aaatccaata      1680
tcatgtcttg tgcataattc ttccaaagga tcttattttg tgaactatat cagtagtgta      1740
cattaccata taatgtaaaa agatctacat acaaacaatg caaccaacta tccaagtgtt      1800
```

| | |
|---|---|
| ataccaacta aaaccccccaa taaaccttga acagtgacta ctttggttaa ttcattatat | 1860 |
| taagatataa agtcataaag ctgctagtta ttatattaat ttggaaatat taggctattc | 1920 |
| ttgggcaacc ctgcaacgat tttttctaac agggatatta ttgactaata gcagaggatg | 1980 |
| taatagtcaa ctgagttgta ttggtaccac ttccattgta agtcccaaag tattatatat | 2040 |
| ttgataataa tgctaatcat aattggaaag taacattcta tatgtaaatg taaaatttat | 2100 |
| ttgccaactg aatataggca atgatagtgt gtcactatag gaacacaga tttttgagat | 2160 |
| cttgtcctct ggaagctggt aacaattaaa aacaatctta aggcagggaa aaaaaaaaa | 2220 |
| aaaaaa | 2226 |

<210> SEQ ID NO 5
<211> LENGTH: 1196
<212> TYPE: DNA
<213> ORGANISM: Homo sapiens

<400> SEQUENCE: 5

| | |
|---|---|
| tgcccccagc cgaggggcag ccccggggcc gggcccggcg cgcacccggc cagcgcgccc | 60 |
| tcgccagctg cgctctgagt tctgggccag ctccccagag gcctaggcgc gccgccgcg | 120 |
| agggcgcggg gcagacaaag gaggcagaca aaggcgggcg cagcccagca gccgtgcggg | 180 |
| caccgggcga ggcaggccca ctcctcccgg tagcgggaag gatgaccacg ctcacacgac | 240 |
| aagacctcaa ctttggccaa gtggtggccg atgtgctctg cgagttcctg gaggtggctg | 300 |
| tgcatctcat cctctacgtg cgcgaggtct accccgtggg catcttccag aaacgcaaga | 360 |
| agtacaacgt gccggtccag atgtcctgcc acccggagct gaatcagtat atccaggaca | 420 |
| cgctgcactg cgtcaagcca ctcctggaga agaatgatgt ggagaaagtg gtggtggtga | 480 |
| ttttggataa agagcaccgc ccagtggaga aattcgtctt tgagatcacc cagcctccac | 540 |
| tgctgtccat cagctcagac tcgctgttgt ctcatgtgga gcagctgctc cgggccttca | 600 |
| tcctgaagat cagcgtgtgc gatgccgtcc tggaccacaa cccccaggc tgtaccttca | 660 |
| cagtcctggt gcacacgaga gaagccgcca ctcgcaacat ggagaagatc caggtcatca | 720 |
| aggatttccc ctggatcctg gcggatgagc aggatgtcca catgcatgac ccccggctga | 780 |
| taccactaaa aaccatgacg tcggacattt taaagatgca gctttacgtg gaagagcgcg | 840 |
| ctcataaagg cagctgaggg ggcacctgcc accccactga tgcccaaact gtcagacttt | 900 |
| ggggatccc cgcctagggc agtgctgcat ggctgccctg attccaagtg ctcttatcgc | 960 |
| ctctgtgtgt ggatcgcccg ccccagcccg gggccgctca ggtctgcttg gaggatgcct | 1020 |
| cccccaggag ggcagtgagg gatgccgcaa cctcgacttc tcagcctcct ggggttccgc | 1080 |
| cggccaacac tgtctgtctc aaatactgtg ctgtgagttg tttcaataaa ggggccccaa | 1140 |
| gggctgggct gaaaaaaaaa aaaaaaaaa aaaaaaaaa aaaaaaaaa aaaaaa | 1196 |

<210> SEQ ID NO 6
<211> LENGTH: 4639
<212> TYPE: DNA
<213> ORGANISM: Homo sapiens

<400> SEQUENCE: 6

| | |
|---|---|
| gagcgcgcac gtcccggagc ccatgccgac cgcaggcgcc gtatccgcgc tcgtctagca | 60 |
| gccccggtta cgcggttgca cgtcggcccc agccctgagg agccggaccg atgtggaaac | 120 |
| tgctgcccgc cgcgggcccg gcaggaggag aaccatacag acttttgact ggcgttgagt | 180 |
| acgttgttgg aaggaaaaac tgtgccattc tgattgaaaa tgatcagtcg atcagccgaa | 240 |

```
atcatgctgt gttaactgct aacttttctg taaccaacct gagtcaaaca gatgaaatcc    300
ctgtattgac attaaaagat aattctaagt atggtacctt tgttaatgag gaaaaaatgc    360
agaatggctt ttcccgaact ttgaagtcgg gggatggtat tacttttgga gtgtttggaa    420
gtaaattcag aatagagtat gagcctttgg ttgcatgctc ttcttgttta gatgtctctg    480
ggaaaactgc tttaaatcaa gctatattgc aacttggagg atttactgta aacaattgga    540
cagaagaatg cactcacctt gtcatggtat cagtgaaagt taccattaaa acaatatgtg    600
cactcatttg tggacgtcca attgtaaagc cagaatattt tactgaattc ctgaaagcag    660
ttgagtccaa gaagcagcct ccacaaattg aaagttttta cccacctctt gatgaaccat    720
ctattggaag taaaaatgtt gatctgtcag gacggcagga agaaaacaa atcttcaaag     780
ggaaaacatt tatattttg aatgccaaac agcataagaa attgagttcc gcagttgtct     840
ttggaggtgg ggaagctagg ttgataacag aagagaatga agaagaacat aatttctttt    900
tggctccggg aacgtgtgtt gttgatacag gaataacaaa ctcacagacc ttaattcctg    960
actgtcagaa gaaatggatt cagtcaataa tggatatgct ccaaaggcaa ggtcttagac   1020
ctattcctga agcagaaatt ggattggcgg tgattttcat gactacaaag aattactgtg   1080
atcctcaggg ccatcccagt acaggattaa agacaacaac tccaggacca agcctttcac   1140
aaggcgtgtc agttgatgaa aaactaatgc caagcgcccc agtgaacact acaacatacg   1200
tagctgacac agaatcagag caagcagata catgggattt gagtgaaagg ccaaaagaaa   1260
tcaaagtctc caaaatggaa caaaaattca gaatgctttc acaagatgca cccactgtaa   1320
aggagtcctg caaaacaagc tctaataata atagtatggt atcaaatact ttggctaaga   1380
tgagaatccc aaactatcag ctttcaccaa ctaaattgcc aagtataaat aaaagtaaag   1440
ataggggcttc tcagcagcag cagaccaact ccatcagaaa ctactttcag ccgtctacca   1500
aaaaaaggga aagggatgaa gaaaatcaag aaatgtcttc atgcaaatca gcaagaatag   1560
aaacgtcttg ttctcttta gaacaaacac aacctgctac accctcattg tggaaaaata   1620
aggagcagca tctatctgag aatgagcctg tggacacaaa ctcagacaat aacttattta   1680
cagatacaga ttttaaaatct attgtgaaaa attctgccag taaatctcat gctgcagaaa   1740
agctaagatc aaataaaaaa agggaaatgg atgatgtggc catagaagat gaagtattgg   1800
aacagttatt caaggacaca aaaccagagt tagaaattga tgtgaaagtt caaaaacagg   1860
aggaagatgt caatgttaga aaaggccaa ggatggatat agaaacaaat gacactttca   1920
gtgatgaagc agtaccagaa agtagcaaaa tatctcaaga aaatgaaatt gggaagaaac   1980
gtgaactcaa ggaagactca ctatggtcag ctaaagaaat atctaacaat gacaaacttc   2040
aggatgatag tgagatgctt ccaaaaaagc tgttattgac tgaatttaga tcactggtga   2100
ttaaaaactc tacttccaga aatccatctg gcataaatga tgattatggt caactaaaaa   2160
atttcaagaa attcaaaaag gtcacatatc ctggagcagg aaaacttcca cacatcattg   2220
gaggatcaga tctaatagct catcatgctc gaaagaatac agaactagaa gagtggctaa   2280
ggcaggaaat ggaggtacaa aatcaacatg caaaagaaga gtctcttgct gatgatcttt   2340
ttagatacaa tccttattta aaaaggagaa gataactgag gattttaaaa agaagccatg   2400
gaaaaacttc ctagtaagca tctacttcag gccaacaagg ttatatgaat atatagtgta   2460
tagaagcgat ttaagttaca atgttttatg gcctaaattt attaaataaa atgcacaaaa   2520
ctttgattct tttgtatgta acaattgttt gttctgtttt caggctttgt cattgcatct   2580
```

| | |
|---|---|
| tttttttcatt tttaaatgtg ttttgtttat taaatagtta atatagtcac agttcaaaat | 2640 |
| tctaaatgta cgtaaggtaa agactaaagt caccccttcca ccattgtcct agctacttgg | 2700 |
| ttcccctcag aaaaaaattc atgatactca tttcttatga atctttccag ggattttttga | 2760 |
| gtcctattca aattcctatt tttaaataat tccctacaca aatgatagca taacatatgc | 2820 |
| agtgttctac accttgcttt tttacttagt agattaaaaa ttataggaat atcaatataa | 2880 |
| tgttttaat attttttctt ttccattatg ctgtagtctt acctaaactc tggtgatcca | 2940 |
| aacaaaatgg cttcagtggt gcagatgtca cctacatgtt attctagtac tagaaactga | 3000 |
| agaccatgtg gagacttcat caaacatggg tttagtttc accagaatgg aaagacctgt | 3060 |
| acccctttt ggtggtctta ctgagctggg tgggtgtctg ttttgagctt atttagagtc | 3120 |
| ctagttttcc tacttataaa gtagaaatgg tgagattgtt ttcttttct accttaaagg | 3180 |
| gagatggtaa aaacaatga atgtcttttt tcaaacttta ttgacaagtg attttcaagt | 3240 |
| ctgtgttcaa aaatatattc atgtacctgt gatccagcaa gaagggagtt ccagtcaaga | 3300 |
| gtcactacaa ctgattagtt gtttagagaa tgagaaatgg aacagtgagg aatggaggcc | 3360 |
| atatttccat gacttccctt gtaaacagaa gcaacagaag ggacaagagg ctggcctcta | 3420 |
| catcactctc accttccaaa tcttgtggaa gtgcatctac ttgccagaac caaattaact | 3480 |
| tacttccaag ttctggctgc ttgcaggtgg aactccagct gcaagggagt tagggaaatg | 3540 |
| aaggtctttt tttaaaagct tctcagcctt cctagggaac agaaattggg tgagccaatc | 3600 |
| tgcaatttct actacaggca ttgagaccag ttagattatt gaaatattat agagagttat | 3660 |
| gaacacttaa attatgatag tggtatgaca ttggatagaa catgggatac tttagaagta | 3720 |
| gaattgacag ggcatattag ttgatgaaat ggagtcattt gagtctctta atagccatgt | 3780 |
| atcataatta ccaagtgaag ctggtggaac atatggtctc cattttacag ttaaggaata | 3840 |
| taatggacag attaatattg ttctctgtca tgcccacaat ccctttctaa ggaagactgc | 3900 |
| cctactatag cagttttat atttgtcaat ttatgaatat aatgaatgag agttctggta | 3960 |
| cctcctgtct ttacaaatat tggtgttgtc agtattttc cttttaacc attccaatcg | 4020 |
| gtgtgtagtg atgtttcatt ttggttttaa tttgtatatc cctgatagct ataattgggt | 4080 |
| catagaaatt ctttatacat tctagatgca agtctcttgt cggatatatg tattgagata | 4140 |
| ttacacctag tctgtggctt gactgttttc tttatgtctt ttgatgaata gaagttttaa | 4200 |
| attttgacaa ggtcaaattt atttttttct tttgtttgat attttttctc tccaatttaa | 4260 |
| ccccaagatt tcagatattc tgctctatta tataaacttt atattttat atttgtgatc | 4320 |
| taccttgaat tgatatgtat gttgtgaatt atggatcagg gttcttttt tccccatac | 4380 |
| aagtatccag tcattgtaac actgtttatt gaaagaatta tcctttcctc attaaattac | 4440 |
| cttgccaatt agtaaaaaat caattaacca taatggtgga tctgtttctg gactttctgt | 4500 |
| ttggttacac tgaaatgttt gtccatcctt gcactcactc ataccatact gccttgaatt | 4560 |
| actgtagctg catagatgct ccttaagttg ggattacatt gtaataaacg caatgtaagt | 4620 |
| taaaaaaaaa aaaaaaaa | 4639 |

<210> SEQ ID NO 7
<211> LENGTH: 3228
<212> TYPE: DNA
<213> ORGANISM: Homo sapiens

<400> SEQUENCE: 7

| | |
|---|---|
| caggcgcagt gcaggactgc tccgagcacg cctacgcgcg cattttctcc ccttcctctc | 60 |

```
cctctttcca ctttcctctc ccttttctc ctctcctttc ccctcccac cacttggtct      120 ttcagtcttt cagtcagttc gtttaggtct ctccttccga cccccacccc cagctcctct      180 cccttcctt ttccccctcc ccctttcctt tccgtctca cgcgccaggc cgcttgcaca      240
tgcgcattag gtacaaagcc tcgctctttg tccccatctg tcgttcacac gaactcaagc      300
ctttggcatt cggcagccaa tagaatctaa gaaatggcgg aaaaatgatt ccgcctcggg      360
agctaaacct tgattggcag tttagctaac caatcgagaa cgccattttg taccccttgg      420
caggcaccga gctccgtcgt ctcgtttccg gcggtcgcgc gctctttct cgggacggga      480 gaggccgtgt agcgtcgccg ttactccgag gagataccag tcggtagagg agaagtcgag      540
gttagaggga actgggaggc actttgctgt ctgcaatcga agttgagagg cccagtattt      600
aggcgacagt gaatttatta ctctgaagag ggttctgcac atatttccaa attatattgg      660
tggtcatcag aagtaggtga taggaagaaa tacttctcaa gggtgcaaaa atgcagagta      720
ataaaacttt taacttggag aagcaaaacc atactccaag aaagcatcat caacatcacc      780
accagcagca gcaccaccag cagcaacagc agcagccgcc accaccgcca atacctgcaa      840
atgggcaaca ggccagcagc caaaatgaag gcttgactat tgacctgaag aatttagaa      900 aaccaggaga gaagaccttc acccaacgaa gccgtctttt tgtgggaaat cttcctcccg      960
acatcactga ggaagaaatg aggaaactat ttgagaaata tggaaaggca ggcgaagtct      1020
tcattcataa ggataaagga tttggcttta tccgcttgga aacccgaacc ctagcggaga      1080
ttgccaaagt ggagctggac aatatgccac tccgtggaaa gcagctgcgt gtgcgctttg      1140
cctgccatag tgcatccctt acagttcgaa accttcctca gtatgtgtcc aacgaactgc      1200
tggaagaagc cttttctgtg tttggccagg tagagagggc tgtagtcatt gtggatgatc      1260
gaggaaggcc ctcaggaaaa ggcattgttg agttctcagg aagccagct gctcggaaag      1320 ctctggacag atgcagtgaa ggctccttcc tgctaaccac atttcctcgt cctgtgactg      1380
tggagcccat ggaccagtta gatgatgaag agggacttcc agagaagctg gttataaaaa      1440
accagcaatt tcacaaggaa cgagagcagc cacccagatt tgcacagcct ggctcctttg      1500
agtatgaata tgccatgcgc tggaaggcac tcattgagat ggagaagcag cagcaggacc      1560
aagtggaccg caacatcaag gaggctcgtg agaagctgga gatggagatg aagctgcac      1620 gccatgagca ccaggtcatg ctaatgagac aggatttgat gaggcgccaa gaagaacttc      1680
ggaggatgga agagctgcac aaccaagagg tgcaaaaacg aaagcaactg gagctcaggc      1740
aggaggaaga gcgcaggcgc cgtgaagaag agatgcggcg gcagcaagaa gaaatgatgc      1800
ggcgacagca ggaaggattc aagggaacct tccctgatgc gagagagcag gagattcgga      1860
tgggtcagat ggctatggga ggtgctatgg gcataaacaa cagaggtgcc atgcccctg      1920 ctcctgtgcc agctggtacc ccagctcctc caggacctgc cactatgatg ccggatggaa      1980
ctttgggatt gaccccacca caaactgaac gctttggtca ggctgctaca atggaaggaa      2040
ttggggcaat tggtggaact cctcctgcat tcaaccgtgc agctcctgga gctgaatttg      2100
ccccaaacaa acgtcgccga tactaataag ttgcagtgtc tagtttctca aaacccttaa      2160
aagaaggacc cttttggac tagccagaat tctaccctgg aaaagtgtta gggattcctt      2220
ccaatagtta gatctacccct gcctgtacta ctctagggag tatgctggag gcagagggca      2280
agggaggggt ggtattaaac aagtcaattc tgtgtggtat attgtttaat cagttctgtg      2340
tggtgcattc ctgaagtctc taatgtgact gttgagggcc tggggaaacc atggcaaagt      2400
```

```
ggatccagtt agagcccatt aatcttgatc attccggttt tttttttttt tgtccatctt   2460
gtttcatttg cttgccccgc ccccgagacg gagtcttact ctgtcgccca ggctggagtg   2520
tagtggcatg atctcggctc actgcaatct ctgcctcccg ggttcaagct tgtccaggtt   2580
gatcttgaac tcctgacctc gtgatctacc cacctcggcc tcccaaaatg ctgggattac   2640
aggggtgagc caccgtgccc aacctcactt gcttcttatc cttacactcc cccagcccca   2700
gagaaactgc cacatacacc acaaaaacca aacatccccc aatgacctta gcccattgc    2760 tccattcact cccaggtgag aattcaggca aacgtccaca aaggtcacag gcagcgtaca   2820
tacggttctg ttataccccca tatattaccc cttcatgtcc taagaagac attttctctt    2880 agagattttc attttagtgt atctttaaaa aaaaatcttg tgttaacttg cctccatctt   2940
tttcttgggt gaggacaccc aggaatgacc cttttgtgtc tatgatgttg ctgttcacag   3000
cttttcttga taggcctagt acaatcttgg gaacaggggtt actgtatact gaaggtctga   3060
cagtagctct tagactcgcc tatcttaggt agtcatgctg tgcattttttt ttttcattgg   3120 tgtactgtgt ttgatttgtc tcatatattt ggagttttttc tgaaaaatgg agcagtaatg   3180
cagcatcaac ctattaaaat acattttaag cctttttaaaa aaaaaaaa                3228
```

<210> SEQ ID NO 8
<211> LENGTH: 13509
<212> TYPE: DNA
<213> ORGANISM: Homo sapiens

<400> SEQUENCE: 8

```
ggggcatttc cgggtccggg ccgagcgggc gcacgcgcgg gagcgggact cggcggcatg     60
gcgggctccg gagccggtgt gcgttgctcc ctgctgcggc tgcaggagac cttgtccgct   120
gcggaccgct gcggtgctgc cctggccggt catcaactga tccgcggcct ggggcaggaa   180
tgcgtcctga gcagcagccc cgcggtgctg gcattacaga catctttagt tttttccaga   240
gatttcggtt tgcttgtatt tgtccggaag tcactcaaca gtattgaatt tcgtgaatgt   300
agagaagaaa tcctaaagtt tttatgtatt ttcttagaaa aaatgggcca gaagatcgca   360
ccttactctg ttgaaattaa gaacacttgt accagtgttt atacaaaaga tagagctgct   420
aaatgtaaaa ttccagcccct ggaccttctt attaagttac ttcagacttt tagaagttct   480
agactcatgg atgaatttaa aattggagaa ttatttagta aattctatgg agaacttgca   540
ttgaaaaaaa aaataccaga tacagtttta gaaaagtat atgagctcct aggattattg   600
ggtgaagttc atcctagtga gatgataaat aatgcagaaa acctgttccg cgcttttctg   660
ggtgaactta agacccagat gacatcagca gtaagagagc ccaaactacc tgttctggca   720
ggatgtctga aggggttgtc ctcacttctg tgcaacttca ctaagtccat ggaagaagat   780 cccccagactt caagggagat ttttaatttt gtactaaagg caattcgtcc tcagattgat   840
ctgaagagat atgctgtgcc ctcagctggc ttgcgcctat ttgccctgca tgcatctcag   900
tttagcacct gccttctgga caactacgtg tctctatttg aagtcttgtt aaagtggtgt   960
gcccacacaa atgtagaatt gaaaaaagct gcactttcag ccctggaatc ctttctgaaa  1020
caggtttcta atatggtggc gaaaaatgca gaaatgcata aaaataaact gcagtacttt  1080
atggagcagt tttatggaat catcagaaat gtggattcga caacaagga gttatctatt   1140 gctatccgtg gatatggact ttttgcagga ccgtgcaagg ttataaacgc aaaagatgtt  1200
gacttcatgt acgttgagct cattcagcgc tgcaagcaga tgttcctcac ccagacagac  1260
actggtgacg accgtgttta tcagatgcca agcttcctcc agtctgttgc aagcgtcttg  1320
```

```
ctgtaccttg acacagttcc tgaggtgtat actccagttc tggagcacct cgtggtgatg    1380
cagatagaca gtttcccaca gtacagtcca aaaatgcagc tggtgtgttg cagagccata    1440
gtgaaggtgt tcctagcttt ggcagcaaaa gggccagttc tcaggaattg cattagtact    1500
gtggtgcatc agggtttaat cagaatatgt tctaaaccag tggtccttcc aaagggccct    1560
gagtctgaat ctgaagacca ccgtgcttca ggggaagtca gaactggcaa atggaaggtg    1620
cccacataca aagactacgt ggatctcttc agacatctcc tgagctctga ccagatgatg    1680
gattctattt tagcagatga agcattttc tctgtgaatt cctccagtga agtctgaat    1740 catttacttt atgatgaatt tgtaaaatcc gttttgaaga ttgttgagaa attggatctt    1800
acacttgaaa tacagactgt tggggaacaa gagaatggag atgaggcgcc tggtgtttgg    1860
atgatcccaa cttcagatcc agcggctaac ttgcatccag ctaaacctaa agattttcg    1920 gctttcatta acctggtgga attttgcaga gagattctcc ctgagaaaca agcagaattt    1980
tttgaaccat gggtgtactc attttcatat gaattaattt tgcaatctac aaggttgccc    2040
ctcatcagtg gtttctacaa attgctttct attacagtaa gaaatgccaa gaaaataaaa    2100
tatttcgagg gagttagtcc aaagagtctg aaacactctc ctgaagaccc agaaaagtat    2160
tcttgctttg ctttatttgt gaaatttggc aaagaggtgg cagttaaaat gaagcagtac    2220
aaagatgaac ttttggcctc ttgtttgacc tttcttctgt ccttgccaca caacatcatt    2280
gaactcgatg ttagagccta cgttcctgca ctgcagatgg ctttcaaact gggcctgagc    2340 tatacccct tggcagaagt aggcctgaat gctctagaag aatggtcaat ttatattgac    2400
agacatgtaa tgcagcctta ttacaaagac attctcccct gcctggatgg atacctgaag    2460
acttcagcct tgtcagatga gaccaagaat aactgggaag tgtcagctct ttctcgggct    2520
gcccagaaag gatttaataa agtggtgtta agcatctga agaagacaaa gaacctttca    2580
tcaaacgaag caatatcctt agaagaaata agaattagag tagtacaaat gcttggatct    2640
ctaggaggac aaataaacaa aaatcttctg acagtcacgt cctcagatga gatgatgaag    2700
agctatgtgg cctgggacag agagaagcgg ctgagctttg cagtgcccct tagagagatg    2760
aaacctgtca ttttcctgga tgtgttcctg cctcgagtca cagaattagc gctcacagcc    2820
agtgacagac aaactaaagt tgcagcctgt gaacttttac atagcatggt tatgtttatg    2880
ttgggcaaag ccacgcagat gccagaaggg ggacaggag ccccacccat gtaccagctc    2940
tataagcgga cgtttcctgt gctgcttcga cttgcgtgtg atgttgatca ggtgacaagg    3000
caactgtatg agccactagt tatgcagctg attcactggt tcactaacaa caagaaatt    3060 gaaagtcagg atactgttgc cttactagaa gctatattgg atggaattgt ggaccctgtt    3120
gacagtactt taagagattt ttgtggtcgg tgtattcgag aattccttaa atggtccatt    3180
aagcaaataa caccacagca gcaggagaag agtccagtaa acaccaaatc gcttttcaag    3240
cgactttata gccttgcgct tcaccccaat gcttttcaaga ggctgggagc atcacttgcc    3300
tttaataata tctacaggga attcagggaa gaagagtctc tggtggaaca gtttgtgttt    3360
gaagccttgg tgatatacat ggagagtctg gccttagcac atgcagatga gaagtcctta    3420
ggtacaattc aacagtgttg tgatgccatt gatcacctat gccgcatcat tgaaaagaag    3480
catgtttctt taaataaagc aaagaaacga cgtttgccgc gaggatttcc accttccgca    3540
tcattgtgtt tattggatct ggtcaagtgg ctttttagctc attgtgggag ccccagaca    3600 gaatgtcgac acaaatccat tgaactcttt tataaattcg ttcctttatt gccaggcaac    3660
```

```
agatccccta atttgtggct gaaagatgtt ctcaaggaag aaggtgtctc tttttctcatc   3720
aacacctttg agggggtgg ctgtggccag ccctcgggca tcctggccca gcccacccctc   3780
ttgtaccttc gggggccatt cagcctgcag gccacgctat gctggctgga cctgctcctg   3840
gccgcgttgg agtgctacaa cacgttcatt ggcgagagaa ctgtaggagc gctccaggtc   3900
ctaggtactg aagcccagtc ttcacttttg aaagcagtgg ctttcttctt agaaagcatt   3960
gccatgcatg acattatagc agcagaaaag tgctttggca ctggggcagc aggtaacaga   4020
acaagcccac aagagggaga aaggtacaac tacagcaaat gcaccgttgt ggtccggatt   4080
atggagttta ccacgactct gctaaacacc tccccggaag gatggaagct cctgaagaag   4140
gacttgtgta atacacacct gatgagagtc ctggtgcaga cgctgtgtga gcccgcaagc   4200
ataggtttca acatcggaga cgtccaggtt atggctcatc ttcctgatgt ttgtgtgaat   4260
ctgatgaaag ctctaaagat gtccccatac aaagatatcc tagagaccca tctgagagag   4320
aaaataacag cacagagcat tgaggagctt tgtgccgtca acttgtatgg ccctgacgcg   4380
caagtggaca ggagcaggct ggctgctgtt gtgtctgcct gtaaacagct tcacagagct   4440
gggcttctgc ataatatatt accgtctcag tccacagatt tgcatcattc tgttggcaca   4500
gaacttcttt ccctggttta taaggcatt gcccctggag atgagagaca gtgtctgcct   4560
tctctagacc tcagttgtaa gcagctggcc agcggacttc tggagttagc ctttgctttt   4620
ggaggactgt gtgagcgcct tgtgagtctt ctcctgaacc cagcggtgct gtccacggcg   4680
tccttgggca gctcacaggg cagcgtcatc cacttctccc atggggagta tttctatagc   4740
ttgttctcag aaacgatcaa cacggaatta ttgaaaaatc tggatcttgc tgtattggag   4800
ctcatgcagt cttcagtgga taataccaaa atggtgagtg ccgttttgaa cggcatgtta   4860
gaccagagct tcagggagcg agcaaaccag aaacaccaag gactgaaact tgcgactaca   4920
attctgcaac actggaagaa gtgtgattca tggtgggcca agattccccc tctcgaaact   4980
aaaatggcag tgctggcctt actggcaaaa attttacaga ttgattcatc tgtatctttt   5040
aatacaagtc atggttcatt ccctgaagtc tttacaacat atattagtct acttgctgac   5100
acaaagctgg atctacattt aaagggccaa gctgtcactc ttcttccatt cttcaccagc   5160
ctcactggag gcagtctgga ggaacttaga cgtgttctgg agcagctcat cgttgctcac   5220
ttccccatgc agtccaggga atttcctcca ggaactccgc ggttcaataa ttatgtggac   5280
tgcatgaaaa agtttctaga tgcattggaa ttatctcaaa gccctatgtt gttggaattg   5340
atgacagaag ttctttgtcg ggaacagcag catgtcatgg aagaattatt tcaatccagt   5400
ttcaggagga ttgccagaag gggttcatgt gtcacacaag taggccttct ggaaagcgtg   5460
tatgaaatgt tcaggaagga tgaccccgc ctaagtttca cacgccagtc ctttgtggac   5520
cgctccctcc tcactctgct gtggcactgt agcctggatg ctttgagaga attcttcagc   5580
acaattgtgg tggatgccat tgatgtgttg aagtccaggt ttacaaagct aaatgaatct   5640
acctttgata ctcaaatcac caagaagatg ggctactata agattctaga cgtgatgtat   5700
tctcgccttc ccaaagatga tgttcatgct aaggaatcaa aaattaatca agttttccat   5760
ggctcgtgta ttacagaagg aaatgaactt acaaagacat tgattaaatt gtgctacgat   5820
gcatttacag agaacatggc aggagagaat cagctgctgg agaggagaag acttttaccat  5880
tgtgcagcat acaactgcgc catatctgtc atctgctgtg tcttcaatga gttaaaattt   5940
taccaaggtt ttctgtttag tgaaaaacca gaaaagaact tgcttatttt tgaaaatctg   6000
atcgacctga agcgccgcta taattttcct gtagaagttg aggttcctat ggaaagaaag   6060
```

```
aaaaagtaca ttgaaattag gaaagaagcc agagaagcag caaatgggga ttcagatggt   6120
ccttcctata tgtcttccct gtcatatttg gcagacagta ccctgagtga ggaaatgagt   6180
caatttgatt tctcaaccgg agttcagagc tattcataca gctcccaaga ccctagacct   6240
gccactggtc gttttcggag acgggagcag cgggacccca cggtgcatga tgatgtgctg   6300
gagctggaga tggacgagct caatcggcat gagtgcatgg cgcccctgac ggccctggtc   6360
aagcacatgc acagaagcct gggcccgcct caaggagaag aggattcagt gccaagagat   6420
cttccttctt ggatgaaatt cctccatggc aaactgggaa atccaatagt accattaaat   6480
atccgtctct tcttagccaa gcttgttatt aatacagaag aggtctttcg cccttacgcg   6540
aagcactggc ttagccccct gctgcagctg gctgcttctg aaaacaatgg aggagaagga   6600
attcactaca tggtggttga gatagtggcc actattcttt catggacagg cttggccact   6660
ccaacagggg tccctaaaga tgaagtgtta gcaaatcgat tgcttaattt cctaatgaaa   6720
catgtctttc atccaaaaag agctgtgttt agacacaacc ttgaaattat aaagacccct   6780
gtcgagtgct ggaaggattg tttatccatc ccttataggt taatatttga aaagttttcc   6840
ggtaaagatc ctaattctaa agacaactca gtagggattc aattgctagg catcgtgatg   6900
gccaatgacc tgcctcccta tgacccacag tgtggcatcc agagtagcga atacttccag   6960
gctttggtga ataatatgtc ctttgtaaga tataaagaag tgtatgccgc tgcagcagaa   7020
gttctaggac ttatacttcg atatgttatg gagagaaaaa acatactgga ggagtctctg   7080
tgtgaactgg ttgcgaaaca attgaagcaa catcagaata ctatggagga caagtttatt   7140
gtgtgcttga acaaagtgac caagagcttc cctcctcttg cagacaggtt catgaatgct   7200
gtgttctttc tgctgccaaa atttcatgga gtgttgaaaa cactctgtct ggaggtggta   7260
ctttgtcgtg tggagggaat gacagagctg tacttccagt taaagagcaa ggacttcgtt   7320
caagtcatga gacatagaga tgatgaaaga caaaaagtat gtttggacat aatttataag   7380
atgatgccaa agttaaaacc agtagaactc cgagaacttc tgaaccccgt tgtggaattc   7440
gtttcccatc cttctacaac atgtagggaa caaatgtata atattctcat gtggattcat   7500
gataattaca gagatccaga aagtgagaca gataatgact cccaggaaat atttaagttg   7560
gcaaaagatg tgctgattca aggattgatc gatgagaacc ctggacttca attaattatt   7620
cgaaatttct ggagccatga aactaggtta ccttcaaata ccttggaccg gttgctggca   7680
ctaaattcct tatattctcc taagatagaa gtgcactttt taagtttagc aacaaatttt   7740
ctgctcgaaa tgaccagcat gagcccagat tatccaaacc ccatgttcga gcatcctctg   7800
tcagaatgcg aatttcagga atataccatt gattctgatt ggcgtttccg aagtactgtt   7860
ctcactccga tgtttgtgga gcccaggcc tcccagggca ctctccagac ccgtacccag   7920
gaagggtccc tctcagctcg ctggccagtg gcagggcaga taagggccac ccagcagcag   7980
catgacttca cactgacaca gactgcagat ggaagaagct catttgattg gctgaccggg   8040
agcagcactg acccgctggt cgaccacacc agtccctcat ctgactcctt gctgtttgcc   8100
cacaagagga gtgaaaggtt acagagagca cccttgaagt cagtggggcc tgattttggg   8160
aaaaaaaggc tgggccttcc aggggacgag gtggataaca aagtgaaagg tgcggccggc   8220
cggacggacc tactacgact gcgcagacgg tttatgaggg accaggagaa gctcagtttg   8280
atgtatgcca gaaaaggcgt tgctgagcaa aaacgagaga aggaaatcaa gagtgagtta   8340
aaaatgaagc aggatgccca ggtcgttctg tacagaagct accggcacgg agaccttcct   8400
```

```
gacattcaga tcaagcacag cagcctcatc accccgttac aggccgtggc ccagagggac    8460
ccaataattg caaaacagct ctttagcagc ttgttttctg gaattttgaa agagatggat    8520
aaatttaaga cactgtctga aaaaacaac atcactcaaa agttgcttca agacttcaat     8580
cgttttctta ataccacctt ctctttcttt ccacccttttg tctcttgtat tcaggacatt   8640
agctgtcagc acgcagccct gctgagcctc gacccagcgg ctgttagcgc tggttgcctg    8700
gccagcctac agcagcccgt gggcatccgc ctgctagagg aggctctgct ccgcctgctg    8760
cctgctgagc tgcctgccaa gcgagtccgt gggaaggccc gcctccctcc tgatgtcctc    8820
agatgggtgg agcttgctaa gctgtataga tcaattggag aatacgacgt cctccgtggg    8880
atttttacca gtgagatagg aacaaagcaa atcactcaga gtgcattatt agcagaagcc    8940
agaagtgatt attctgaagc tgctaagcag tatgatgagg ctctcaataa acaagactgg    9000
gtagatggtg agcccacaga agccgagaag gattttttggg aacttgcatc ccttgactgt   9060
tacaaccacc ttgctgagtg gaaatcactt gaatactgtt ctacagccag tatagacagt    9120
gagaacccccc cagacctaaa taaaatctgg agtgaaccat tttatcagga aacatatcta   9180
ccttacatga tccgcagcaa gctgaagctg ctgctccagg gagaggctga ccagtccctg    9240
ctgacattta ttgacaaagc tatgcacggg gagctccaga aggcgattct agagcttcat    9300
tacagtcaag agctgagtct gctttacctc ctgcaagatg atgttgacag agccaaatat    9360
tacattcaaa atggcattca gagttttatg cagaattatt ctagtattga tgtcctctta    9420
caccaaagta gactcaccaa attgcagtct gtacaggctt taacagaaat tcaggagttc    9480
atcagctttta taagcaaaca aggcaattta tcatctcaag ttccccttaa gagacttctg    9540
aacacctgga caaacagata tccagatgct aaaatggacc caatgaacat ctgggatgac    9600
atcatcacaa atcgatgttt ctttctcagc aaaatagagg agaagcttac ccctcttcca    9660
gaagataata gtatgaatgt ggatcaagat ggagaccccca gtgacaggat ggaagtgcaa    9720
gagcaggaag aagatatcag ctcccctgatc aggagttgca agttttccat gaaaatgaag    9780
atgatagaca gtgcccggaa gcagaacaat ttctcacttg ctatgaaact actgaaggag    9840
ctgcataaag agtcaaaaac cagagacgat tggctggtga gctgggtgca gagctactgc    9900
cgcctgagcc actgccggag ccggtcccag ggctgctctg agcaggtgct cactgtgctg    9960
aaaacagtct ctttgttgga tgagaacaac gtgtcaagct acttaagcaa aaatattctg   10020
gctttccgtg accagaacat tctcttgggt acaacttaca ggatcatagc gaatgctctc   10080
agcagtgagc cagcctgcct tgctgaaatc gaggaggaca aggctagaag aatcttagag   10140
cttttctggat ccagttcaga ggattcagag aaggtgatcg cgggtctgta ccagagagca   10200
ttccagcacc tctctgaggc tgtgcaggcg gctgaggagg aggcccagcc tccctcctgg   10260
agctgtgggc ctgcagctgg ggtgattgat gcttacatga cgctggcaga tttctgtgac   10320
caacagctgc gcaaggagga agagaatgca tcagttattg attctgcaga actgcaggcg   10380
tatccagcac ttgtggtgga gaaaatgttg aaagctttaa aattaaattc caatgaagcc   10440
agattgaagt ttcctagatt acttcagatt atagaacggt atccagagga gactttgagc   10500
ctcatgacaa aagagatctc ttccgttccc tgctggcagt tcatcagctg gatcagccac   10560
atggtggcct tactggacaa agaccaagcc gttgctgttc agcactctgt ggaagaaatc   10620
actgataact acccgcaggc tattgtttat cccttcatca taagcagcga aagctattcc   10680
ttcaaggata cttctactgg tcataagaat aaggagtttt ggcaaggat taaaagtaag     10740
ttggatcaag gaggagtgat tcaagatttt attaatgcct tagatcagct ctctaatcct   10800
```

```
gaactgctct ttaaggattg gagcaatgat gtaagagctg aactagcaaa aaccccctgta   10860 aataaaaaaa acattgaaaa aatgtatgaa agaatgtatg cagccttggg tgacccaaag   10920
gctccaggcc tgggggcctt tagaaggaag tttattcaga cttttggaaa agaatttgat   10980
aaacattttg ggaaaggagg ttctaaacta ctgagaatga agctcagtga cttcaacgac   11040
attaccaaca tgctactttt aaaaatgaac aaagactcaa agcccctgg gaatctgaaa    11100 gaatgttcac cctggatgag cgacttcaaa gtggagttcc tgagaaatga gctggagatt   11160
cccggtcagt atgacggtag gggaaagcca ttgccagagt accacgtgcg aatcgccggg   11220
tttgatgagc gggtgacagt catggcgtct ctgcgaaggc ccaagcgcat catcatccgt   11280
ggccatgacg agagggaaca ccctttcctg gtgaagggtg gcgaggacct gcggcaggac   11340
cagcgcgtgg agcagctctt ccaggtcatg aatgggatcc tggcccaaga ctccgcctgc   11400
agccagaggg ccctgcagct gaggacctat agcgttgtgc ccatgacctc caggttagga   11460
ttaattgagt ggcttgaaaa tactgttacc ttgaaggacc ttcttttgaa caccatgtcc   11520
caagaggaga aggcggctta cctgagtgat cccagggcac cgccgtgtga atataaagat   11580
tggctgacaa aaatgtcagg aaaacatgat gttggagctt acatgctaat gtataagggc   11640
gctaatcgta ctgaaacagt cacgtctttt agaaaacgag aaagtaaagt gcctgctgat   11700
ctcttaaagc gggccttcgt gaggatgagt acaagccctg aggctttcct ggcgctccgc   11760
tcccacttcg ccagctctca cgctctgata tgcatcagcc actggatcct cgggattgga   11820
gacagacatc tgaacaactt tatggtggcc atggagactg gcggcgtgat cgggatcgac   11880
tttgggcatg cgtttggatc cgctacacag tttctgccag tccctgagtt gatgcctttt   11940
cggctaactc gccagtttat caatctgatg ttaccaatga agaaacggg ccttatgtac    12000 agcatcatgg tacacgcact ccgggccttc cgctcagacc ctggcctgct caccaacacc   12060
atggatgtgt ttgtcaagga gccctccttt gattggaaaa attttgaaca gaaaatgctg   12120 aaaaaggag ggtcatggat tcaagaaata aatgttgctg aaaaaaattg gtaccccga    12180 cagaaaatat gttacgctaa gagaaagtta gcaggtgcca atccagcagt cattacttgt   12240
gatgagctac tcctgggtca tgagaaggcc cctgccttca gagactatgt ggctgtggca   12300
cgaggaagca agatcacaa cattcgtgcc caagaaccag agagtgggct ttcagaagag   12360
actcaagtga agtgcctgat ggaccaggca acagacccca acatccttgg cagaacctgg   12420
gaaggatggg agccctggat gtgaggtctg tgggagtctg cagatagaaa gcattacatt   12480
gtttaaagaa tctactatac tttggttggc agcattccat gagctgattt tcctgaaaca   12540
ctaaagagaa atgtcttttg tgctacagtt tcgtagcatg agtttaaatc aagattatga   12600
tgagtaaatg tgtatgggtt aaatcaaaga taaggttata gtaacatcaa agattaggtg   12660
aggtttatag aaagatagat atccaggctt accaaagtat taagtcaaga atataatatg   12720
tgatcagctt tcaaagcatt tacaagtgct gcaagttagt gaaacagctg tctccgtaaa   12780
tggaggaaat gtgggaagc cttggaatgc ccttctggtt ctggcacatt ggaaagcaca   12840
ctcagaaggc ttcatcacca agattttggg agagtaaagc taagtatagt tgatgtaaca   12900
ttgtagaagc agcataggaa caataagaac aataggtaaa gctataatta tggcttatat   12960
ttagaaatga ctgcatttga tattttagga tattttcta ggttttttcc tttcatttta    13020
ttctcttcta gttttgacat tttatgatag atttgctctc tagaaggaaa cgtctttatt   13080
taggagggca aaaattttgg tcatagcatt cacttttgct attccaatct acaactggaa   13140
```

| | |
|---|---:|
| gatacataaa agtgctttgc attgaatttg ggataacttc aaaaatccca tggttgttgt | 13200 |
| tagggatagt actaagcatt tcagttccag gagaataaaa gaaattccta tttgaaatga | 13260 |
| attcctcatt tggaggaaaa aaagcatgca ttctagcaca acaagatgaa attatggaat | 13320 |
| acaaaagtgg ctccttccca tgtgcagtcc ctgtccccc cgccagtcc tccacaccca | 13380 |
| aactgtttct gattggcttt tagctttttg ttgttttttt ttttccttct aacacttgta | 13440 |
| tttggaggct cttctgtgat tttgagaagt atactcttga gtgtttaata aagtttttt | 13500 |
| ccaaaagta | 13509 |

<210> SEQ ID NO 9
<211> LENGTH: 4130
<212> TYPE: DNA
<213> ORGANISM: Homo sapiens

<400> SEQUENCE: 9

| | |
|---|---:|
| gggggcacgt ctcggcgagt cacgatgatg gcggccacca tcctgtggtg agctagcgga | 60 |
| ttccctgctt gtctcgccga ccccctcgcg ccttctgcag actccgtggc tggcgctcgg | 120 |
| cgcgtgagga agcacggcgg cccgagttcg cggggaaggc cgcagtcgcg gaggcagcgg | 180 |
| cgcggtccgg ggcacgggct gggggagagg ccgctccgct gggcgaatgt gacaagcccc | 240 |
| cacccccacc gccttcctcc ccagagcgcg aggagcgcgg gcgacccgg ggccccgcca | 300 |
| ggccacagac cccgcccagc ggccagcacc cggcgcaggc ccggcagccg agctgcgcg | 360 |
| cggcaccatg caggtcaccc tgaagaccct ccagcagcag accttcaaga tagacattga | 420 |
| ccccgaggag acgtgaaaag cactgaaaga gaagattgaa tctgaaaagg ggaaagatgc | 480 |
| ctttccagta gcaggtcaaa aattaattta tgcaggcaaa atcctcaatg atgatactgc | 540 |
| tctcaaagaa tataaaattg atgagaaaaa ctttgtggtg gttatggtga ccaaacccaa | 600 |
| agcagtgtcc acaccagcac cagctacaac tcagcagtca gctcctgcca gcactacagc | 660 |
| agttacttcc tccaccacca caactgtggc tcaggctcca accctgtcc ctgccttggc | 720 |
| ccccacttcc acacctgcat ccatcactcc agcatcagcg acagcatctt ctgaacctgc | 780 |
| acctgctagt gcagctaaac aagagaagcc tgcagaaaag ccagcagaga caccagtggc | 840 |
| tactagccca acagcaactg acagtacatc gggtgattct tctcggtcaa acctttttga | 900 |
| agatgcaacg agtgcacttg tgacgggtca gtcttacgag aatatggtaa ctgagatcat | 960 |
| gtcaatgggc tatgaacgag agcaagtaat tgcagccctg agagccagtt tcaacaaccc | 1020 |
| tgacagagca gtggagtatc ttttaatggg aatccctgga gatagagaaa gtcaggctgt | 1080 |
| ggttgacccc cctcaagcag ctagtactgg ggctcctcag tcttcagcag tggctgcagc | 1140 |
| tgcagcaact acgacagcaa caactacaac aacaagttct ggaggacatc cccttgaatt | 1200 |
| tttacggaat cagcctcagt ttcaacagat gagacaaatt attcagcaga atccttcctt | 1260 |
| gcttccagcg ttactacagc agataggtcg agagaatcct caattacttc agcaaattag | 1320 |
| ccaacaccag gagcatttta ttcagatgtt aaatgaacca gttcaagaag ctggtggtca | 1380 |
| aggaggagga ggtggaggtg gcagtggagg aattgcagaa gctggaagtg gtcatatgaa | 1440 |
| ctacattcaa gtaacacctc aggaaaaaga agctatagaa aggttaaagg cattaggatt | 1500 |
| tcctgaagga cttgtgatac aagcgtattt tgcttgtgag aagaatgaga atttggctgc | 1560 |
| caatttctctt ctacagcaga actttgatga agattgaaag ggactttttt atatctcaca | 1620 |
| cttcacacca gtgcattaca ctaacttgtt cactggattg tctgggatga cttgggctca | 1680 |
| tatccacaat acttggtata aggtagtaga ttgttggggg tggggaggga gggatctagg | 1740 |

```
atacagggca gggataaata cagtgcatgt ctgcttcaat tagcagatgc cgcaactcca   1800
cacagtgtgt aaaatatata caaccaaaaa tcagcttttg caggtcttta tttcttctgt   1860
aaaacagtag gtaacttttc ctaggtttca ctcttttag tgtactagat ccagaaactt    1920
agtgtaatgc cctgctttat atttctttga cttaacattg gtttcagaaa gaatcttagc   1980
tacctagaat ttacagtctc tgtttcatgg caacactgga taatggcttt gtgaaattta   2040
aaaaatttt gtagcgactg taaacagaaa tgccaaattg atggttaatt gttgctgctt    2100
caaaaataag tataaaatta atatgtaagg aagcccattc tttcatgtta aatacttggg   2160
gtgggagggg agaaagggaa ccttttctta aaatgaaaat aattactgct attttaaaat   2220
ttcttgatca ttgaatgtga gacccttcta acatgatttg agaagctgta caagtatagg   2280
cagagttatt ttcctgttta cattttttt ttgttttggg gaaaaaattg gtaggtgtct    2340
aattactgtt tacttcattg ttatattgca gtaaaagttt taaaacaacc attgcatgtt   2400
tgcttttgat gtatcccttt gtgaaattag cacttttggg gccaatggag aaatgcagca   2460
ttcactctcc ctgtcttttc cccttccctc agcagaaacg tgtttatcag caagtcgtga   2520
gtcaaactgc tgccttttaa aaacccaca aaatgctgat tcagttcaaa attaatgcaa    2580
atgtttcaaa actgggtttc tgatatttgt aaatgtgttt ctttattaga taagagtgta   2640
ttaccattaa agtcattagt ataatattgc tttcaaaaag aaatggtaga caaaactata   2700
atccagcatc ttttattgca ttggaaagac tggcaaagtc ttttggatgg gttgggagat   2760
gtggctggaa agtactttgg aaaatataca atcaagatat ctcatggcat attaaaagaa   2820
aaatcttaat agcagtgttg gcttttattt ggattttttc atctcagttt tttctgtgga   2880
atctccttca ttggcattgt tatttaatca taaacggggc agatgtctac ttgttcagtt   2940
tttcaaatct gttttcctga gtataaataa gagtatttaa agaaataatt tggattgctt   3000
ttgtttttg tttccttttt tttaaccatc tgatactaag aagatgaatt tgcacagatt    3060
tctctgcata atttctcaat atctttagca cagtatggtg atgatgactt ttaagcattt   3120
acatcacgta ctcataacct attatgaaaa taaatgaaac tggctgggta tggtggctca   3180
tgcctataat cccagcactt tgggaggccg aggtgggcag atcacttgag gccaggagat   3240
tgagaccagc ctgaccgtca tggcgaaacc ccgtctatac taaaaataca aaaaatagcc   3300
aggcatggtg gcgcacgcct gtggtcccag ctacttggga ggctgaggca tgagaattgc   3360
ttgaacccgg gaagtgaagg ttgccgtgag ctgagatcac accactgcca taaacatgac   3420
aggcttttgg actttgtatt acctgtatgt tttataatgg atcatgcata atttctcagg   3480
agaataaaat gagaattcat atatacgttc atctttcaag tcagagcaat gagttgggaa   3540
aagaggtggc atttctgatc ggataatgga atactctcat ttattttatg acattctctg   3600
tctactcaga tcatagtgaa aactggaaac aaaaaaaaaa aacagcctct tcttggaaag   3660
tgacagcaga aggtggcatg gagcttgtgt ccttggacaa caaatctgga tatactagga   3720
ttaattatca gaagacagct caggccaagt tttgatcgtt ccatacagta ccttgtttat   3780
ctgcttctta aagaatcagc cgagacacca taaagaaat aggctttttg tgccttttgc    3840
tgttaatgtt taatttacaa actgttttgg taaatctctt aatgtaagta gctatttgac   3900
tttggaattt tgcattcgag gtatactgtc atttcttgaa atctttttct cgtttagttg   3960
ctctgtggga aatgtgagga agcctaagtt tgtatttgta aatttcttat gccatcctct   4020
agtcaaattt ttttcattg tttaaaaata cggaagtgtt ccaatataat ttttcctgt     4080
```

-continued

```
actggatggc taggattcta gagaattgat tataaaatat tttcaataca      4130
```

<210> SEQ ID NO 10
<211> LENGTH: 3164
<212> TYPE: DNA
<213> ORGANISM: Homo sapiens

<400> SEQUENCE: 10

```
gatacgacgg cagcgcggcg ggaggttcga ttgacccggt cttggcgggt cggtgagtct     60
tggcggctgt taacgcgcgc tttgggaaca ggaaggttga gagagaggtg ctggggtctg    120
cgtctatctc tgtcgctctt ttcagcccct cctggtattc ccctcctaac ctgggttttt    180
tacacgcccg cgtggcttcc tgctcgacct ccctgagtct gatcctggtt tccacctcca    240
gccctgggaa atttcctttc tccagactcg ccctccccac ccgggcctcg gactttcacc    300
ccagcttctc tctcctggcc agtgattacc caccccaat cccaccccgc ccgccgcgc     360
aactacctcc tcccttcacc cggactggga ccatcatccc cactccactc cgcccagtct    420
gggactccac ctgcctcctc cccaatccca cactaatctc tgcttggtct cttcctcttt    480
ggcctaatct ctcgtctcgg cttattgggg acggccactc tcacagtttg gttccaaaca    540
ccagttcctg gatggattcc cgccatccat gcccctctt taattagccg gtcctctcaa    600
taatgtagca gccccctcta cagattagac cctggtccta cactcttagc cgctgcctgc    660
ttttgacctt tggctcatgg gtacttgacg ttttaaactc ctaggcccag gatgaggagg    720
agcttggctc ccagccagct ggccaagaga aaacctgaag gcaggtcctg tgatgatgaa    780
gactggcaac ctggcctagt gactcctagg aaacggaaat ccagcagtga cccagatc      840
caggagtgtt tcctgtctcc ttttcggaaa cctttgagtc agctaaccaa tcaaccacct    900
tgtctggaca gcagtcagca tgaagcattt attcgaagca ttttgtcaaa gcctttcaaa    960
gtccccattc caaattatca aggtcctctg ggctctcgag cattgggcct gaaaagggct   1020
ggggtccgcc gggcccctcca tgaccccctg gaaaaagatg ccttggttct gtatgagcct   1080
cccccgctga gcgctcatga ccagctgaag cttgacaagg agaaactccc tgtccatgtg   1140
gttgttgacc ctattctcag taaggttttg cggcctcatc agagagaggg agtgaaattc   1200
ctgtgggagt gtgtcaccag tcggcgcatc cctggcagcc atggctgcat catggctgat   1260
gagatgggcc taggaaagac gctgcagtgc atcacattga tgtggacact tttacgccag   1320
agtccagagt gcaagccaga aattgacaag gcagtggtgg tgtcgccttc cagcctggtg   1380
aagaactggt acaatgaggt tgggaaatgg ctcggaggga ggatccaacc tctggccatc   1440
gatggaggat ctaaggatga aatagaccaa aagctggaag gattcatgaa ccagcgtgga   1500
gccagggtgt cttctcccat cctcatcatt tcctatgaga ccttccgcct tcatgttgga   1560
gtcctccaga aaggaagtgt tggtctggtc atatgtgacg agggacacag gctcaagaac   1620
tctgagaatc agacttacca agccctggac agcttgaaca ccagccggcg ggtgctcatc   1680
tccggaactc ccatccagaa tgatctgctt gagtatttca gcttggtaca ttttgttaat   1740
tccggcatcc tagggactgc ccatgaattc aagaagcatt tgaattgcc aattttgaag    1800
ggtcgagacg ctgctgctag tgaggcagac aggcagctag gagaggagcg gctgcgggag   1860
ctcaccagca ttgtgaatag atgcctgata cggaggactt ctgatatcct ttctaaatat   1920
ctgcctgtga agattgagca ggtcgtttgt gtaggctgac caccccttca gactgagtta   1980
tacaagaggt ttctgagaca agccaaaccg gcagaagaat tgcttgaggg caagatgagt   2040
gtgtcttccc tttcttccat cacctcgcta aagaagcttt gtaatcatcc agctctaatc   2100
-continued
tatgataagt gtgtggaaga ggaggatggc tttgtgggtg ccttggacct cttccctcct 2160
ggttacagct ctaaggccct ggagccccag ctgtcaggta agatgctggt cctggattat 2220
attctggcgg tgacccgaag ccgtagcagt gacaaagtag tgctggtgtc gaattacacc 2280
cagactttgg atctctttga gaagctgtgc cgtgcccgaa ggtacttata cgtccgcctg 2340
gatggcacga tgtccattaa gaagcgagcc aaggttgtag aacgcttcaa tagtccatcg 2400
agccctgact ttgtcttcat gctgagcagc aaagctgggg gctgtggcct caatctcatt 2460
ggggctaacc ggctggtcat gtttgaccct gactggaacc cagccaatga tgaacaagcc 2520
atggcccggg tctggcgaga tggtcaaaag aagacttgct atatctaccg cctgctgtct 2580
gcagggacca ttgaggagaa gatcttccag cgtcagagcc acaagaaggc actgagcagc 2640
tgtgtggtgg atgaggagca ggatgtagag cgccacttct ctctgggcga gttgaaggag 2700
ctgtttatcc tggatgaagc tagcctcagt gacacacatg acaggttgca ctgccgacgt 2760
tgtgtcaaca gccgtcagat ccggccaccc cctgatggtt ctgactgcac ttcagacctg 2820
gcagggtgga accactgcac tgataagtgg gggctccggg atgaggtact ccaggctgcc 2880
tgggatgctg cctccactgc catcaccttc gtcttccacc agcgttctca tgaggagcag 2940
cggggcctcc gctgataacc agctggtctg ggtgtagctc ttagaggaag gagataggga 3000
aaaggggctc cttgctccac agggccctgt tgaattttgt tctctgggag aaaatcatca 3060
agaagggctg catgatgttt gcccaaaatt tattttataa gaaaaacttt tttggttaaa 3120
aaaaagaata aaggtatgaa agggttaaaa aaaaaaaaaa aaaa 3164

<210> SEQ ID NO 11
<211> LENGTH: 57
<212> TYPE: RNA
<213> ORGANISM: Artificial Sequence
<220> FEATURE:
<223> OTHER INFORMATION: Description of Artificial Sequence: Synthetic
oligonucleotide
<400> SEQUENCE: 11
gggaggacga ugcggaucag ccauguuuac gucacuccuu gucaauccuc aucggcu 57

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
primer
<400> SEQUENCE: 12
agaaggcggc ttacctgagt 20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
primer
<400> SEQUENCE: 13
gacattttg tcagccaatc ttt 23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgcggtttt tgtcagctta                                              20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggtcctaaa tctgctttgt tgc                                          23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggatccagc tatttggttt ga                                           22

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccaagtatgt aaccaacaat agaagaagta g                                 31

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgagttcctg gaggtggctg tgcatc                                       26

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttgacgcag tgcagcgtgt cctggata                                     28

<210> SEQ ID NO 20
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 20
atggtagaca aaactataat ccagcatc                                          28

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gccacatctc ccaaccca                                                     18

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atggaggcca tatttccatg ac                                                22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caagcagcca gaacttggaa g                                                 21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgaagccgta gcagtgacaa ag                                                22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atggacatcg tgccatccag                                                   20

<210> SEQ ID NO 26
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
tcgctctctg ctcctcctgt tc                                            22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcccaatac gaccaaatcc                                               20

<210> SEQ ID NO 28
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
taatacgact cactataggg aggacgatgc ggatcagcca tgtttacgtc actccttgtc    60
aatcctcatc ggc                                                      73

<210> SEQ ID NO 29
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aattctccga acgtgtcacg tcaagcttca tacgtgacac gttcggagaa ttgccgatga    60
ggattgacaa g                                                        71

<210> SEQ ID NO 30
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttcggctaac tcgccagttt acaagcttca ttaaactggc gagttagccg aagccgatga    60
ggattgacaa g                                                        71

<210> SEQ ID NO 31
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caggacacaa ttacaactaa acaagcttca ttttagttgt aattgtgtcc tggccgatga    60
```

```
ggattgacaa g                                                          71

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggctattca gtgtgcgaga caagcttcat tctcgcacac tgaatagcct tgccgatgag    60
gattgacaag                                                           70

<210> SEQ ID NO 33
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
taatacgact cactatacag gcatgcctag ctaagcagcc catggcttat gcgcggaata    60
ttggcttccg ttc                                                       73

<210> SEQ ID NO 34
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcggctaac tcgccagttt acaagcttca ttaaactggc gagttagccg aagaacggaa    60
gccaatattc c                                                         71

<210> SEQ ID NO 35
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caggacacaa ttacaactaa acaagcttca ttttagttgt aattgtgtcc tggaacggaa    60
gccaatattc c                                                         71

<210> SEQ ID NO 36
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaggctattc agtgtgcgag acaagcttca ttctcgcaca ctgaatagcc ttgaacggaa    60
gccaatattc c                                                         71

<210> SEQ ID NO 37
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
taatacgact cactataggg aggacgatgc gg                                    32

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aattctccga acgtgtcacg tcaagc                                           26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttcggctaac tcgccagttt acaagc                                           26

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
taatacgact cactatacag gcatgcctag ct                                    32

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caggacacaa ttacaactaa acaagc                                           26

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaggctattc agtgtgcgag acaagc                                           26

<210> SEQ ID NO 43
<211> LENGTH: 108
```

```
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 43
gggaggacga ugcggaucag ccauguuuac gucacuccuu gucaauccuc aucggcaauu    60
cuccgaacgu gucacguaug aagcuugacg ugacacguuc ggagaauu                108

<210> SEQ ID NO 44
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 44
gggaggacga ugcggaucag ccauguuuac gucacuccuu gucaauccuc aucggcuucg    60
gcuaacucgc caguuuaaug aagcuuguaa acuggcgagu uagccgaa                108

<210> SEQ ID NO 45
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 45
gggaggacga ugcggaucag ccauguuuac gucacuccuu gucaauccuc aucggccagg    60
acacaauuac aacuaaaaug aagcuuguuu aguugaauu guguccug                 108

<210> SEQ ID NO 46
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 46
gggaggacga ugcggaucag ccauguuuac gucacuccuu gucaauccuc aucggcaagg    60
cuauucagug ugcgagaaug aagcuugucu cgcacacuga auagccuu                108

<210> SEQ ID NO 47
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47
caggcaugcc uagcuaagca gcccauggcu uaugcgcgga auauuggcuu ccguucuucg    60
gcuaacucgc caguuuaaug aagcuuguaa acuggcgagu uagccgaa                108

<210> SEQ ID NO 48
<211> LENGTH: 108
<212> TYPE: RNA
<213> ORGANISM: Artificial Sequence
<220> FEATURE:
<223> OTHER INFORMATION: Description of Artificial Sequence: Synthetic
```

```
                  polynucleotide

<400> SEQUENCE: 48
caggcaugcc uagcuaagca gcccauggcu uaugcgcgga auauuggcuu ccguuccagg      60
acacaauuac aacuaaaaug aagcuuguuu aguuguaauu guguccug                  108

<210> SEQ ID NO 49
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 49
caggcaugcc uagcuaagca gcccauggcu uaugcgcgga auauuggcuu ccguucaagg      60
cuauucagug ugcgagaaug aagcuugucu cgcacacuga auagccuu                  108

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uucggcuaac ucgccaguuu a                                                21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaaacuggcg aguuagccga a                                                21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
caggacacaa uuacaacuaa a                                                21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuuaguugua auuguguccu g                                                21

<210> SEQ ID NO 54
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 54
aaggcuauuc agugugcgag a                                                   21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ucucgcacac ugaauagccu u                                                   21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
aauucuccga acgugucacg u                                                   21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
acgugacacg uucggagaau u                                                   21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
ttcggctaac tcgccagttt a                                                   21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
aattctccga acgtgtcacg t                                                   21

<210> SEQ ID NO 60
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 60
gagggctcct tgacaaacac atccat                                          26

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctctagagcg actggagcac gaggacacta                                      30

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggaaggcccg gagtgcgtgt accat                                           25

<210> SEQ ID NO 63
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gggaggacga ugcggaucag ccauguuuac gucacuccuu gucaauccuc aucggc         56

<210> SEQ ID NO 64
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uaaacuggcg aguuagccga auu                                             23

<210> SEQ ID NO 65
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uucggcuaac ucgccaguuu agccgaugag gauu                                 34
```

RADIATION SENSITIZATION AGENTS FOR PROSTATE CANCER

CROSS-REFERENCE TO RELATED APPLICATIONS

This application is a 35 U.S.C. §371 U.S. national stage entry of International Application PCT/US2011/044997 (WO 2012/012710) having an International filing date of Jul. 22, 2011 which claims the benefit of the following U.S. Provisional Application No. 61/366,734, filed Jul. 22, 2010, the entire contents of which are incorporated herein by reference.

STATEMENT OF RIGHTS TO INVENTIONS MADE UNDER FEDERALLY SPONSORED RESEARCH

This work was supported by the following grant from the National Institutes of Health, Grant No: 5P50CA058236-15. The government has certain rights in the invention.

BACKGROUND OF THE INVENTION

An estimated 1 in 6 men will be diagnosed with prostate cancer (PCa). Although the majority of these men can be successfully treated with surgery or radiation therapy, approximately 20%-40% will biochemically recur within 10 years of treatment. This risk of recurrence is elevated to approximately 50% for men with locally advanced disease, a condition that is primarily managed by radiation therapy. Thus, there is a need for new technologies that improve the therapeutic index of radiation therapy for local disease because these will significantly decrease the morbidity and mortality of PCa.

SUMMARY OF THE INVENTION

As described below, the present invention features aptamer-inhibitory nucleic acid molecules that radiosensitize neoplastic cells expressing tumor antigens that bind the aptamer and methods of using aptamer-inhibitory nucleic acid molecules to radiosensitize neoplastic cells.

In one aspect, the invention generally features a method of sensitizing a neoplastic cell to ionizing radiation, the method involving contacting the neoplastic cell with an effective amount of an aptamer-inhibitory nucleic acid chimera.

In another aspect, the invention generally features a method of inducing cell death or terminal differentiation in a neoplastic cell, the method involving contacting the neoplastic cell with an effective amount of an aptamer-inhibitory nucleic acid chimera, and exposing the neoplastic cell to ionizing radiation.

In another aspect, the invention features a method of reducing the growth, proliferation or survival of a neoplastic cell, the method involving contacting the neoplastic cell with an effective amount of an aptamer-inhibitory nucleic acid chimera, and exposing the neoplastic cell to ionizing radiation.

In yet another aspect, the invention features a method of treating neoplasia in a subject involving administering an aptamer-inhibitory nucleic acid chimera to the subject; and exposing the neoplasia to ionizing radiation, thereby treating neoplasia in the subject.

In yet another aspect, the invention features a method of treating prostate cancer in a subject in need thereof involving administering an aptamer-shRNA chimera to the subject, wherein the aptamer-shRNA chimera specifically binds prostate-specific membrane antigen (PSMA), and wherein the shRNA decreases the expression of ACLY, BRCA2, DNMT1, LDHA, MAD2L2, NBN, NONO, DNAPK, RAD23B, or RAD54L; and exposing the subject to ionizing radiation, thereby treating prostate cancer in the subject.

In yet another aspect, the invention features a method of inhibiting angiogenesis in a neoplasia, the method involving contacting neovascular endothelia cells with an effective amount of an aptamer-inhibitory nucleic acid chimera, and exposing the neovascular endothelia cells to ionizing radiation.

In yet another aspect, the invention generally features an oligonucleotide containing an aptamer covalently linked to an shRNA.

In various embodiments of any of the above aspects or any other aspect of the invention delinated herein, the neoplastic cell is in a subject. In another embodiment the inhibitory nucleic acid is selected from the group consisting of shRNA, siRNA, and ribozyme. In further embodiments the inhibitory nucleic acid is siRNA. In other embodiments the aptamer-inhibitory nucleic acid chimera decreases the expression of a target gene. In another embodiment the target gene encodes a DNA repair protein. In yet another embodiment the target gene is selected from the group consisting of ACLY, BRCA2, DNMT1, LDHA, MAD2L2, NBN, NONO, DNAPK, RAD23B, and RAD54L. In further embodiments decreasing the expression of the target gene sensitizes the neoplastic cell to ionizing radiation. In other embodiments the aptamer-inhibitory nucleic acid chimera specifically binds a cell surface molecule. In another embodiment the cell surface molecule is a tumor antigen. In yet another embodiment the tumor antigen is selected from Muc1, HER2, TGFbeta-receptor, Guanylyl Cyclase C (GC-C), PCSA, or prostate-specific membrane antigen (PSMA). In further embodiments the tumor antigen is prostate-specific membrane antigen (PSMA). In other embodiments the aptamer-inhibitory nucleic acid chimera comprises A10-3. In another embodiment the aptamer-inhibitory nucleic acid chimera comprises modified nucleotides. In further embodiments the modified nucleotides are selected from 2'-fluoro-modified pyrimidines, locked-nucleic acids (LNAs), 2'-O-methyl-modified nucleotides, and 2'-amino-modified nucleotides. In other embodiments the modified nucleotides comprise 2'-fluoro-modified pyrimidines. In another embodiment the method is carried out in vivo. In yet another embodiment the aptamer-inhibitory nucleic acid chimera is selected from any of the aptamer-inhibitory nucleic acid chimeras of Table 4. In further embodiments the neoplastic cell is in a subject diagnosed as having a neoplasia selected from the group consisting of prostate cancer, breast cancer, colon cancer, pancreatic cancer, and lung cancer. In other embodiments the method sensitizes the neoplasia to ionizing radiation. In another embodiment the subject is a mammal. In another embodiment the subject is a human.

Compositions and articles defined by the invention were isolated or otherwise manufactured in connection with the examples provided below. Other features and advantages of the invention will be apparent from the detailed description, and from the claims.

Definitions

By "aptamer" is meant an oligonucleotide that is capable of forming a complex with an intended target substance. The complexation is target-specific in the sense that other materials which may accompany the target do not complex to the aptamer. It is recognized that complexation and affinity are a matter of degree; however, in this context, "target-specific"

means that the aptamer binds to target with a much higher degree of affinity than it binds to contaminating materials. The meaning of specificity in this context is thus similar to the meaning of specificity as applied to antibodies, for example.

By "small hairpin RNA" or "shRNA" is meant an oligonucleotide that consists of a stem-loop structure with optional 3' UU-overhangs. While there may be variation, stems can range from 19 to 31 bp (desirably 25 to 29 bp), and the loops can range from 4 to 30 bp (desirably 4 to 23 bp).

By "aptamer-shRNA chimera" is meant an oligonucleotide that comprises an aptamer covalently linked to an shRNA such that the aptamer retains its ability to bind to its cognate target molecule, and the shRNA is properly processed by the cell to act as an siRNA that inhibits the expression of a target protein.

By "ACLY" is meant a gene that transcribes an RNA having at least 85% nucleotide sequence identity to NM_001096 or NM_198830. An exemplary ACLY sequence is provided below:

```
                                                                      (SEQ ID NO: 1)
   1 agccgatggg ggcggggaaa agtccggctg ggccgggaca aaagccggat cccgggaagc
  61 taccggctgc tggggtgctc cggattttgc ggggttcgtc gggcctgtgg aagaagcgcc
 121 gcgcacggac ttcggcagag gtagagcagg tctctctgca gccatgtcgg ccaaggcaat
 181 ttcagagcag acgggcaaag aactccttta caagttcatc tgtaccacct cagccatcca
 241 gaatcggttc aagtatgctc gggtcactcc tgacacagac tgggcccgct tgctgcagga
 301 ccaccctgg ctgctcagcc agaacttggt agtcaagcca gaccagctga tcaaacgtcg
 361 tggaaaactt ggtctcgttg gggtcaacct cactctggat ggggtcaagt cctggctgaa
 421 gccacggctg ggacaggaag ccacagttgg caaggccaca ggcttcctca agaacttggt
 481 gatcgagccc ttcgtccccc acagtcaggc tgaggagttc tatgtctgca tctatgccac
 541 ccgagaaggg gactacgtcc tgttccacca cgaggggggt gtggacgtgg tgatgtgga
 601 cgccaaggcc cagaagctgc ttgttggcgt ggatgagaaa ctgaatcctg aggacatcaa
 661 aaaacacctg ttggtccacg cccctgaaga caagaaagaa attctggcca gttttatctc
 721 cggcctcttc aatttctacg aggacttgta cttcacctac ctcgagatca atcccttgt
 781 agtgaccaaa gatggagtct atgtccttga cttggcgcc aaggtggacg ccactgccga
 841 ctacatctgc aaagtgaagt ggggtgacat cgagttccct ccccccttcg ggcgggaggc
 901 atatccagag gaagcctaca ttgcagacct cgatgccaaa agtggggcaa gcctgaagct
 961 gaccttgctg aaccccaaag ggaggatctg gaccatggtg gccgggggtg gcgcctctgt
1021 cgtgtacagc gataccatct gtgatctagg gggtgtcaac gagctggcaa actatgggga
1081 gtactcaggc gccccagcg agcagcagac ctatgactat gccaagacta tcctctccct
1141 catgacccga gagaagcacc cagatggcaa gatcctcatc attggaggca gcatcgcaaa
1201 cttcaccaac gtggctgcca cgttcaaggg catcgtgaga gcaattcgag attaccaggg
1261 ccccctgaag gagcacgaag tcacaatctt tgtccgaaga ggtggcccca actatcagga
1321 gggcttacgg gtgatgggag aagtcgggaa gaccactggg atccccatcc atgtctttgg
1381 cacagagact cacatgacgg ccattgtggg catggccctg ggccaccggc ccatcccaa
1441 ccagccaccc acagcggccc acactgcaaa cttcctcctc aacgccagcg ggagcacatc
1501 gacgccagcc cccagcagga cagcatcttt ttctgagtcc agggccgatg aggtggcgcc
1561 tgcaaagaag gccaagcctg ccatgccaca agattcagtc ccaagtccaa gatccctgca
1621 aggaaagagc accaccctct tcagccgcca caccaaggcc attgtgtggg gcatgcagac
1681 ccgggccgtg caaggcatgc tggactttga ctatgtctgc tcccgagacg agccctcagt
1741 ggctgccatg gtctacccctt tcactgggga ccacaagcag aagtttact gggggcacaa
1801 agagatcctg atccctgtct tcaagaacat ggctgatgcc atgaggaagc atccggaggt
1861 agatgtgctc atcaactttg cctctctccg ctctgcctat gacagcacca tggagaccat
1921 gaactatgcc cagatccgga ccatcgccat catagctgaa ggcatccctg aggccctcac
1981 gagaaagctg atcaagaagg cggaccagaa gggagtgacc atcatcggac ctgccactgt
```

-continued

```
2041 tggaggcatc aagcctgggt gctttaagat tggcaacaca ggtgggatgc tggacaacat
2101 cctggcctcc aaactgtacc gcccaggcag cgtggcctat gtctcacgtt ccggaggcat
2161 gtccaacgag ctcaacaata tcatctctcg gaccacggat ggcgtctatg agggcgtggc
2221 cattggtggg gacaggtacc cgggctccac attcatggat catgtgttac gctatcagga
2281 cactccagga gtcaaaatga ttgtggttct tggagagatt gggggcactg aggaatataa
2341 gatttgccgg ggcatcaagg agggccgcct cactaagccc atcgtctgct ggtgcatcgg
2401 gacgtgtgcc accatgttct cctctgaggt ccagtttggc catgctggag cttgtgccaa
2461 ccaggcttct gaaactgcag tagccaagaa ccaggctttg aaggaagcag gagtgtttgt
2521 gccccggagc tttgatgagc ttggagagat catccagtct gtatacgaag atctcgtggc
2581 caatggagtc attgtacctg cccaggaggt gccgccccca accgtgccca tggactactc
2641 ctgggccagg gagcttggtt tgatccgcaa acctgcctcg ttcatgacca gcatctgcga
2701 tgagcgagga caggagctca tctacgcggg catgcccatc actgaggtct tcaaggaaga
2761 gatgggcatt ggcggggtcc tcggcctcct ctggttccag aaaaggttgc ctaagtactc
2821 ttgccagttc attgagatgt gtctgatggt gacagctgat cacgggccag ccgtctctgg
2881 agcccacaac accatcattt gtgcgcgagc tgggaaagac ctggtctcca gcctcacctc
2941 ggggctgctc accatcgggg atcggtttgg gggtgccttg gatgcagcag ccaagatgtt
3001 cagtaaagcc tttgacagtg gcattatccc catggagttt gtgaacaaga tgaagaagga
3061 agggaagctg atcatgggca ttggtcaccg agtgaagtcg ataaacaacc cagacatgcg
3121 agtgcagatc ctcaaagatt acgtcaggca gcacttccct gccactcctc tgctcgatta
3181 tgcactggaa gtagagaaga ttaccacctc gaagaagcca aatcttatcc tgaatgtaga
3241 tggtctcatc ggagtcgcat ttgtagacat gcttagaaac tgtgggtcct tactcgggga
3301 ggaagctgat gaatatattg acattggagc cctcaatggc atctttgtgc tgggaaggag
3361 tatggggttc attggacact atcttgatca gaagaggctg aagcaggggc tgtatcgtca
3421 tccgtgggat gatatttcat atgttcttcc ggaacacatg agcatgtaac agagccagga
3481 accctactgc agtaaactga agacaagatc tcttccccca agaaaaagtg tacagacagc
3541 tggcagtgga gcctgcttta tttagcaggg gcctggaatg taaacagcca ctggggtaca
---- ggcaccgaag accaacatcc acaggctaac accccttcag tccacacaaa gaagcttcat
3661 attttttttta taagcataga aataaaaacc aagccaatat ttgtgacttt gctctgctac
3721 ctgctgtatt tattatatgg aagcatctaa gtactgtcag gatggggtct tcctcattgt
3781 agggcgttag gatgttgctt tcttttttcca ttagttaaac attttttttct cctttggagg
3841 aagggaatga acatttatg gcctcaagat actatacatt taaagcaccc caatgtctct
3901 ctttttttt ttttacttcc ctttcttctt cctatataa catgaagaac attgtattaa
3961 tctgattttt aaagatcttt ttgtatgtta cgtgttaagg gcttgtttgg tatcccactg
4021 aaatgttctg tgttgcagac cagagtctgt ttatgtcagg gggatggggc cattgcatcc
4081 ttagccattg tcacaaaata tgtggagtag taacttaata tgtaaagttg taacatacat
4141 acatttaaaa tggaaatgca gaaagctgtg aaatgtcttg tgtcttatgt tctctgtatt
4201 tatgcagctg atttgtctgt ctgtaactga agtgtgggtc caaggactcc taactacttt
4261 gcatctgtaa tccacaaaga ttctgggcag ctgccacctc agtctcttct ctgtattatc
4321 atagtctggt ttaaataaac tatatagtaa caaaaaaaaa
```

By "BRCA2" is meant a gene that transcribes an RNA having at least 85% nucleotide sequence identity to NM_000059. An exemplary BRCA2 sequence is provided below:

(SEQ ID NO: 2)

```
   1 gtggcgcgag cttctgaaac taggcggcag aggcggagcc gctgtggcac tgctgcgcct
  61 ctgctgcgcc tcgggtgtct ttttgcggcgg tgggtcgccg ccgggagaag cgtgagggga
 121 cagatttgtg accggcgcgg ttttttgtcag cttactccgg ccaaaaaaga actgcacctc
 181 tggagcggac ttatttacca agcattggag gaatatcgta ggtaaaaatg cctattggat
 241 ccaaagagag gccaacattt tttgaaattt ttaagacacg ctgcaacaaa gcagatttag
 301 gaccaataag tcttaattgg tctgaagaac tttcttcaga agctccaccc tataattctg
 361 aacctgcaga agaatctgaa cataaaaaca acaattacga accaaaccta tttaaaactc
 421 cacaaaggaa accatcttat aatcagctgg cttcaactcc aataatattc aaagagcaag
 481 ggctgactct gccgctgtac caatctcctg taaaagaatt agataaattc aaattagact
 541 taggaaggaa tgttcccaat agtagacata aaagtcttcg cacagtgaaa actaaaatgg
 601 atcaagcaga tgatgtttcc tgtccacttc taaattcttg tcttagtgaa agtcctgttg
 661 ttctacaatg tacacatgta acaccacaaa gagataagtc agtggtatgt gggagtttgt
 721 ttcatacacc aaagtttgtg aagggtcgtc agacaccaaa acatatttct gaaagtctag
 781 gagctgaggt ggatcctgat atgtcttggt caagttcttt agctacacca cccacccttta
 841 gttctactgt gctcatagtc agaaatgaag aagcatctga aactgtattt cctcatgata
 901 ctactgctaa tgtgaaaagc tattttttcca atcatgatga aagtctgaag aaaaatgata
 961 gatttatcgc ttctgtgaca gacagtgaaa acacaaatca aagagaagct gcaagtcatg
1021 gatttggaaa aacatcaggg aattcattta aagtaaatag ctgcaaagac cacattggaa
1081 agtcaatgcc aaatgtccta gaagatgaag tatatgaaac agttgtagat acctctgaag
1141 aagatagttt ttcattatgt ttttctaaat gtagaacaaa aaatctacaa aaagtaagaa
1201 ctagcaagac taggaaaaaa attttccatg aagcaaacgc tgatgaatgt gaaaaatcta
1261 aaaaccaagt gaaagaaaaa tactcatttg tatctgaagt ggaaccaaat gatactgatc
1321 cattagattc aaatgtagca aatcagaagc cctttgagag tggaagtgac aaaatctcca
1381 aggaagttgt accgtctttg gcctgtgaat ggtctcaact aaccctttca ggtctaaatg
1441 gagcccagat ggagaaaata cccctattgc atatttcttc atgtgaccaa aatatttcag
1501 aaaagacct attagacaca gagaacaaaa gaaagaaaga ttttcttact tcagagaatt
1561 ctttgccacg tatttctagc ctaccaaaat cagagaagcc attaaatgag gaaacagtgg
1621 taaataagag agatgaagag cagcatcttg aatctcatac agactgcatt cttgcagtaa
1681 agcaggcaat atctggaact tctccagtgg cttcttcatt tcagggtatc aaaaagtcta
1741 tattcagaat aagagaatca cctaaagaga ctttcaatgc aagttttttca ggtcatatga
1801 ctgatccaaa ctttaaaaaa gaaactgaag cctctgaaag tggactggaa atacatactg
1861 tttgctcaca gaaggaggac tccttatgtc caaatttaat tgataatgga agctggccag
1921 ccaccaccac acagaattct gtagctttga agaatgcagg tttaatatcc actttgaaaa
1981 agaaaacaaa taagtttatt tatgctatac atgatgaaac atcttataaa ggaaaaaaaa
2041 taccgaaaga ccaaaaatca gaactaatta actgttcagc ccagtttgaa gcaaatgctt
2101 ttgaagcacc acttacattt gcaaatgctg attcaggttt attgcattct tctgtgaaaa
2161 gaagctgttc acagaatgat tctgaagaac caactttgtc cttaactagc tcttttggga
```

-continued

```
2221 caattctgag gaaatgttct agaaatgaaa catgttctaa taatacagta atctctcagg
2281 atcttgatta taaagaagca aaatgtaata aggaaaaact acagttattg attaccccag
2341 aagctgattc tctgtcatgc ctgcaggaag gacagtgtga aaatgatcca aaaagcaaaa
2401 aagtttcaga tataaaagaa gaggtcttgg ctgcagcatg tcacccagta caacattcaa
2461 aagtggaata cagtgatact gactttcaat cccagaaaag tcttttatat gatcatgaaa
2521 atgccagcac tcttatttta actcctactt ccaaggatgt tctgtcaaac ctagtcatga
2581 tttctagagg caaagaatca tacaaaatgt cagacaagct caaaggtaac aattatgaat
2641 ctgatgttga attaaccaaa aatattccca tggaaaagaa tcaagatgta tgtgctttaa
2701 atgaaaatta taaaaacgtt gagctgttgc cacctgaaaa atacatgaga gtagcatcac
2761 cttcaagaaa ggtacaattc aaccaaaaca caaatctaag agtaatccaa aaaatcaag
2821 aagaaactac ttcaatttca aaaataactg tcaatccaga ctctgaagaa cttttctcag
2881 acaatgagaa taattttgtc ttccaagtag ctaatgaaag gaataatctt gctttaggaa
2941 atactaagga acttcatgaa acagacttga cttgtgtaaa cgaacccatt ttcaagaact
3001 ctaccatggt tttatatgga gacacaggtg ataaacaagc aacccaagtg tcaattaaaa
3061 aagatttggt ttatgttctt gcagaggaga acaaaaatag tgtaaagcag catataaaaa
3121 tgactctagg tcaagattta aaatcggaca tctccttgaa tatagataaa ataccagaaa
3181 aaaataatga ttacatgaac aaatgggcag gactcttagg tccaatttca aatcacagtt
3241 ttggaggtag cttcagaaca gcttcaaata aggaaatcaa gctctctgaa cataacatta
3301 agaagagcaa aatgttcttc aaagatattg aagaacaata tcctactagt ttagcttgtg
3361 ttgaaattgt aaataccttg gcattagata atcaaaagaa actgagcaag cctcagtcaa
3421 ttaatactgt atctgcacat ttacagagta gtgtagttgt ttctgattgt aaaaatagtc
3481 atataacccc tcagatgtta ttttccaagc aggattttaa ttcaaccat aatttaacac
3541 ctagccaaaa ggcagaaatt acagaacttt ctactatatt agaagaatca ggaagtcagt
3601 ttgaatttac tcagtttaga aaaccaagct acatattgca gaagagtaca tttgaagtgc
3661 ctgaaaacca gatgactatc ttaaagacca cttctgagga atgcagagat gctgatcttc
3721 atgtcataat gaatgcccca tcgattggtc aggtagacag cagcaagcaa tttgaaggta
3781 cagttgaaat taacggaagt tttgctggcc tgttgaaaaa tgactgtaac aaaagtgctt
3841 ctggttattt aacagatgaa aatgaagtgg ggtttagggg cttttattct gctcatggca
3901 caaaactgaa tgtttctact gaagctctgc aaaaagctgt gaaactgttt agtgatattg
3961 agaatattag tgaggaaact tctgcagagg tacatccaat aagtttatct tcaagtaaat
4021 gtcatgattc tgttgtttca atgtttaaga tagaaaatca taatgataaa actgtaagtg
4081 aaaaaaataa taaatgccaa ctgatattac aaaataatat tgaaatgact actggcactt
4141 ttgttgaaga aattactgaa aattacaaga gaaatactga aaatgaagat aacaaatata
4201 ctgctgccag tagaaattct cataacttag aatttgatgg cagtgattca agtaaaaatg
4261 atactgtttg tattcataaa gatgaaacgg acttgctatt tactgatcag cacaacatat
4321 gtcttaaatt atctggccag tttatgaagg agggaaacac tcagattaaa gaagatttgt
4381 cagatttaac ttttttggaa gttgcgaaag ctcaagaagc atgtcatggt aatacttcaa
4441 ataagaaca gttaactgct actaaaacgg agcaaaatat aaaagatttt gagacttctg
4501 atacatttt tcagactgca gtgggaaaa atattagtgt cgccaaagag tcatttaata
4561 aaattgtaaa tttctttgat cagaaaccag aagaattgca taactttcc ttaaattctg
4621 aattacattc tgacataaga aagaacaaaa tagaaattct aagttatgag gaaacagaca
```

-continued

```
4681  tagttaaaca caaaatactg aaagaaagtg tcccagttgg tactggaaat caactagtga
4741  ccttccaggg acaacccgaa cgtgatgaaa agatcaaaga acctactcta ttgggttttc
4801  atacagctag cgggaaaaaa gttaaaattg caaaggaatc tttggacaaa gtgaaaaacc
4861  tttttgatga aaaagagcaa ggtactagtg aaatcaccag ttttagccat caatgggcaa
4921  agaccctaaa gtacagagag gcctgtaaag accttgaatt agcatgtgag accattgaga
4981  tcacagctgc cccaaagtgt aaagaaatgc agaattctct caataatgat aaaaaccttg
5041  tttctattga gactgtggtg ccacctaagc tcttaagtga taatttatgt agacaaactg
5101  aaaatctcaa acatcaaaa agtatctttt tgaaagttaa agtcatgaa aatgtagaaa
5161  aagaaacagc aaaaagtcct gcaacttgtt acacaaatca gtccccttat tcagtcattg
5221  aaaattcagc cttagctttt tacacaagtt gtagtagaaa aacttctgtg agtcagactt
5281  cattacttga agcaaaaaaa tggcttagag aaggaatatt tgatggtcaa ccagaaagaa
5341  taaatactgc agattatgta ggaaattatt tgtatgaaaa taattcaaac agtactatag
5401  ctgaaaatga caaaaatcat ctctccgaaa aacaagatac ttatttaagt aacagtagca
5461  tgtctaacag ctattcctac cattctgatg aggtatataa tgattccagga tatctctcaa
5521  aaaataaact tgattctggt attgagccag tattgaagaa tgttgaagat caaaaaaaca
5581  ctagtttttc caaagtaata tccaatgtaa aagatgcaaa tgcatacccca caaactgtaa
5641  atgaagatat ttgcgttgag gaacttgtga ctagctcttc accctgcaaa aataaaaatg
5701  cagccattaa attgtccata tctaatagta ataattttga ggtagggcca cctgcattta
5761  ggatagccag tggtaaaatc gtttgtgttt cacatgaaac aattaaaaaa gtgaaagaca
5821  tatttacaga cagtttcagt aaagtaatta aggaaaacaa cgagaataaa tcaaaaattt
5881  gccaaacgaa aattatggca ggttgttacg aggcattgga tgattcagag gatattcttc
5941  ataactctct agataatgat gaatgtagca cgcattcaca taaggttttt gctgacattc
6001  agagtgaaga aattttacaa cataaccaaa atatgtctgg attggagaaa gtttctaaaa
6061  tatcaccttg tgatgttagt ttggaaactt cagatatatg taaatgtagt atagggaagc
6121  ttcataagtc agtctcatct gcaaatactt gtgggatttt tagcacagca agtggaaaat
----  ctgtccaggt atcagatgct tcattacaaa acgcaagaca agtgttttct gaaatagaag
6241  atagtaccaa gcaagtcttt tccaaagtat tgtttaaaag taacgaacat tcagaccagc
6301  tcacaagaga agaaaatact gctatacgta ctccagaaca tttaatatcc caaaaaggct
6361  tttcatataa tgtggtaaat tcatctgctt tctctggatt tagtacagca agtggaaagc
6421  aagtttccat tttagaaagt tccttacaca agttaagggg agtgttagag gaatttgatt
6481  taatcagaac tgagcatagt cttcactatt cacctacgtc tagacaaaat gtatcaaaaa
6541  tacttcctcg tgttgataag agaaacccag agcactgtgt aaactcagaa atggaaaaaa
6601  cctgcagtaa agaatttaaa ttatcaaata acttaaatgt tgaaggtggt tcttcagaaa
6661  ataatcactc tattaaagtt tctccatatc tctctcaatt tcaacaagac aaacaacagt
6721  tggtattagg aaccaaagtg tcacttgttg agaacattca tgttttggga aagaacagg
6781  cttcacctaa aaacgtaaaa atggaaattg gtaaaactga aactttttct gatgttcctg
6841  tgaaaacaaa tatagaagtt tgttctactt actccaaaga ttcagaaaac tactttgaaa
6901  cagaagcagt agaaattgct aaagctttta tggaagatga tgaactgaca gattctaaac
6961  tgccaagtca tgccacacat tctctttta catgtccga aaatgaggaa atggttttgt
7021  caaattcaag aattggaaaa agaagaggag agcccttat cttagtggga gaaccctcaa
```

-continued

```
7081 tcaaaagaaa cttattaaat gaatttgaca ggataataga aaatcaagaa aaatccttaa 7141 aggcttcaaa aagcactcca gatggcacaa taaaagatcg aagattgttt atgcatcatg 7201 tttctttaga gccgattacc tgtgtaccct ttcgcacaac taaggaacgt caagagatac 7261 agaatccaaa ttttaccgca cctggtcaag aatttctgtc taaatctcat ttgtatgaac 7321 atctgacttt ggaaaaatct tcaagcaatt tagcagtttc aggacatcca ttttatcaag 7381 tttctgctac aagaaatgaa aaaatgagac acttgattac tacaggcaga ccaaccaaag 7441 tctttgttcc accttttaaa actaaatcac attttcacag agttgaacag tgtgttagga 7501 atattaactt ggaggaaaac agacaaaagc aaaacattga tggacatggc tctgatgata 7561 gtaaaaataa gattaatgac aatgagattc atcagtttaa caaaaacaac tccaatcaag 7621 cagcagctgt aactttcaca aagtgtgaag aagaaccttt agatttaatt acaagtcttc 7681 agaatgccag agatatacag gatatgcgaa ttaagaagaa acaaaggcaa cgcgtctttc 7741 cacagccagg cagtctgtat cttgcaaaaa catccactct gcctcgaatc tctctgaaag 7801 cagcagtagg aggccaagtt ccctctgcgt gttctcataa acagctgtat acgtatggcg 7861 tttctaaaca ttgcataaaa attaacagca aaaatgcaga gtcttttcag tttcacactg 7921 aagattattt tggtaaggaa agtttatgga ctggaaaagg aatacagttg gctgatggtg 7981 gatggctcat accctccaat gatggaaagg ctggaaaaga gaattttat agggctctgt 8041 gtgacactcc aggtgtggat ccaaagctta tttctagaat ttgggtttat aatcactata 8101 gatggatcat atggaaactg gcagctatgg aatgtgcctt tcctaaggaa tttgctaata 8161 gatgcctaag cccagaaagg gtgcttcttc aactaaaata cagatatgat acggaaattg 8221 atagaagcag aagatcggct ataaaaaga taatggaaag ggatgacaca gctgcaaaaa 8281 cacttgttct ctgtgtttct gacataattt cattgagcgc aaatatatct gaaacttcta 8341 gcaataaaac tagtagtgca gatacccaaa aagtttccat tattgaactt acagatgggt 8401 ggtatgctgt taaggcccag ttagatcctc ccctcttagc tgtcttaaag aatggcagac 8461 tgacagttgg tcagaagatt attcttcatg gagcagaact ggtgggctct cctgatgcct 8521 gtacacctct tgaagcccca gaatctctta tgttaaagat ttctgctaac agtactcggc 8581 ctgctcgctg gtataccaaa cttggattct ttcctgaccc tagacctttt cctctgccct 8641 tatcatcgct tttcagtgat ggaggaaatg ttggttgtgt tgatgtaatt attcaaagag 8701 cataccctat acagtggatg gagaagacat catctggatt atacatattt cgcaatgaaa 8761 gagaggaaga aaaggaagca gcaaaatatg tggaggccca acaaaagaga ctagaagcct 8821 tattcactaa aattcaggag gaatttgaag aacatgaaga aaacacaaca aaaccatatt 8881 taccatcacg tgcactaaca agacagcaag ttcgtgcttt gcaagatggt gcagagcttt 8941 atgaagcagt gaagaatgca gcagacccag cttaccttga gggttatttc agttaagagc 9001 agttaagagc cttgaataat cacaggcaaa tgttgaatga taagaaacaa gctcagatcc 9061 agttggaaat taggaaggcc atggaatctg ctgaacaaaa ggaacaaggt ttatcaaggg 9121 atgtcacaac cgtgtggaag ttgcgtattg taagctattc aaaaaaagaa aaagattcag 9181 ttatactgag tatttggcgt ccatcatcag atttatattc tctgttaaca gaaggaaaga 9241 gatacagaat ttatcatctt gcaacttcaa aatctaaaag taaatctgaa agagctaaca 9301 tacagttagc agcgacaaaa aaaactcagt atcaacaact accggtttca gatgaaattt 9361 tatttcagat ttaccagcca cgggagcccc ttcacttcag caaattttta gatccagact 9421 ttcagccatc ttgttctgag gtggacctaa taggatttgt cgtttctgtt gtgaaaaaaa 9481 caggacttgc cccttttcgtc tatttgtcag acgaatgtta caatttactg gcaataaagt
```

-continued

```
 9541 tttggataga ccttaatgag gacattatta agcctcatat gttaattgct gcaagcaacc 9601 tccagtggcg accagaatcc aaatcaggcc ttcgtgcttt atttgctgga gattttctg 9661 tgttttctgc tagtccaaaa gagggccact ttcaagagac attcaacaaa atgaaaaata 9721 ctgttgagaa tattgacata ctttgcaatg aagcagaaaa caagcttatg catatactgc 9781 atgcaaatga tcccaagtgg tccaccccaa ctaaagactg tacttcaggg ccgtacactg ---- ctcaaatcat tcctggtaca ggaaacaagc ttctgatgtc ttctcctaat tgtgagatat 9901 attatcaaag tcctttatca ctttgtatgg ccaaaaggaa gtctgtttcc acacctgtct 9961 cagcccagat gacttcaaag tcttgtaaag gggagaaaga gattgatgac caaaagaact 10021 gcaaaaagag aagagccttg gatttcttga gtagactgcc tttacctcca cctgttagtc 10081 ccatttgtac atttgtttct ccggctgcac agaaggcatt tcagccacca aggagttgtg 10141 gcaccaaata cgaaacaccc ataaagaaaa aagaactgaa ttctcctcag atgactccat 10201 ttaaaaaatt caatgaaatt tctcttttgg aaagtaattc aatagctgac gaagaacttg 10261 cattgataaa tacccaagct cttttgtctg gttcaacagg agaaaaacaa tttatatctg 10321 tcagtgaatc cactaggact gctcccacca gttcagaaga ttatctcaga ctgaaacgac 10381 gttgtactac atctctgatc aaagaacagg agagttccca ggccagtacg gaagaatgtg 10441 agaaaaataa gcaggacaca attacaacta aaaatatat ctaagcattt gcaaaggcga 10501 caataaatta ttgacgctta acctttccag tttataagac tggaatataa tttcaaacca 10561 cacattagta cttatgttgc acaatgagaa aagaaattag tttcaaattt acctcagcgt 10621 ttgtgtatcg ggcaaaaatc gttttgcccg attccgtatt ggtatacttt tgcttcagtt 10681 gcatatctta aaactaaatg taatttatta actaatcaag aaaaacatct ttggctgagc 10741 tcggtggctc atgcctgtaa tcccaacact ttgagaagct gaggtgggag gagtgcttga 10801 ggccaggagt tcaagaccag cctgggcaac ataggagac ccccatcttt acaaagaaaa 10861 aaaaaagggg aaaagaaaat cttttaaatc tttggatttg atcactacaa gtattatttt 10921 acaagtgaaa taaacatacc attttctttt agattgtgtc attaaatgga atgaggtctc 10981 ttagtacagt tattttgatg cagataattc cttttagttt agctactatt ttaggggatt 11041 tttttagag gtaactcact atgaaatagt tctccttaat gcaaatatgt tggttctgct 11101 atagttccat cctgttcaaa agtcaggatg aatatgaaga gtggtgtttc cttttgagca 11161 attcttcatc cttaagtcag catgattata agaaaaatag aaccctcagt gtaactctaa 11221 ttcctttta ctattccagt gtgatctctg aaattaaatt acttcaacta aaaattcaaa 11281 tactttaaat cagaagattt catagttaat ttatttttt tttcaacaaa atggtcatcc 11341 aaactcaaac ttgagaaaat atcttgcttt caaattggca ctgatt
```

By "DNMT1" is meant a gene that transcribes an RNA having at least 85% nucleotide sequence identity to NM_001130823 NM_001379. An exemplary DNMT1 sequence is provided below:

(SEQ ID NO: 3)
```
  1 ggctccgttc catccttctg cacagggtat cgcctctctc cgtttggtac atcccctcct 61 ccccacgcc cggactgggg tggtagacgc cgcctccgct catcgcccct ccccatcggt 121 ttccgcgcga aaagccgggg cgcctgcgct gccgccgccg cgtctgctga agcctccgag 181 atgccggcgc gtaccgcccc agcccgggtg cccacactgg ccgtcccggc catctcgctg 241 cccgacgatg tccgcaggcg gctcaaagat ttggaaagag acagcttaac agaaaaggaa 301 tgtgtgaagg agaaattgaa tctcttgcac gaatttctgc aaacagaaat aaagaatcag
```

-continued

```
 361 ttatgtgact tggaaaccaa attacgtaaa gaagaattat ccgaggaggg ctacctggct
 421 aaagtcaaat ccctttaaa taaagatttg tccttggaga acggtgctca tgcttacaac
 481 cgggaagtga atggacgtct agaaaacggg aaccaagcaa gaagtgaagc ccgtagagtg
 541 ggaatggcag atgccaacag cccccccaaa ccccttcca aacctcgcac gcccaggagg
 601 agcaagtccg atggagaggc taagcgttca agagaccctc ctgcctcagc ctcccaagta
 661 actgggatta gagctgaacc ttcacctagc cccaggatta caaggaaaag caccaggcaa
 721 accaccatca catctcattt tgcaagggc cctgccaaac ggaaacctca ggaagagtct
 781 gaaagagcca atcggatga gtccatcaag gaagaagaca agaccagga tgagaagaga
 841 cgtagagtta catccagaga acgagttgct agaccgcttc ctgcagaaga acctgaaaga
 901 gcaaaatcag gaacgcgcac tgaaaaggaa gaagaaagag atgaaaaaga gaaaagaga
 961 ctccgaagtc aaaccaaaga accaacaccc aaacagaaac tgaaggagga gccggacaga
1021 gaagccaggg caggcgtgca ggctgacgag gacgaagatg gagacgagaa agatgagaag
1081 aagcacagaa gtcaacccaa agatctagct gccaaacgga ggcccgaaga aaaagaacct
1141 gaaaaagtaa atccacagat ttctgatgaa aagacgagg atgaaaagga ggagaagaga
1201 cgcaaaacga cccccaaaga accaacggag aaaaaatgg ctcgcgccaa aacagtcatg
1261 aactccaaga cccaccctcc caagtgcatt cagtgcgggc agtacctgga cgaccctgac
1321 ctcaaatatg ggcagcaccc accagacgcg gtggatgagc cacagatgct gacaaatgag
1381 aagctgtcca tctttgatgc caacgagtct ggctttgaga gttatgaggc gcttccccag
1441 cacaaactga cctgcttcag tgtgtactgt aagcacggtc acctgtgtcc catcgacacc
1501 ggcctcatcg agaagaatat cgaactcttc ttttctggtt cagcaaaacc aatctatgat
1561 gatgacccat ctcttgaagg tggtgttaat ggcaaaaatc ttggccccat aaatgaatgg
1621 tggatcactg gctttgatgg aggtgaaaag gccctcatcg gcttcagcac ctcatttgcc
1681 gaatacattc tgatggatcc cagtcccgag tatgcgccca tatttgggct gatgcaggag
1741 aagatctaca tcagcaagat tgtggtggag ttcctgcaga gcaattccga ctcgacctat
1801 gaggacctga tcaacaagat cgagaccacg gttcctcctt ctggcctcaa cttgaaccgc
1861 ttcacagagg actccctcct gcgacacgcg cagtttgtgg tggagcaggt ggagagttat
1921 gacgaggccg gggacagtga tgagcagccc atcttcctga cccctgcat gcgggacctg
1981 atcaagctgg ctggggtcac gctgggacag aggcgagccc aggcgaggcg gcagaccatc
2041 aggcattcta ccagggagaa ggacaggga cccacgaaag ccaccaccac caagctggtc
2101 taccagatct tcgatacttt cttcgcagag caaattgaaa aggatgacag agaagacaag
2161 gagaacgcct ttaagcgccg gcgatgtggc gttggtgatg tgtgtcagca gcctgagtgt
2221 gggaaatgta aagcctgcaa ggacatggtt aaatttggtg gcagtggacg gagcaagcag
2281 gcttgccaag gcggaggtg tcccaatatg gccatgaagg aggcagatga cgatgaggaa
2341 gtcgatgata acatcccaga gatgccgtca cccaaaaaaa tgcaccaggg gaagaagaag
2401 aaacagaaca agaatcgcat ctcttgggtc ggagaagccg tcaagactga tgggaagaag
2461 agttactata agaaggtgtg cattgatgcg gaaaccctgg aagtggggga ctgtgtctct
2521 gttattccag atgattcctc aaaaccgctg tatctagcaa gggtcacggc gctgtgggag
2581 gacagcagca acgggcagat gtttcacgcc cactggttct gcgctgggac agacacagtc
2641 ctcggggcca cgtcggaccc tctggagctg ttcttggtgg atgaatgtga ggacatgcag
2701 cttttcatata tccacagcaa agtgaaagtc atctacaaag ccccctccga aaactgggcc
```

-continued

```
2761  atggagggag gcatggatcc cgagtccctg ctggaggggg acgacgggaa gacctacttc
2821  taccagctgt ggtatgatca agactacgcg agattcgagt cccctccaaa aacccagcca
2881  acagaggaca acaagttcaa attctgtgtg agctgtgccc gtctggctga gatgaggcaa
2941  aaagaaatcc ccagggtcct ggagcagctc gaggacctgg atagccgggt cctctactac
3001  tcagccacca agaacggcat cctgtaccga gttggtgatg tgtgtacct gccccctgag
3061  gccttcacgt tcaacatcaa gctgtccagt cccgtgaaac gcccacggaa ggagcccgtg
3121  gatgaggacc tgtacccaga gcactaccgg aaatactccg actacatcaa aggcagcaac
3181  ctggatgccc ctgagcccta ccgaattggc cggatcaaag agatcttctg tcccaagaag
3241  agcaacggca ggcccaatga gactgacatc aaaatccggg tcaacaagtt ctacaggcct
3301  gagaacaccc acaagtccac tccagcgagc taccacgcag acatcaacct gctctactgg
3361  agcgacgagg aggccgtggt ggacttcaag gctgtgcagg gccgctgcac cgtggagtat
3421  ggggaggacc tgcccgagtg cgtccaggtg tactccatgg gcggccccaa ccgcttctac
3481  ttcctcgagg cctataatgc aaagagcaaa agctttgaaa tcctcccaa ccatgcccgt
3541  agccctggaa acaaagggaa gggcaaggga aaagggaagg gcaagcccaa gtcccaagcc
3601  tgtgagccga gcgagccaga gatagagatc aagctgccca agctgcggac cctggatgtg
3661  ttttctggct gcgggggtt gtcggaggga ttccaccaag caggcatctc tgacacgctg
3721  tgggccatcg agatgtggga ccctgcggcc caggcgttcc ggctgaacaa ccccggctcc
3781  acagtgttca cagaggactg caacatcctg ctgaagctgg tcatggctgg ggagaccacc
3841  aactcccgcg ccagcggct gccccagaag ggagacgtgg agatgctgtg cggcgggccg
3901  ccctgccagg gcttcagcgg cttgaaccgc ttcaattcgc gcacctactc caagttcaaa
3961  aactctctgt ggtttccttt cctcagctac tgcgactact accggccccg gttcttcctc
4021  ctggagaatg tcaggaactt tgtctccttc aagcgctcca tggtcctgaa gctcacccctc
4081  cgctgcctgt ccgcatggg ctatcagtgc accttcggcg tgctgcaggc cggtcagtac
4141  ggcgtggccc agactaggag gcgggccatc atcctggccg cggcccctgg agagaagctc
4201  cctctgttcc cggagccact gcacgtgttt gctccccggg cctgccagct gagcgtggtg
4261  gtggatgaca agaagtttgt gagcaacata accaggttga gctcgggtcc tttccggacc
4321  atcacggtgc gagacacgat gtccgacctg ccggaggtgc ggaatggagc ctcggcactg
4381  gagatctcct acaacgggga gcctcagtcc tggttccaga ggcagctccg gggcgcacag
4441  taccagccca tcctcaggga ccacatctgt aaggacatga gtgcattggt ggctgcccgc
4501  atgcggcaca tccccttggc cccagggtca gactggcgcg atctgcccaa catcgaggtg
4561  cggctctcag acggcaccat ggccaggaag ctgcggtata cccaccatga caggaagaac
4621  ggccgcagca gctctggggc cctccgtggg gtctgctcct gcgtggaagc cggcaaagcc
4681  tgcgaccccg cagccaggca gttcaacacc ctcatcccct ggtgcctgcc ccacaccggg
4741  aaccggcaca accactgggc tggcctctat ggaaggctcg agtgggacgg cttcttcagc
4801  acaaccgtca ccaaccccga gcccatgggc aagcagggcc gcgtgctcca cccagagcag
4861  caccgtgtgg tgagcgtgcg ggagtgtgcc cgctcccagg gcttccctga cacctaccgg
4921  ctcttcggca acatcctgga caagcaccgg caggtgggca atgccgtgcc accgcccctg
4981  gccaaagcca ttggcttgga gatcaagctt tgtatgttgg ccaaagcccg agagagtgcc
5041  tcagctaaaa taaaggagga ggaagctgct aaggactagt tctgccctcc cgtcaccct
5101  gtttctggca ccaggaatcc ccaacatgca ctgatgttgt gttttaaca tgtcaatctg
5161  tccgttcaca tgtgtggtac atggtgtttg tggccttggc tgacatgaag ctgttgtgtg
```

-continued

```
5221 aggttcgctt atcaactaat gatttagtga tcaaattgtg cagtactttg tgcattctgg 5281 attttaaaag ttttttatta tgcattatat caaatctacc actgtatgag tggaaattaa 5341 gactttatgt agttttata tgttgtaata tttcttcaaa taaatctctc ctataaacca 5401 aaaaaaaaaa aaaaaaaaaa aaaaa
```

By "LDHA" is meant a gene that transcribes an RNA having at least 85% nucleotide sequence identity to NM_005566, NM_001135239, NM_001165414, NM_001165415, NM_001165416, or NR_028500. An exemplary LDHA sequence is provided below:

(SEQ ID NO: 4)
```
   1 gtctgccggt cggttgtctg gctgcgcgcg ccacccgggc ctctccagtg ccccgcctgg 61 ctcggcatcc accccagcc cgactcacac gtgggttccc gcacgtccgc cggccccccc 121 cgctgacgtc agcatagctg ttccacttaa ggcccctccc gcgcccagct cagagtgctg 181 cagccgctgc cgccgattcc ggatctcatt gccacgcgcc cccgacgacc gcccgacgtg 241 cattcccgat tccttttggt tccaagtcca atatggcaac tctaaaggat cagctgattt 301 ataatcttct aaaggaagaa cagaccccc agaataagat tacagttgtt ggggttggtg 361 ctgttggcat ggcctgtgcc atcagtatct taatgaagga cttggcagat gaacttgctc 421 ttgttgatgt catcgaagac aaattgaagg gagagatgat ggatctccaa catggcagcc 481 ttttccttag aacaccaaag attgtctctg gcaaagacta taatgtaact gcaaactcca 541 agctggtcat tatcacggct ggggcacgtc agcaagaggg agaaagccgt cttaatttgg 601 tccagcgtaa cgtgaacatc tttaaattca tcattcctaa tgttgtaaaa tacagcccga 661 actgcaagtt gcttattgtt tcaaatccag tggatatctt gacctacgtg gcttggaaga 721 taagtggttt tcccaaaaac cgtgttattg gaagcggttg caatctggat tcagcccgat 781 tccgttacct aatgggggaa aggctggag ttcacccatt aagctgtcat gggtgggtcc 841 ttggggaaca tggagattcc agtgtgcctg tatggagtgg aatgaatgtt gctggtgtct 901 ctctgaagac tctgcaccca gatttaggga ctgataaaga taaggaacag tggaaagagg 961 ttcacaagca ggtggttgag agtgcttatg aggtgatcaa actcaaaggc tacacatcct 1021 gggctattgg actctctgta gcagatttgg cagagagtat aatgaagaat cttaggcggg 1081 tgcacccagt ttccaccatg attaagggtc tttacggaat aaaggatgat gtcttcctta 1141 gtgttcctg cattttggga cagaatggaa tctcagacct tgtgaaggtg actctgactt 1201 ctgaggaaga ggcccgtttg aagaagagtg cagatacact ttgggggatc caaaaggagc 1261 tgcaatttta aagtcttctg atgtcatatc atttcactgt ctaggctaca acaggattct 1321 aggtggaggt tgtgcatgtt gtccttttta tctgatctgt gattaaagca gtaatatttt 1381 aagatggact gggaaaaaca tcaactcctg aagttagaaa taagaatggt ttgtaaaatc 1441 cacagctata tcctgatgct ggatggtatt aatcttgtgt agtcttcaac tggttagtgt 1501 gaaatagttc tgccacctct gacgcaccac tgccaatgct gtacgtactg catttgcccc 1561 ttgagccagg tggatgttta ccgtgtgtta tataacttcc tggctccttc actgaacatg 1621 cctagtccaa catttttcc cagtgagtca catcctggga tccagtgtat aaatccaata 1681 tcatgtcttg tgcataattc ttccaaagga tcttattttg tgaactatat cagtagtgta 1741 cattaccata taatgtaaaa agatctacat acaaacaatg caaccaacta tccaagtgtt 1801 ataccaacta aaaccccaa taaaccttga acagtgacta ctttggttaa ttcattatat 1861 taagatataa agtcataaag ctgctagtta ttatattaat ttggaaatat taggctattc
```

-continued

```
1921 ttgggcaacc ctgcaacgat tttttctaac agggatatta ttgactaata gcagaggatg 1981 taatagtcaa ctgagttgta ttggtaccac ttccattgta agtcccaaag tattatatat 2041 ttgataataa tgctaatcat aattggaaag taacattcta tatgtaaatg taaaatttat 2101 ttgccaactg aatataggca atgatagtgt gtcactatag gaacacaga ttttgagat 2161 cttgtcctct ggaagctggt aacaattaaa aacaatctta aggcagggaa aaaaaaaaa 2221 aaaaaa
```

By "MAD2L2" is meant a gene that transcribes an RNA having at least 85% nucleotide sequence identity to NM_001127325, NM_006341, or BC015244.

```
                                                         (SEQ ID NO: 5)
   1 tgcccccagc cgaggggcag ccccggggcc gggcccggcg cgcacccggc cagcgcgccc 61 tcgccagctg cgctctgagt tctgggccag ctccccagag gcctaggcgc cgccgccgcg 121 agggcgcggg gcagacaaag gaggcagaca aaggcgggcg cagcccagca gccgtgcggg 181 caccgggcga ggcaggccca ctcctcccgg tagcgggaag gatgaccacg ctcacacgac 241 aagacctcaa cttggccaa gtggtggccg atgtgctctg cgagttcctg gaggtggctg 301 tgcatctcat cctctacgtg cgcgaggtct accccgtggg catcttccag aaacgcaaga 361 agtacaacgt gccggtccag atgtcctgcc acccggagct gaatcagtat atccaggaca 421 cgctgcactg cgtcaagcca ctcctggaga agaatgatgt ggagaaagtg gtggtggtga 481 ttttggataa agagcaccgc ccagtggaga aattcgtctt tgagatcacc cagcctccac 541 tgctgtccat cagctcagac tcgctgttgt ctcatgtgga gcagctgctc cgggccttca 601 tcctgaagat cagcgtgtgc gatgccgtcc tggaccacaa ccccccaggc tgtaccttca 661 cagtcctggt gcacacgaga gaagccgcca ctcgcaacat ggagaagatc caggtcatca 721 aggatttccc ctggatcctg gcggatgagc aggatgtcca catgcatgac ccccggctga 781 taccactaaa aaccatgacg tcggacattt taaagatgca gctttacgtg gaagagcgcg 841 ctcataaagg cagctgaggg ggcacctgcc accccactga tgcccaaact gtcagacttt 901 gggggatccc cgcctagggc agtgctgcat ggctgccctg attccaagtg ctcttatcgc 961 ctctgtgtgt ggatcgcccg ccccagcccg gggccgctca ggtctgcttg gaggatgcct 1021 ccccaggag ggcagtgagg gatgccgcaa cctcgacttc tcagcctcct ggggttccgc 1081 cggccaacac tgtctgtctc aaatactgtg ctgtgagttg tttcaataaa ggggccccaa 1141 gggctgggct gaaaaaaaa aaaaaaaaa aaaaaaaaa aaaaaaaaa aaaaaa
```

By "NBN" is meant a gene that transcribes an RNA having at least 85% nucleotide sequence identity to NM_002485. An exemplary NBN sequence is provided below:

```
                                                         (SEQ ID NO: 6)
   1 gagcgcgcac gtcccggagc ccatgccgac cgcaggcgcc gtatccgcgc tcgtctagca 61 gccccggtta cgcggttgca cgtcggcccc agccctgagg agccggaccg atgtggaaac 121 tgctgcccgc cgcgggcccg gcaggaggag aaccatacag acttttgact ggcgttgagt 181 acgttgttgg aaggaaaaac tgtgccattc tgattgaaaa tgatcagtcg atcagccgaa 241 atcatgctgt gttaactgct aacttttctg taaccaacct gagtcaaaca gatgaaatcc 301 ctgtattgac attaaaagat aattctaagt atggtacctt tgttaatgag gaaaaaatgc 361 agaatggctt ttcccgaact ttgaagtcgg gggatggtat tacttttgga gtgtttggaa
```

-continued

```
 421 gtaaattcag aatagagtat gagcctttgg ttgcatgctc ttcttgttta gatgtctctg
 481 ggaaaactgc tttaaatcaa gctatattgc aacttggagg atttactgta aacaattgga
 541 cagaagaatg cactcacctt gtcatggtat cagtgaaagt taccattaaa acaatatgtg
 601 cactcatttg tggacgtcca attgtaaagc cagaatattt tactgaattc ctgaaagcag
 661 ttgagtccaa gaagcagcct ccacaaattg aaagttttta cccacctctt gatgaaccat
 721 ctattggaag taaaaatgtt gatctgtcag gacggcagga agaaaacaa atcttcaaag
 781 ggaaaacatt tatattttg aatgccaaac agcataagaa attgagttcc gcagttgtct
 841 ttggaggtgg ggaagctagg ttgataacag aagagaatga agaagaacat aatttctttt
 901 tggctccggg aacgtgtgtt gttgatacag aataacaaa ctcacagacc ttaattcctg
 961 actgtcagaa gaaatggatt cagtcaataa tggatatgct ccaaaggcaa ggtcttagac
1021 ctattcctga agcagaaatt ggattggcgg tgattttcat gactacaaag aattactgtg
1081 atcctcaggg ccatcccagt acaggattaa agacaacaac tccaggacca agcctttcac
1141 aaggcgtgtc agttgatgaa aaactaatgc caagcgcccc agtgaacact acaacatacg
1201 tagctgacac agaatcagag caagcagata catgggattt gagtgaaagg ccaaaagaaa
1261 tcaaagtctc caaaatggaa caaaaattca gaatgctttc acaagatgca cccactgtaa
1321 aggagtcctg caaaacaagc tctaataata atagtatggt atcaaatact ttggctaaga
1381 tgagaatccc aaactatcag ctttcaccaa ctaaattgcc aagtataaat aaaagtaaag
1441 atagggcttc tcagcagcag cagaccaact ccatcagaaa ctactttcag ccgtctacca
1501 aaaaaggga aagggatgaa gaaaatcaag aaatgtcttc atgcaaatca gcaagaatag
1561 aaacgtcttg ttctctttta gaacaaacac aacctgctac accctcattg tggaaaaata
1621 aggagcagca tctatctgag aatgagcctg tggacacaaa ctcagacaat aacttattta
1681 cagatacaga tttaaaatct attgtgaaaa attctgccag taaatctcat gctgcagaaa
1741 agctaagatc aaataaaaaa agggaaatgg atgatgtggc catagaagat gaagtattgg
1801 aacagttatt caaggacaca aaaccagagt tagaaattga tgtgaaagtt caaaaacagg
1861 aggaagatgt caatgttaga aaaaggccaa ggatggatat agaaacaaat gacactttca
1921 gtgatgaagc agtaccagaa agtagcaaaa tatctcaaga aaatgaaatt gggaagaaac
1981 gtgaactcaa ggaagactca ctatggtcag ctaaagaaat atctaacaat gacaaacttc
2041 aggatgatag tgagatgctt ccaaaaaagc tgttattgac tgaatttaga tcactggtga
2101 ttaaaaactc tacttccaga aatccatctg gcataaatga tgattatggt caactaaaaa
2161 atttcaagaa attcaaaaag gtcacatatc ctggagcagg aaaacttcca cacatcattg
2221 gaggatcaga tctaatagct catcatgctc gaaagaatac agaactagaa gagtggctaa
2281 ggcaggaaat ggaggtacaa aatcaacatg caaaagaaga gtctcttgct gatgatcttt
2341 ttagatacaa tccttattta aaaggagaa gataactgag gattttaaaa agaagccatg
2401 gaaaaacttc ctagtaagca tctacttcag gccaacaagg ttatatgaat atatagtgta
2461 tagaagcgat ttaagttaca atgttttatg gcctaaattt attaaataaa atgcacaaaa
2521 ctttgattct tttgtatgta acaattgttt gttctgtttt caggctttgt cattgcatct
2581 ttttttcatt tttaaatgtg tttttgttat taaatagtta atatagtcac agttcaaaat
2641 tctaaatgta cgtaaggtaa agactaaagt caccctccca ccattgtcct agctacttgg
2701 ttcccctcag aaaaaaattc atgatactca tttcttatga atctttccag ggattttga
2761 gtcctattca aattcctatt tttaaataat ttcctacaca aatgatagca taacatatgc
2821 agtgttctac accttgcttt tttacttagt agattaaaaa ttataggaat atcaatataa
```

```
2881 tgttttaat attttttctt ttccattatg ctgtagtctt acctaaactc tggtgatcca 2941 aacaaaatgg cttcagtggt gcagatgtca cctacatgtt attctagtac tagaaactga 3001 agaccatgtg gagacttcat caaacatggg tttagttttc accagaatgg aaagacctgt 3061 acccctttt ggtggtctta ctgagctggg tgggtgtctg ttttgagctt atttagagtc 3121 ctagttttcc tacttataaa gtagaaatgg tgagattgtt ttcttttct accttaaagg 3181 gagatggtaa gaaacaatga atgtctttt tcaaacttta ttgacaagtg attttcaagt 3241 ctgtgttcaa aaatatattc atgtacctgt gatccagcaa gagggagtt ccagtcaaga 3301 gtcactacaa ctgattagtt gtttagagaa tgagaaatgg aacagtgagg aatggaggcc 3361 atatttccat gacttccctt gtaaacagaa gcaacagaag ggacaagagg ctggcctcta 3421 catcactctc accttccaaa tcttgtggaa gtgcatctac ttgccagaac caaattaact 3481 tacttccaag ttctggctgc ttgcaggtgg aactccagct gcagggagt tagggaaatg 3541 aaggtcttt tttaaaagct tctcagcctt cctagggaac agaaattggg tgagccaatc 3601 tgcaatttct actacaggca ttgagaccag ttagattatt gaaatattat agagagttat 3661 gaacacttaa attatgatag tggtatgaca ttggatagaa catgggatac tttagaagta 3721 gaattgacag ggcatattag ttgatgaaat ggagtcattt gagtctctta atagccatgt 3781 atcataatta ccaagtgaag ctggtggaac atatggtctc cattttacag ttaaggaata 3841 taatggacag attaatattg ttctctgtca tgcccacaat ccctttctaa ggaagactgc 3901 cctactatag cagttttat atttgtcaat ttatgaatat aatgaatgag agttctggta 3961 cctcctgtct ttacaaatat tggtgttgtc agtatttttc cttttaacc attccaatcg 4021 gtgtgtagtg atgtttcatt ttggttttaa tttgtatatc cctgatagct ataattgggt 4081 catagaaatt ctttatacat tctagatgca agtctcttgt cggatatatg tattgagata 4141 ttacacctag tctgtggctt gactgttttc tttatgtctt ttgatgaata gaagttttaa 4201 attttgacaa ggtcaaattt attttttct tttgtttgat attttttctc tccaatttaa 4261 ccccaagatt tcagatattc tgctctatta tataaacttt atattttat atttgtgatc 4321 taccttgaat tgatatgtat gttgtgaatt atggatcagg gttcttttt tcccccatac 4381 aagtatccag tcattgtaac actgtttatt gaaagaatta tcctttcctc attaaattac 4441 cttgccaatt agtaaaaaat caattaacca taatggtgga tctgtttctg gactttctgt 4501 ttggttacac tgaaatgttt gtccatcctt gcactcactc ataccatact gccttgaatt 4561 actgtagctg catagatgct ccttaagttg ggattacatt gtaataaacg caatgtaagt 4621 taaaaaaaaa aaaaaaaa
```

By "NONO" is meant a gene that transcribes an RNA having at least 85% nucleotide sequence identity to NM_001145408, NM_007363, NM_001145409, or NM_001145410. An exemplary NONO sequence is provided below:

(SEQ ID NO: 7)
```
  1 caggcgcagt gcaggactgc tccgagcacg cctacgcgcg cattttctcc ccttcctctc 61 cctcttccca ctttcctctc cctttttctc ctctcctttc cccctcccac cacttggtct 121 ttcagtcttt cagtcagttc gtttaggtct ctccttccga cccccacccc cagctcctct 181 cccttctt ttccccctcc ccctttcctt tccgtctca cgcgccaggc cgcttgcaca 241 tgcgcattag gtacaaagcc tcgctctttg tccccatctg tcgttcacac gaactcaagc
```

-continued

```
 301 ctttggcatt cggcagccaa tagaatctaa gaaatggcgg aaaaatgatt ccgcctcggg
 361 agctaaacct tgattggcag tttagctaac caatcgagaa cgccattttg tacccttgg
 421 caggcaccga gctccgtcgt ctcgtttccg gcggtcgcgc gctcttttct cgggacggga
 481 gaggccgtgt agcgtcgccg ttactccgag gagataccag tcggtagagg agaagtcgag
 541 gttagaggga actgggaggc actttgctgt ctgcaatcga agttgagagg cccagtattt
 601 aggcgacagt gaatttatta ctctgaagag ggttctgcac atatttccaa attatattgg
 661 tggtcatcag aagtaggtga taggaagaaa tacttctcaa gggtgcaaaa atgcagagta
 721 ataaaacttt taacttggag aagcaaaacc atactccaag aaagcatcat caacatcacc
 781 accagcagca gcaccaccag cagcaacagc agcagccgcc accaccgcca atacctgcaa
 841 atgggcaaca ggccagcagc caaaatgaag gcttgactat tgacctgaag aattttagaa
 901 aaccaggaga gaagaccttc acccaacgaa gccgtctttt tgtgggaaat cttcctcccg
 961 acatcactga ggaagaaatg aggaaactat ttgagaaata tggaaaggca ggcgaagtct
1021 tcattcataa ggataaagga tttggcttta tccgcttgga aacccgaacc ctagcggaga
1081 ttgccaaagt ggagctggac aatatgccac tccgtggaaa gcagctgcgt gtgcgctttg
1141 cctgccatag tgcatccctt acagttcgaa accttcctca gtatgtgtcc aacgaactgc
1201 tggaagaagc ctttctgtg tttggccagg tagagagggc tgtagtcatt gtggatgatc
1261 gaggaaggcc ctcaggaaaa ggcattgttg agttctcagg gaagccagct gctcggaaag
1321 ctctggacag atgcagtgaa ggctccttcc tgctaaccac atttcctcgt cctgtgactg
1381 tggagcccat ggaccagtta gatgatgaag agggacttcc agagaagctg gttataaaaa
1441 accagcaatt tcacaaggaa cgagagcagc cacccagatt tgcacagcct ggctcctttg
1501 agtatgaata tgccatgcgc tggaaggcac tcattgagat ggagaagcag cagcaggacc
1561 aagtggaccg caacatcaag gaggctcgtg agaagctgga gatggagatg gaagctgcac
1621 gccatgagca ccaggtcatg ctaatgagac aggatttgat gaggcgccaa gaagaacttc
1681 ggaggatgga agagctgcac aaccaagagg tgcaaaaacg aaagcaactg gagctcaggc
1741 aggaggaaga gcgcaggcgc cgtgaagaag agatgcggcg gcagcaagaa gaaatgatgc
1801 ggcgacagca ggaaggattc aagggaacct tccctgatgc gagagagcag gagattcgga
1861 tgggtcagat ggctatggga ggtgctatgg gcataaacaa cagaggtgcc atgccccctg
1921 ctcctgtgcc agctggtacc ccagctcctc caggacctgc cactatgatg ccggatggaa
1981 ctttgggatt gacccccacca caactgaac gctttggtca ggctgctaca atggaaggaa
2041 ttgggcaat tggtggaact cctcctgcat tcaaccgtgc agctcctgga gctgaatttg
2101 ccccaaacaa acgtcgccga tactaataag ttgcagtgtc tagtttctca aaacccttaa
2161 aagaaggacc cttttggac tagccagaat tctaccctgg aaaagtgtta gggattcctt
2221 ccaatagtta gatctaccct gcctgtacta ctctagggag tatgctggag cagagggca
2281 agggaggggt ggtattaaac aagtcaattc tgtgtggtat attgtttaat cagttctgtg
2341 tggtgcattc ctgaagtctc taatgtgact gttgagggcc tggggaaacc atggcaaagt
2401 ggatccagtt agagcccatt aatcttgatc attccggttt ttttttttt tgtccaggtt
2461 gtttcatttg cttgccccgc ccccgagacg gagtcttact ctgtcgccca ggctggagtg
2521 tagtggcatg atctcggctc actgcaatct ctgcctccg ggttcaagct tgtccaggtt
2581 gatcttgaac tcctgacctc gtgatctacc cacctcggcc tcccaaaatg ctgggattac
2641 aggggtgagc caccgtgccc aacctcactt gcttcttatc cttacactcc ccagccca
2701 gagaaactgc cacatacacc acaaaaacca aacatccccc aatgaccttta gccccattgc
```

-continued

```
2761 tccattcact cccaggtgag aattcaggca aacgtccaca aaggtcacag gcagcgtaca 2821 tacggttctg ttataccca tatattaccc cttcatgtcc taaagaagac attttctctt 2881 agagattttc attttagtgt atctttaaaa aaaaatcttg tgttaacttg cctccatctt 2941 tttcttgggt gaggacaccc aggaatgacc cttttgtgtc tatgatgttg ctgttcacag 3001 cttttcttga taggcctagt acaatcttgg gaacagggtt actgtatact gaaggtctga 3061 cagtagctct tagactcgcc tatcttaggt agtcatgctg tgcatttttt ttttcattgg 3121 tgtactgtgt ttgatttgtc tcatatattt ggagttttc tgaaaaatgg agcagtaatg 3181 cagcatcaac ctattaaaat acattttaag cctttaaaa aaaaaaaa
```
15

By "DNAPK" is meant a gene that transcribes an RNA having at least 85% nucleotide sequence identity to NM_006904 or NM_001081640. DNAPK is also refered to as PRKDC. An exemplary DNAPK sequence is provided below:

(SEQ ID NO: 8)
```
   1 ggggcatttc cgggtccggg ccgagcgggc gcacgcgcgg gagcgggact cggcggcatg 61 gcgggctccg gagccggtgt gcgttgctcc ctgctgcggc tgcaggagac cttgtccgct 121 gcggaccgct gcggtgctgc cctggccggt catcaactga tccgcggcct ggggcaggaa 181 tgcgtcctga gcagcagccc cgcggtgctg gcattacaga catctttagt tttttccaga 241 gatttcggtt tgcttgtatt tgtccggaag tcactcaaca gtattgaatt tcgtgaatgt 301 agagaagaaa tcctaaagtt tttatgtatt ttcttagaaa aaatgggcca gaagatcgca 361 ccttactctg ttgaaattaa gaacacttgt accagtgttt atacaaaaga tagagctgct 421 aaatgtaaaa ttccagcccc tggaccttctt attaagttac ttcagacttt tagaagttct 481 agactcatgg atgaatttaa aattggagaa ttatttagta aattctatgg agaacttgca 541 ttgaaaaaaa aaataccaga tacagtttta gaaaaagtat atgagctcct aggattattg 601 ggtgaagttc atcctagtga gatgataaat aatgcagaaa acctgttccg cgcttttctg 661 ggtgaactta agacccagat gacatcagca gtaagagagc ccaaactacc tgttctggca 721 ggatgtctga aggggttgtc ctcacttctg tgcaacttca ctaagtccat ggaagaagat 781 ccccagactt caagggagat tttttaattt tgtactaaagg caattcgtcc tcagattgat 841 ctgaagagat atgctgtgcc ctcagctggc ttgcgcctat ttgccctgca tgcatctcag 901 tttagcacct gccttctgga caactacgtg tctctattg aagtcttgtt aaagtggtgt 961 gcccacacaa atgtagaatt gaaaaaagct gcactttcag ccctggaatc ctttctgaaa 1021 caggtttcta atatggtggc gaaaaatgca gaaatgcata aaaataaact gcagtacttt 1081 atggagcagt tttatggaat catcagaaat gtggattcga acaacaagga gttatctatt 1141 gctatccgtg gatatggact ttttgcagga ccgtgcaagg ttataaacgc aaaagatgtt 1201 gacttcatgt acgttgagct cattcagcgc tgcaagcaga tgttcctcac ccagacagac 1261 actggtgacg accgtgttta tcagatgcca agcttcctcc agtctgttgc aagcgtcttg 1321 ctgtaccttg acacagttcc tgaggtgtat actccagttc tggagcacct cgtggtgatg 1381 cagatagaca gtttcccaca gtacagtcca aaaatgcagc tggtgtgttg cagagccata 1441 gtgaaggtgt tcctagcttt ggcagcaaaa gggccagttc tcaggaattg cattagtact 1501 gtggtgcatc agggttttaat cagaatatgt tctaaaccag tggtccttcc aaagggccct 1561 gagtctgaat ctgaagacca ccgtgcttca ggggaagtca gaactggcaa atggaaggtg
```

-continued

```
1621 cccacataca aagactacgt ggatctcttc agacatctcc tgagctctga ccagatgatg
1681 gattctattt tagcagatga agcattttc tctgtgaatt cctccagtga aagtctgaat
1741 catttacttt atgatgaatt tgtaaaatcc gttttgaaga ttgttgagaa attggatctt
1801 acacttgaaa tacagactgt tggggaacaa gagaatggag atgaggcgcc tggtgtttgg
1861 atgatcccaa cttcagatcc agcggctaac ttgcatccag ctaaacctaa agatttttcg
1921 gctttcatta acctggtgga attttgcaga gagattctcc ctgagaaaca agcagaattt
1981 tttgaaccat gggtgtactc atttctatat tgaattaattt tgcaatctac aaggttgccc
2041 ctcatcagtg gtttctacaa attgctttct attacagtaa gaaatgccaa gaaaataaaa
2101 tatttcgagg gagttagtcc aaagagtctg aaacactctc ctgaagaccc agaaaagtat
2161 tcttgctttg ctttatttgt gaaatttggc aaagaggtgg cagttaaaat gaagcagtac
2221 aaagatgaac ttttggcctc ttgtttgacc tttcttctgt ccttgccaca caacatcatt
2281 gaactcgatg ttagagccta cgttcctgca ctgcagatgc ctttcaaact gggcctgagc
2341 tataccccct tggcagaagt aggcctgaat gctctagaag aatggtcaat ttatattgac
2401 agacatgtaa tgcagcctta ttacaaagac attctcccct gcctggatgg atacctgaag
2461 acttcagcct tgtcagatga gaccaagaat aactgggaag tgtcagctct ttctcgggct
2521 gcccagaaag gatttaataa agtggtgtta aagcatctga agaagacaaa gaacctttca
2581 tcaaacgaag caatatcctt agaagaaata agaattagag tagtacaaat gcttggatct
2641 ctaggaggac aaataaacaa aaatcttctg acagtcacgt cctcagatga gatgatgaag
2701 agctatgtgg cctgggacag agaagcgg ctgagctttg cagtgccctt tagagagatg
2761 aaacctgtca ttttcctgga tgtgttcctg cctcgagtca cagaattagc gctcacagcc
2821 agtgacagac aaactaaagt tgcagcctgt gaactttac atagcatggt tatgtttatg
2881 ttgggcaaag ccacgcagat gccagaaggg ggacagggag ccccacccat gtaccagctc
2941 tataagcgga cgtttcctgt gctgcttcga cttgcgtgtg atgttgatca ggtgacaagg
3001 caactgtatg agccactagt tatgcagctg attcactggt tcactaacaa caagaaattt
3061 gaaagtcagg atactgttgc cttactagaa gctatattgg atggaattgt ggaccctgtt
3121 gacagtactt taagagattt ttgtggtcgg tgtattcgag aattccttaa atggtccatt
3181 aagcaaataa caccacagca gcaggagaag agtccagtaa acaccaaatc gcttttcaag
3241 cgactttata gccttgcgct tcaccccaat gctttcaaga ggctgggagc atcacttgcc
3301 tttaataata tctacaggga attcagggaa gaagagtctc tggtggaaca gtttgtgttt
3361 gaagccttgg tgatatacat ggagagtctg gccttagcac atgcagatga gaagtcctta
3421 ggtacaattc aacagtgttg tgatgccatt gatcacctat gccgcatcat tgaaaagaag
3481 catgtttctt taaataaagc aaagaaacga cgtttgccgc gaggatttcc accttccgca
3541 tcattgtgtt tattggatct ggtcaagtgg ctttagctc attgtgggag gccccagaca
3601 gaatgtcgac acaaatccat tgaactcttt tataaattcg ttcctttatt gccaggcaac
3661 agatcccta atttgtggct gaaagatgtt ctcaaggaag aaggtgtctc ttttctcatc
3721 aacaccttg agggggggtgg ctgtggccag ccctcgggca tcctggccca gcccacccctc
3781 ttgtaccttc ggggggccatt cagcctgcag gccacgctat gctggctgga cctgctcctg
3841 gccgcgttgg agtgctacaa cacgttcatt ggcgagagaa ctgtaggagc gctccaggtc
3901 ctaggtactg aagcccagtc ttcacttttg aaagcagtgg cttttcttctt agaaagcatt
3961 gccatgcatg acattatagc agcagaaaag tgctttggca ctggggcagc aggtaacaga
4021 acaagcccac aagagggaga aaggtacaac tacagcaaat gcaccgttgt ggtccggatt
```

-continued

```
4081  atggagttta ccacgactct gctaaacacc tccccggaag gatggaagct cctgaagaag 4141  gacttgtgta atacacacct gatgagagtc ctggtgcaga cgctgtgtga gcccgcaagc 4201  ataggtttca acatcggaga cgtccaggtt atggctcatc ttcctgatgt ttgtgtgaat 4261  ctgatgaaag ctctaaagat gtccccatac aaagatatcc tagagaccca tctgagagag 4321  aaaataacag cacagagcat tgaggagctt tgtgccgtca acttgtatgg ccctgacgcg 4381  caagtggaca ggagcaggct ggctgctgtt gtgtctgcct gtaaacagct tcacagagct 4441  gggcttctgc ataatatatt accgtctcag tccacagatt tgcatcattc tgttggcaca 4501  gaacttcttt ccctggttta taaaggcatt gcccctggag atgagagaca gtgtctgcct 4561  tctctagacc tcagttgtaa gcagctggcc agcggacttc tggagttagc ctttgctttt 4621  ggaggactgt gtqaqcqcct tqtqaqtctt ctcctgaacc cagcggtgct gtccacggcg 4681  tccttgggca gctcacaggg cagcgtcatc cacttctccc atggggagta tttctatagc 4741  ttgttctcag aaacgatcaa cacggaatta ttgaaaaatc tggatcttgc tgtattggag 4801  ctcatgcagt cttcagtgga taataccaaa atggtgagtg ccgttttgaa cggcatgtta 4861  gaccagagct tcagggagcg agcaaaccag aaacaccaag gactgaaact tgcgactaca 4921  attctgcaac actggaagaa gtgtgattca tggtgggcca agattcccc tctcgaaact 4981  aaaatggcag tgctggcctt actggcaaaa attttacaga ttgattcatc tgtatctttt 5041  aatacaagtc atggttcatt ccctgaagtc tttacaacat atattagtct acttgctgac 5101  acaaagctgg atctacattt aaagggccaa gctgtcactc ttcttccatt cttcaccagc 5161  ctcactggag gcagtctgga ggaacttaga cgtgttctgg agcagctcat cgttgctcac 5221  ttccccatgc agtccaggga atttcctcca ggaactccgc ggttcaataa ttatgtggac 5281  tgcatgaaaa agtttctaga tgcattggaa ttatctcaaa gccctatgtt gttggaattg 5341  atgacagaag ttctttgtcg ggaacagcag catgtcatgg aagaattatt tcaatccagt 5401  ttcaggagga ttgccagaag gggttcatgt gtcacacaag taggccttct ggaaagcgtg 5461  tatgaaatgt tcaggaagga tgaccccgc ctaagtttca cacgccagtc cttgtggac 5521  cgctccctcc tcactctgct gtggcactgt agcctggatg ctttgagaga attcttcagc 5581  acaattgtgg tggatgccat tgatgtgttg aagtccaggt ttacaaagct aaatgaatct 5641  acctttgata ctcaaatcac caagaagatg ggctactata agattctaga cgtgatgtat 5701  tctcgccttc ccaaagatga tgttcatgct aaggaatcaa aaattaatca agtttttccat 5761  ggctcgtgta ttacagaagg aaatgaactt acaaagacat tgattaaatt gtgctacgat 5821  gcatttacag agaacatggc aggagagaat cagctgctgg agaggagaag actttaccat 5881  tgtgcagcat acaactgcgc catatctgtc atctgctgtg tcttcaatga gttaaaattt 5941  taccaaggtt ttctgtttag tgaaaaacca gaaaagaact tgcttatttt tgaaaatctg 6001  atcgacctga agcgccgcta taattttcct gtagaagttg aggttcctat ggaaagaaag 6061  aaaaagtaca ttgaaattag gaaagaagcc agagaagcag caaatgggga ttcagatggt 6121  ccttcctata tgtcttccct gtcatatttg gcagacagta ccctgagtga ggaaatgagt 6181  caatttgatt tctcaaccgg agttcagagc tattcataca gctcccaaga ccctagacct 6241  gccactggtc gttttcggag acgggagcag cgggacccca cggtgcatga tgatgtgctg 6301  gagctggaga tggacgagct caatcggcat gagtgcatgg cgcccctgac ggccctggtc 6361  aagcacatgc acagaagcc gggcccgcct caaggagaag aggattcagt gccaagagat 6421  cttccttctt ggatgaaatt cctccatggc aaactgggaa atccaatagt accattaaat
```

```
6481  atccgtctct tcttagccaa gcttgttatt aatacagaag aggtctttcg cccttacgcg
6541  aagcactggc ttagcccctt gctgcagctg gctgcttctg aaaacaatgg aggagaagga
6601  attcactaca tggtggttga gatagtggcc actattcttt catggacagg cttggccact
6661  ccaacagggg tccctaaaga tgaagtgtta gcaaatcgat tgcttaattt cctaatgaaa
6721  catgtctttc atccaaaaag agctgtgttt agacacaacc ttgaaattat aaagacccntt
6781  gtcgagtgct ggaaggattg tttatccatc ccttataggt aatatttga aaagtttttcc
6841  ggtaaagatc ctaattctaa agacaactca gtagggattc aattgctagg catcgtgatg
6901  gccaatgacc tgcctcccta tgacccacag tgtggcatcc agagtagcga atacttccag
6961  gctttggtga ataatatgtc ctttgtaaga tataaagaag tgtatgccgc tgcagcagaa
7021  gttctaggac ttatacttcg atatgttatg gagagaaaaa acatactgga ggagtctctg
7081  tgtgaactgg ttgcgaaaca attgaagcaa catcagaata ctatggagga caagtttatt
7141  gtgtgcttga acaaagtgac caagagcttc cctcctcttg cagacaggtt catgaatgct
7201  gtgttctttc tgctgccaaa atttcatgga gtgttgaaaa cactctgtct ggaggtggta
7261  cttttgtcgtg tggagggaat gacagagctg tacttccagt taaagagcaa ggacttcgtt
7321  caagtcatga gacatagaga tgatgaaaga caaaaagtat gtttggacat aatttataag
7381  atgatgccaa agttaaaacc agtagaactc cgagaacttc tgaaccccgt tgtggaattc
7441  gtttcccatc cttctacaac atgtagggaa caaatgtata atattctcat gtggattcat
7501  gataattaca gagatccaga aagtgagaca gataatgact cccaggaaat atttaagttg
7561  gcaaaagatg tgctgattca aggattgatc gatgagaacc ctggacttca attaattatt
7621  cgaaatttct ggagccatga aactaggtta ccttcaaata ccttggaccg gttgctggca
7681  ctaaattcct tatattctcc taagatagaa gtgcactttt taagtttagc aacaaatttt
7741  ctgctcgaaa tgaccagcat gagcccagat tatccaaacc ccatgttcga gcatcctctg
7801  tcagaatgcg aatttcagga atataccatt gattctgatt ggcgtttccg aagtactgtt
7861  ctcactccga tgtttgtgga gacccaggcc tcccagggca ctctccagac ccgtacccag
7921  gaagggtccc tctcagctcg ctggccagtg gcagggcaga taagggccac ccagcagcag
7981  catgacttca cactgacaca gactgcagat ggaagaagct catttgattg gctgaccggg
8041  agcagcactg acccgctggt cgaccacacc agtccctcat ctgactcctt gctgtttgcc
8101  cacaagagga gtgaaaggtt acagagagca cccttgaagt cagtggggcc tgattttggg
8161  aaaaaaaggc tgggccttcc aggggacgag gtggataaca aagtgaaagg tgcggccggc
8221  cggacggacc tactacgact gcgcagacgg tttatgaggg accaggagaa gctcagtttg
8281  atgtatgcca gaaaaggcgt tgctgagcaa aaacgagaga aggaaatcaa gagtgagtta
8341  aaaatgaagc aggatgccca ggtcgttctg tacagaagct accggcacgg agaccttcct
8401  gacattcaga tcaagcacag cagcctcatc accccgttac aggccgtggc ccagagggac
8461  ccaataattg caaaacagct ctttagcagc ttgttttctg gaattttgaa agagatggat
8521  aaatttaaga cactgtctga aaaaacaac atcactcaaa agttgcttca agacttcaat
8581  cgtttttctta ataccaccctt ctctttcttt ccacccttttg tctcttgtat tcaggacatt
8641  agctgtgggc acgcagccct gctgagcctc gacccagcgg ctgttagcgc tggttgcctg
8701  gccagcctac agcagcccgt gggcatccgc tgctagagg aggctctgct ccgcctgctg
8761  cctgctgagc tgcctgccaa gcgagtccgt gggaaggccc gcctccctcc tgatgtcctc
8821  agatgggtgg agcttgctaa gctgtataga tcaattggag aatacgacgt cctccgtggg
8881  attttttacca gtgagatagg aacaaagcaa atcactcaga gtgcattatt agcagaagcc
```

-continued

```
8941   agaagtgatt attctgaagc tgctaagcag tatgatgagg ctctcaataa acaagactgg
9001   gtagatggtg agcccacaga agccgagaag gattttgggg aacttgcatc ccttgactgt
9061   tacaaccacc ttgctgagtg gaaatcactt gaatactgtt ctacagccag tatagacagt
9121   gagaaccccc cagacctaaa taaaatctgg agtgaaccat tttatcagga aacatatcta
9181   ccttacatga tccgcagcaa gctgaagctg ctgctccagg gagaggctga ccagtccctg
9241   ctgacattta ttgacaaagc tatgcacggg gagctccaga aggcgattct agagcttcat
9301   tacagtcaag agctgagtct gctttacctc ctgcaagatg atgttgacag agccaaatat
9361   tacattcaaa atggcattca gagttttatg cagaattatt ctagtattga tgtcctctta
9421   caccaaagta gactcaccaa attgcagtct gtacaggctt taacagaaat tcaggagttc
9481   atcagctttta taagcaaaca aggcaattta tcatctcaag ttcccctaa gagacttctg
9541   aacacctgga caaacagata tccagatgct aaaatggacc caatgaacat ctgggatgac
9601   atcatcacaa atcgatgttt ctttctcagc aaaatagagg agaagcttac ccctcttcca
9661   gaagataata gtatgaatgt ggatcaagat ggagacccca gtgacaggat ggaagtgcaa
9721   gagcaggaag aagatatcag ctccctgatc aggagttgca agtttccat gaaaatgaag
9781   atgatagaca gtgcccggaa gcagaacaat ttctcacttg ctatgaaact actgaaggag
9841   ctgcataaag agtcaaaaac cagagacgat tggctggtga gctgggtgca gagctactgc
9901   cgcctgagcc actgccggag ccggtcccag ggctgctctg agcaggtgct cactgtgctg
9961   aaaacagtct ctttgttgga tgagaacaac gtgtcaagct acttaagcaa aaatattctg
10021  gctttccgtg accagaacat tctcttgggt acaacttaca ggatcatagc gaatgctctc
10081  agcagtgagc cagcctgcct tgctgaaatc gaggaggaca aggctagaag aatcttagag
10141  ctttctggat ccagttcaga ggattcagag aaggtgatcg cgggtctgta ccagagagca
10201  ttccagcacc tctctgaggc tgtgcaggcg gctgaggagg aggcccagcc tccctcctgg
10261  agctgtgggc ctgcagctgg ggtgattgat gcttacatga cgctggcaga tttctgtgac
10321  caacagctgc gcaaggagga agagaatgca tcagttattg attctgcaga actgcaggcg
10381  tatccagcac ttgtggtgga gaaaatgttg aaagctttaa aattaaattc caatgaagcc
10441  agattgaagt ttcctagatt acttcagatt atagaacggt atccagagga gactttgagc
10501  ctcatgacaa aagagatctc ttccgttccc tgctggcagt tcatcagctg gatcagccac
10561  atggtggcct tactggacaa agaccaagcc gttgctgttc agcactctgt ggaagaaatc
10621  actgataact acccgcaggc tattgtttat cccttcatca taagcagcga aagctattcc
10681  ttcaaggata cttctactgg tcataagaat aaggagtttg tggcaaggat taaaagtaag
10741  ttggatcaag gaggagtgat tcaagatttt attaatgcct tagatcagct ctctaatcct
10801  gaactgctct ttaaggattg gagcaatgat gtaagagctg aactagcaaa acccctgta
10861  aataaaaaaa acattgaaaa aatgtatgaa agaatgtatg cagccttggg tgacccaaag
10921  gctccaggcc tgggggcctt tagaaggaag tttattcaga cttttggaaa agaatttgat
10981  aaacattttg ggaaaggagg ttctaaacta ctgagaatga agctcagtga cttcaacgac
11041  attaccaaca tgctactttt aaaaatgaac aaagactcaa agccccctgg gaatctgaaa
11101  gaatgttcac cctggatgag cgacttcaaa gtggagttcc tgagaaatga gctggagatt
11161  cccggtcagt atgacggtag gggaaagcca ttgccagagt accacgtgcg aatcgccggg
11221  tttgatgagc gggtgacagt catggcgtct ctgcgaaggc ccaagcgcat catcatccgt
11281  ggccatgacg agagggaaca cccttttcctg gtgaagggtg gcgaggacct gcggcaggac
```

```
11341  cagcgcgtgg agcagctctt ccaggtcatg aatgggatcc tggcccaaga ctccgcctgc
11401  agccagaggg ccctgcagct gaggacctat agcgttgtgc ccatgacctc caggttagga
11461  ttaattgagt ggcttgaaaa tactgttacc ttgaaggacc ttcttttgaa caccatgtcc
11521  caagaggaga aggcggctta cctgagtgat cccagggcac cgccgtgtga atataaagat
11581  tggctgacaa aaatgtcagg aaaacatgat gttggagctt acatgctaat gtataagggc
11641  gctaatcgta ctgaaacagt cacgtctttt agaaaacgag aaagtaaagt gcctgctgat
11701  ctcttaaagc gggccttcgt gaggatgagt acaagccctg aggctttcct ggcgctccgc
11761  tcccacttcg ccagctctca cgctctgata tgcatcagcc actggatcct cgggattgga
11821  gacagacatc tgaacaactt tatggtggcc atggagactg gcggcgtgat cgggatcgac
11881  tttgggcatg cgtttggatc cgctacacag tttctgccag tccctgagtt gatgcctttt
11941  cggctaactc gccagtttat caatctgatg ttaccaatga agaaacgggg ccttatgtac
12001  agcatcatgg tacacgcact ccgggccttc cgctcagacc ctggcctgct caccaacacc
12061  atggatgtgt tgtcaagga gccctccttt gattggaaaa attttgaaca gaaaatgctg
12121  acaaaagtgg ggtcatggat tcaagaaata aatgttgctg aaaaaaattg gtaccccga
12181  cagaaaatat gttacgctaa gagaaagtta gcaggtgcca atccagcagt cattacttgt
12241  gatgagctac tcctgggtca tgagaaggcc cctgccttca gagactatgt ggctgtggca
12301  cgaggaagca agatcacaa cattcgtgcc caagaaccag agagtgggct ttcagaagag
12361  actcaagtga agtgcctgat ggaccaggca acagacccca acatccttgg cagaacctgg
12421  gaaggatggg agccctggat gtgaggtctg tgggagtctg cagatagaaa gcattacatt
12481  gtttaaagaa tctactatac tttggttggc agcattccat gagctgattt tcctgaaaca
12541  ctaaagagaa atgtctttg tgctacagtt tcgtagcatg agtttaaatc aagattatga
12601  tgagtaaatg tgtatgggtt aaatcaaaga taaggttata gtaacatcaa agattaggtg
12661  aggtttatag aaagatagat atccaggctt accaaagtat taagtcaaga atataatatg
12721  tgatcagctt tcaaagcatt tacaagtgct gcaagttagt gaaacagctg tctccgtaaa
12781  tggaggaaat gtggggaagc cttggaatgc ccttctggtt ctggcacatt ggaaagcaca
12841  ctcagaaggc ttcatcacca agattttggg agagtaaagc taagtatagt tgatgtaaca
12901  ttgtagaagc agcataggaa caataagaac ataggtaaa gctataatta tggcttatat
12961  ttagaaatga ctgcatttga tattttagga tattttttcta ggtttttttcc tttcattta
13021  ttctcttcta gttttgacat tttatgatag atttgctctc tagaaggaaa cgtctttatt
13081  taggagggca aaaattttgg tcatagcatt cacttttgct attccaatct acaactggaa
13141  gatacataaa agtgctttgc attgaatttg ggataacttc aaaaatccca tggttgttgt
13201  tagggatagt actaagcatt tcagttccag gagaataaaa gaaattccta tttgaaatga
13261  attcctcatt tggaggaaaa aaagcatgca ttctagcaca acaagatgaa attatggaat
13321  acaaaagtgg ctccttccca tgtgcagtcc ctgtcccccc ccgccagtcc tccacaccca
13381  aactgttttct gattggcttt tagctttttg ttgttttttt ttttccttct aacacttgta
13441  tttggaggct cttctgtgat tttgagaagt atactcttga gtgtttaata aagtttttttt
13501  ccaaaagta
```

By "RAD23B" is meant a gene that transcribes an RNA having at least 85% nucleotide sequence identity to NM_002874. An exemplary RAD23B sequence is provided below:

```
                                                             (SEQ ID NO: 9)
   1 gggggcacgt ctcggcgagt cacgatgatg gcggccacca tcctgtggtg agctagcgga
  61 ttccctgctt gtctcgccga cccccctcgcg ccttctgcag actccgtggc tggcgctcgg
 121 cgcgtgagga agcacggcgg cccgagttcg cggggaaggc cgcagtcgcg gaggcagcgg
 181 cgcggtccgg ggcacgggct gggggagagg ccgctccgct gggcgaatgt gacaagcccc
 241 cacccccacc gccttcctcc ccagagcgcg aggagcgcgg gcgacccccgg ggccccgcca
 301 ggccacagac cccgcccagc ggccagcacc cggcgcaggc ccggcagccg agctgcgcgg
 361 cggcaccatg caggtcaccc tgaagaccct ccagcagcag accttcaaga tagacattga
 421 ccccgaggag acggtgaaag cactgaaaga gaagattgaa tctgaaaagg ggaaagatgc
 481 ctttccagta gcaggtcaaa aattaattta tgcaggcaaa atcctcaatg atgatactgc
 541 tctcaaagaa tataaaattg atgagaaaaa ctttgtggtg gttatggtga ccaaacccaa
 601 agcagtgtcc acaccagcac cagctacaac tcagcagtca gctcctgcca gcactacagc
 661 agttacttcc tccaccacca caactgtggc tcaggctcca accctgtcc ctgccttggc
 721 ccccacttcc acacctgcat ccatcactcc agcatcagcg acagcatctt ctgaacctgc
 781 acctgctagt gcagctaaac aagagaagcc tgcagaaaag ccagcagaga caccagtggc
 841 tactagccca acagcaactg acagtacatc gggtgattct tctcggtcaa acctttttga
 901 agatgcaacg agtgcacttg tgacgggtca gtcttacgag aatatggtaa ctgagatcat
 961 gtcaatgggc tatgaacgag agcaagtaat tgcagccctg agagccagtt tcaacaaccc
1021 tgacagagca gtggagtatc tttaatggg aatccctgga gatagagaaa gtcaggctgt
1081 ggttgacccc cctcaagcag ctagtactgg ggctcctcag tcttcagcag tggctgcagc
1141 tgcagcaact acgacagcaa caactacaac aacaagttct ggaggacatc cccttgaatt
1201 tttacggaat cagcctcagt ttcaacagat gagacaaatt attcagcaga tccttccttt
1261 gcttccagcg ttactacagc agataggtcg agagaatcct caattacttc agcaaattag
1321 ccaacaccag gagcatttta ttcagatgtt aaatgaacca gttcaagaag ctggtggtca
1381 aggaggagga ggtggaggtg gcagtggagg aattgcagaa gctggaagtg gtcatatgaa
1441 ctacattcaa gtaacacctc aggaaaaaga agctatagaa aggttaaagg cattaggatt
1501 tcctgaagga cttgtgatac aagcgtattt tgcttgtgag aagaatgaga atttggctgc
1561 caattttctt ctacagcaga actttgatga agattgaaag ggactttttt atatctcaca
1621 cttcacacca gtgcattaca ctaacttgtt cactggattg tctgggatga cttgggctca
1681 tatccacaat acttggtata aggtagtaga ttgttggggg tggggaggga gggatctagg
1741 atacagggca gggataaata cagtgcatgt ctgcttcaat tagcagatgc cgcaactcca
1801 cacagtgtgt aaaatatata caaccaaaaa tcagcttttg caggtcttta tttcttctgt
1861 aaaacagtag gtaactttc ctaggtttca ctcttttag tgtactagat ccagaaactt
1921 agtgtaatgc cctgctttat atttctttga cttaacattg gtttcagaaa gaatcttagc
1981 tacctagaat ttacagtctc tgtttcatgg caacactgga taatggcttt gtgaaattta
2041 aaaaatttt gtagcgactg taaacagaaa tgccaaattg atggttaatt gttgctgctt
2101 caaaaataag tataaaatta atatgtaagg aagcccattc tttcatgtta aatacttggg
2161 gtgggagggg agaaagggaa ccttttctta aatgaaaat aattactgct attttaaaat
2221 ttcttgatca ttgaatgtga gacccttcta acatgatttg agaagctgta caagtatagg
2281 cagagttatt ttcctgttta catttttttt ttgttttggg gaaaaaattg gtaggtgtct
```

-continued

```
2341 aattactgtt tacttcattg ttatattgca gtaaaagttt taaaacaacc attgcatgtt 2401 tgcttttgat gtatcccttt gtgaaattag cacttttggg gccaatggag aaatgcagca 2461 ttcactctcc ctgtctttc cccttccctc agcagaaacg tgtttatcag caagtcgtga 2521 gtcaaactgc tgccttttaa aaacccaca aaatgctgat tcagttcaaa attaatgcaa 2581 atgtttcaaa actgggtttc tgatatttgt aaatgtgttt ctttattaga taagagtgta 2641 ttaccattaa agtcattagt ataatattgc tttcaaaaag aaatggtaga caaaactata 2701 atccagcatc ttttattgca ttggaaagac tggcaaagtc ttttggatgg gttgggagat 2761 gtggctggaa agtactttgg aaaatataca atcaagatat ctcatggcat attaaaagaa 2821 aaatcttaat agcagtgttg gctttatttt ggatttttc atctcagttt tttctgtgga 2881 atctccttca ttggcattgt tatttaatca taaacgggc agatgtctac ttgttcagtt 2941 tttcaaatct gttttcctga gtataaataa gagtatttaa agaaataatt tggattgctt 3001 ttgttttttg tttccttttt tttaaccatc tgatactaag aagatgaatt tgcacagatt 3061 tctctgcata atttctcaat atctttagca cagtatggtg atgatgactt taagcattt 3121 acatcacgta ctcataacct attatgaaaa taaatgaaac tggctgggta tggtggctca 3181 tgcctataat cccagcactt tgggaggccg aggtgggcag atcacttgag gccaggagat 3241 tgagaccagc ctgaccgtca tggcgaaacc ccgtctatac taaaaataca aaaaatagcc 3301 aggcatggtg gcgcacgcct gtggtcccag ctacttggga ggctgaggca tgagaattgc 3361 ttgaacccgg gaagtgaagg ttgccgtgag ctgagatcac accactgcca taaacatgac 3421 aggcttttgg actttgtatt acctgtatgt tttataatgg atcatgcata atttctcagg 3481 agaataaaat gagaattcat atatacgttc atctttcaag tcagagcaat gagttgggaa 3541 aagaggtggc atttctgatc ggataatgga atactctcat ttatttatg acattctctg 3601 tctactcaga tcatagtgaa aactggaaac aaaaaaaaaa aacagcctct tcttggaaag 3661 tgacagcaga aggtggcatg gagcttgtgt ccttggacaa caaatctgga tatactagga 3721 ttaattatca gaagacagct caggccaagt tttgatcgtt ccatacagta ccttgtttat 3781 ctgcttctta aagaatcagc cgagacacca taaagaaat aggcttttg tgccttttgc 3841 tgttaatgtt taatttacaa actgttttgg taaatctctt aatgtaagta gctafttgac 3901 tttggaattt tgcattcgag gtatactgtc atttcttgaa atctttttct cgtttagttg 3961 ctctgtggga aatgtgagga agcctaagtt tgtatttgta aatttcttat gccatcctct 4021 agtcaaattt tttttcattg tttaaaaata cggaagtgtt ccaatataat ttttcctgt 4081 actggatggc taggattcta gagaattgat tataaaatat tttcaataca
```

By "RAD54L" is meant a gene that transcribes an RNA having at least 85% nucleotide sequence identity to NM_003579 or NM_001142548. An exemplary RAD54L sequence is provided below:

(SEQ ID NO: 10)

```
  1 gatacgacgg cagcgcggcg ggaggttcga ttacccggt cttggcgggt cggtgagtct 61 tggcggctgt taacgcgcgc tttgggaaca ggaaggttga gagagaggtg ctggggtctg 121 cgtctatctc tgtcgctctt ttcagcccct cctggtattc ccctcctaac ctgggttttt 181 tacacgcccg cgtggcttcc tgctcgacct ccctgagtct gatcctggtt tccacctcca 241 gccctgggaa atttcctttc tccagactcg ccctccccac ccgggcctcg gactttcacc 301 ccagcttctc tctcctggcc agtgattacc caccccaat cccaccccgc ccgccgcgc
```

-continued

```
 361 aactacctcc tcccttcacc cggactggga ccatcatccc cactccactc cgcccagtct
 421 gggactccac ctgcctcctc cccaatccca cactaatctc tgcttggtct cttcctcttt
 481 ggcctaatct ctcgtctcgg cttattgggg acggccactc tcacagtttg gttccaaaca
 541 ccagttcctg gatggattcc cgccatccat gcccctctt taattagccg gtcctctcaa
 601 taatgtagca gcccctcta cagattagac cctggtccta cactcttagc cgctgcctgc
 661 ttttgacctt tggctcatgg gtacttgacg ttttaaactc ctaggcccag gatgaggagg
 721 agcttggctc ccagccagct ggccaagaga aaacctgaag gcaggtcctg tgatgatgaa
 781 gactggcaac ctggcctagt gactcctagg aaacggaaat ccagcagtga gacccagatc
 841 caggagtgtt tcctgtctcc ttttcggaaa cctttgagtc agctaaccaa tcaaccacct
 901 tgtctggaca gcagtcagca tgaagcattt attcgaagca ttttgtcaaa gcctttcaaa
 961 gtccccattc caaattatca aggtcctctg ggctctcgag cattgggcct gaaaagggct
1021 ggggtccgcc gggccctcca tgaccccctg gaaaagatg ccttggttct gtatgagcct
1081 cccccgctga gcgctcatga ccagctgaag cttgacaagg agaaactccc tgtccatgtg
1141 gttgttgacc ctattctcag taaggttttg cggcctcatc agagagaggg agtgaaattc
1201 ctgtgggagt gtgtcaccag tcggcgcatc cctggcagcc atggctgcat catggctgat
1261 gagatgggcc taggaaagac gctgcagtgc atcacattga tgtggacact tttacgccag
1321 agtccagagt gcaagccaga aattgacaag gcagtggtgg tgtcgccttc cagcctggtg
1381 aagaactggt acaatgaggt tgggaaatgg ctcggaggga ggatccaacc tctggccatc
1441 gatggaggat ctaaggatga aatagaccaa aagctggaag gattcatgaa ccagcgtgga
1501 gccagggtgt cttctcccat cctcatcatt tcctatgaga ccttccgcct tcatgttgga
1561 gtcctccaga aggaagtgt tggtctggtc atatgtgacg agggacacag gctcaagaac
1621 tctgagaatc agacttacca agccctggac agcttgaaca ccagccggcg ggtgctcatc
1681 tccggaactc ccatccagaa tgatctgctt gagtatttca gcttggtaca ttttgttaat
1741 tccggcatcc tagggactgc ccatgaattc aagaagcatt ttgaattgcc aattttgaag
1801 ggtcgagacg ctgctgctag tgaggcagac aggcagctag gagaggagcg gctgcgggag
1861 ctcaccagca ttgtgaatag atgcctgata cggaggactt ctgatatcct ttctaaatat
1921 ctgcctgtga agattgagca ggtcgtttgt gtaggctga caccccttca gactgagtta
1981 tacaagaggt ttctgagaca agccaaaccg gcagaagaat tgcttgaggg caagatgagt
2041 gtgtcttccc tttcttccat cacctcgcta agaagctttt gtaatcatcc agctctaatc
2101 tatgataagt gtgtggaaga ggaggatggc tttgtgggtg ccttggacdt cttccctcct
2161 ggttacagct ctaaggccct ggagcccag ctgtcaggta agatgctggt cctggattat
2221 attctggcgg tgacccgaag ccgtagcagt gacaaagtag tgctggtgtc gaattacacc
2281 cagactttgg atctctttga gaagctgtgc cgtgcccgaa ggtacttata cgtccgcctg
2341 gatggcacga tgtccattaa gaagcgagcc aaggttgtag aacgcttcaa tagtccatcg
2401 agccctgact tgtcttcat gctgagcagc aaagctgggg gctgtggcct caatctcatt
2461 ggggctaacc ggctggtcat gtttgaccct gactggaacc cagccaatga tgaacaagcc
2521 atggcccggg tctggcgaga tggtcaaaag aagacttgct atatctaccg cctgctgtct
2581 gcagggacca ttgaggagaa gatcttccag cgtcagagcc acaagaaggc actgagcagc
2641 tgtgtggtgg atgaggagca ggatgtgagg cgccacttct ctctgggcga gttgaaggag
2701 ctgtttatcc tggatgaagc tagctcagt gacacacatg acaggttgca ctgccgacgt
```

```
-continued
2761 tgtgtcaaca gccgtcagat ccggccaccc cctgatggtt ctgactgcac ttcagacctg 2821 gcagggtgga accactgcac tgataagtgg gggctccggg atgaggtact ccaggctgcc 2881 tgggatgctg cctccactgc catcaccttc gtcttccacc agcgttctca tgaggagcag 2941 cgggccctcc gctgataacc agctggtctg ggtgtagctc ttagaggaag gagatangga 3001 aaagggctc cttgctccac agggccctgt tgaattttgt tctctgggag aaaatcatca 3061 agaagggctg catgatgttt gcccaaaatt tattttataa gaaaaacttt tttggttaaa 3121 aaaaagaata aaggtatgaa agggttaaaa aaaaaaaaa aaaa
```

By "PSMA" is meant prostate-specific membrane antigen, a polypeptide having at least 85% amino acid sequence identity to NP_004467, NP00104986, NP_001180400, NP_001180401, or NP_001180402.

By "A10-3" is meant an aptamer as shown in FIG. 13.

By "agent" is meant any small molecule chemical compound, antibody, nucleic acid molecule, or polypeptide, or fragments thereof.

By "ameliorate" is meant to decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "cancer" refers to a malignant tumor of potentially unlimited growth that expands locally by invasion and systemically by metastasis.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon, pancreas and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include cancer, in particular, any cancer that is amenable to treatment with ionizing radiation. Specific, non-limiting, examples of disease include prostate cancer, colon cancer, breast cancer, pancreatic cancer, and lung cancer.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Therapeutic treatment can be achieved upon single or multiple dose administration to a subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "neoplastic" refers to those cells having the capacity for autonomous growth, e.g., an abnormal state or condition characterized by rapidly proliferating cell growth. A neoplastic disease state may be categorized as pathologic, e.g., characterizing or constituting a disease state, or may be categorized as non-pathologic, e.g., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The language "inhibiting the growth" of the neoplasm includes the slowing, interrupting, arresting or stopping its growth and metastases and does not necessarily indicate a total elimination of the neoplastic growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the term neoplasia generally refers to cells experiencing abnormal cell growth rates. Neoplasias include "tumors," which may be either benign, premalignant or malignant.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence can be at least about 16 amino acids, at least about 20 amino acids, at least about 25 amino acids, or about 35 amino acids, about 50 amino acids, or about 100 amino acids. For nucleic acids, the length of the reference nucleic acid sequence can be at least about 50 nucleotides, at least about 60 nucleotides, at least about 75 nucleotides, or about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant a pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions can include temperatures of at least about 30° C., of at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In embodiments, hybridization will occur at 30° C. in 750 mM NaCl, 75 mM trisodium citrate, and 1% SDS. In other embodiments, hybridization will occur at 37° C. in 500 mM NaCl, 50 mM trisodium citrate, 1% SDS, 35% formamide, and 100 µg/ml denatured salmon sperm DNA (ssDNA). In embodiments, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, or less than about 15 mM NaCl and 1.5 mM trisodium citrate. Stringent temperature conditions for the wash steps can include a temperature of at least about 25° C., of at least about 42° C., or of at least about 68° C. In embodiments, wash steps will occur at 25° C. in 30 mM NaCl, 3 mM trisodium citrate, and 0.1% SDS. In other embodiments, wash steps will occur at 42° C. in 15 mM NaCl, 1.5 mM trisodium citrate, and 0.1% SDS. In related embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al. (Molecular Cloning: A Laboratory Manual, Cold Spring Harbor Laboratory Press, New York).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, 80% or 85%, 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 2A-2F are graphs showing the confirmation of siRNA mediated radiosensitization using clonogenic survival assays. Radiosensitization was confirmed by clonogenic survival assays (n=3). DU145 cells were reverse transfected with 5 nM control siRNA or (FIG. 2A) DNAPK, (FIG. 2B) MAD2L2, (FIG. 2C) BRCA2, (FIG. 2D) NBN, (FIG. 2E) RAD23B, or (FIG. 2F) RAD54L siRNA 72 hours prior to irradiation. DMF0.1 values are shown for each. Open diamonds, control siRNA; closed squares, candidate siRNA. SF, surviving fraction.

FIGS. 3A-3F are graphs showing the siRNA-mediated knock-down of radiosensitization target genes. DU145 cells were transfected with Candidate siRNAs (5 nM), 48 hours later the mRNA level of target genes were evaluated by qRT-PCR. Data are normalized to GAPDH mRNA. (FIG. 3A) DNA-PK, (FIG. 3B) MAD2L2, (FIG. 3C) BRCA2, (FIG. 3D) NBN, (FIG. 3E) Rad23B, and (FIG. 3F) RAD54L. Columns represent mean±S.E.M, n=3.

FIGS. 5A and 5B include structures of illustrative examples of aptamer-shRNA chimeras, including the secondary structure of (FIG. 5A) A10-3-DNAPK (SEQ ID NO: 44) and (FIG. 5B) Neg-DNAPK (SEQ ID NO: 47). Aptamer and shRNA portions are shown by brackets. FIGS. 5C-5C are graphs showing the results of aptamer-shRNA chimera-mediated RNAi in the absence of transfection reagents. (FIG. 5C) LNCaP cells were treated with 0, 4, 40, or 400 nM A10-3-DNAPK for 48 hours, and DNAPK mRNA levels were quantified by qRT-PCR. LNCaP cells were treated with 400 nM of (FIG. 5D) A10-3-DNAPK, (FIG. 5E) A10-3-BRCA2, or (FIG. 5F) A10-3-ATM for 48 hours. Respective target gene mRNA levels were quantified by qRT-PCR. Appropriate siRNAs were transfected (100 nM) as positive controls. Expression was normalized to GAPDH. Mean±SEM (n=3). *P<0.05.

FIG. 6 is a graph showing that aptamer-shRNA chimeras do not illicit an interferon response. $2\times10^5$ LNCaP cells were either transfected with DNA-PK siRNA or incubated with 400 nM A10-3-Con, A10-3-DNA-PK or NegDNA-PK for 48 hours before interferon β secretion into the cell culture supernatant was analyzed. Cells were separately treated with 5 μg/ml Poly(I:C) (Invitrogen, Carlsbad, Calif.) as a positive control. Detection of interferon β was accomplished by using a commercially available sandwich interferon β ELISA kit (PBL) following manufacturer's recommendations. 25-2,000 pg/ml of interferon-beta standard was used as a positive control for assay integrity. means±S.E.M, n=3.

FIGS. 7A and 7B include graphs depicting PSMA selectivity. (FIG. 7A) PC3-PIP or (FIG. 7B) PC3-Flu cells were treated with 400 nM aptamer-shRNA chimeras for 48 hours, and DNAPK expression was quantified by qRT-PCR. siRNA DNAPK (100 nM transfected) was included as a positive control. Expression is normalized to GAPDH. Mean±SEM (n=3). *P<0.05. FIG. 7C is a gel showing aptamer-shRNA chimera processing by Dicer in vitro. Cleavage products were analyzed by denaturing PAGE and ethidium bromide staining. Image was inverted for clarity. FIG. 7D includes a gel showing the results from a cell-based RNAi processing assay. LNCaP cells were treated with 400 nM aptamer-shRNA chimeras, and RNA was extracted 48 hours later for Northern blot assay. Probes are specific to corresponding antisense siRNAs. ds, double-stranded; ss, single-stranded. FIGS. 7E and 7F show the results from targeted in vivo knockdown. Subcutaneous LNCaP tumors were injected with aptamer-shRNA chimeras (200 pmol/injection) on days −3 and −2 and harvested on day 0, and DNAPK expression was determined. FIG. 7E is a graph showing qRT-PCR results. Mean±SEM. *P<0.05. FIG. 7F includes immunohistochemistry results. Original magnification, x400. FIGS. 7G and 7H include gels showing results from 5'-RACE PCR analysis to assess siRNA-mediated cleavage of DNAPK. LNCaP cells transfected with DNAPK siRNA or with A10-3-DNAPK chimeras produced a specific DNAPK cleavage product (FIG. 7G). In vivo treatment of LNCaP xenografts with A10-3-DNAPK chimera resulted in siRNA-mediated DNAPK cleavage (FIG. 7H).

FIG. 9A shows in vitro radiosensitization results. LNCaP cells treated with 400 nM A10-3-DNAPK or A10-3-Con or transfected with control siRNA were irradiated 48 hours later with 6 Gy IR, and cell viability was assessed 12 days later by MTS. Percent cell death is relative to nonirradiated cells. FIGS. 9B-9D show in vivo radiosensitization. Established tumors were treated with aptamer-shRNA chimeras (days −3 and −2) and either 6 Gy IR or no radiation (day 0). FIG. 9B shows results for the PC3 tumor model (n=3 per group). A10-3-DNAPK provided no significant therapeutic benefit to nonirradiated or irradiated PC3 tumors. Radiation similarly affected growth in all treatment groups. Mean±SEM. FIG. 9C shows results for the LNCaP tumor model (n≥6 per group). Radiation similarly affected growth in all treatment groups except irradiated A10-3-DNAPK. *P<0.05, *** P<0.001, A10-3-DNAPK IR vs. A 10-3-Con IR and A10-3-DNAPK IR vs. Neg-DNAPK IR; 2-way ANOVA. Mean±SEM. FIG. 9D shows the extension of tumor quadrupling for LNCaP tumor model. Events (animals whose tumor volume was not yet 4-fold the size at injection) were plotted by Kaplan-Meier curve. P<0.01, A10-3-Con IR vs. A10-3-Con and Neg-DNAPK IR vs. Neg-DNAPK; P<0.0001, A10-3-DNAPK IR vs. A10-3-Con IR and A10-3-DNAPK IR vs. Neg-DNAPK IR; log-rank (Mantel-Cox) test.

FIG. 10A: PBS(−R) (n=6); FIG. 10B: A10-3-Con (−R) (n=6); FIG. 10C: A10-3-DNA-PK(−R) (n=6); FIG. 10D: NegDNA-PK(−R) (n=6); FIG. 10E: A10-3-Con(+R) (n=6); FIG. 10F: Neg-DNA-PK (+R) (n=6); FIG. 10G: A10-3-DNAPK(+R) (n=8).

FIG. 12A is a table showing the sequences of the three oligonculeotides (SEQ ID NOS 63-65, respectively, in order of appearance) that comprise the aptamer-siRNA chimera. FIG. 12B shows the structure of the aptamer-siRNA chimera. To generate the aptamer-siRNA molecule the aptamer olignucleotide, sense strand-siRNA olignucleotide, and the antisense strand-siRNA are mixed and annealed. FIG.

12C is a graph showing the ability of the aptamer-siRNA chimera to knock-down expression of the target gene DNAPK.

Figure 13:
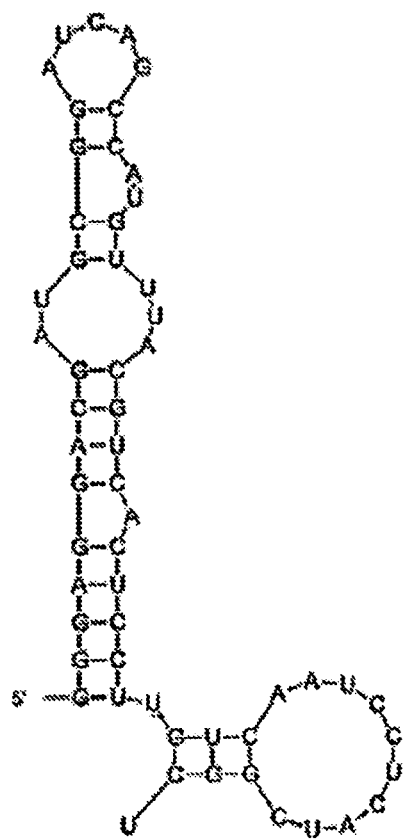

FIG. 13 shows the structure of the A10-3 aptamer.

DETAILED DESCRIPTION OF THE INVENTION

The invention features compositions comprising aptamer-inhibitory nucleic acid (e.g., shRNA) chimeras and methods of using the composition to sensitize a cancer cell to radiation.

The invention is based, at least in part, on the discovery that an aptamer that binds to prostate-specific membrane antigen (PSMA) is able to target an attached shRNA to prostate cancer cells and silence the gene that the shRNA targets. In addition, the invention is further based, at least in part, on the discovery of a set of genes, the inhibition of which results in the cancer cell becoming sensitized to ionizing radiation treatment. As described in more detail below, the discovery of these compositions and target genes demonstrates that the therapeutic index for local treatment of prostate cancer (PCa) can be improved by selectively sensitizing PCa cells to IR. The therapeutic strategy to deliver dose-escalated radiation therapy to the prostate, historically considered as more than approximately 70 Gy, has been constrained by the limited tolerance of the urinary tract and rectum (Leibel S A, Hanks G E, Kramer S. Patterns of care outcome studies: results of the national practice in adenocarcinoma of the prostate. *Int J Radiat Oncol Biol Phys*. 1984; 10(3):401-409; Smit W G, Helle P A, van Putten W L, Wijnmaalen A J, Seldenrath J J, van der Werf-Messing B H. Late radiation damage in prostate cancer patients treated by high dose external radiotherapy in relation to rectal dose. *Int J Radiat Oncol Biol Phys*. 1990; 18(1):23-29). Thus, the invention provides the benefits of dose-escalated radiation without the associated risks to normal tissue, the concomitant expensive high-tech infrastructure, and/or the added use of androgen suppression. Accordingly, the invention will have a significant impact on PCa morbidity and mortality.

The present invention provides methods of treating a disease or disorder or symptoms thereof which comprise administering a therapeutically effective amount of a pharmaceutical composition comprising an aptamer-inhibitory nucleic acid (e.g., shRNA) chimera to a subject (e.g., a mammal such as a human). Thus, one embodiment is a method of treating a subject suffering from cancer or symptom thereof. The method includes the step of administering to the mammal a therapeutic amount of an aptamer-inhibitory nucleic acid (e.g., shRNA) chimera followed by treating the mammal with ionizing radiation to treat the cancer or symptom thereof, under conditions such that the disease or disorder is treated. In certain embodiments the mammal is suffering from prostate cancer.

The methods herein include administering to the subject (including a subject identified as in need of such treatment) an effective amount of an aptamer-inhibitory nucleic acid (e.g., shRNA) chimera wherein the aptamer binds to a cell surface molecule on the cancer cell and the shRNA inhibits the expression of a target gene wherein the knock-down of the target gene product results in the cancer cell becoming radiosensitized. Following treatment with an aptamer-inhibitory nucleic acid (e.g., shRNA) chimera the cancer is further treated with ionizing radiation. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention in general comprise administration of therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Localized Cancer Cells

As used herein, "localized cancer cell" and "localized neoplastic cell" are used interchangeably and refer to a cancer/neoplastic cell present at the site of a tumor/cancer.

The aptamer-inhibitory nucleic acid chimeras are suitable for use to target any localized cancer cell. Cancers can affect a variety of cell types, tissues, or organs, including but not limited to bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Examples of such include, but are not limited to, melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stein glioma, pituitary adenoma, Kaposi's sarcoma, epidermoid cancer, squamous cell cancer, T-cell lymphoma, environmentally induced cancers including those induced by asbestos, and combinations of said cancers.

In embodiments, the localized cancer cell is a prostate cancer cell.

An estimated 1 in 6 men will be diagnosed with prostate cancer (PCa). Although the majority of these men can be successfully treated with surgery or radiation therapy, approximately 20%-40% will biochemically recur within 10 years of treatment (Ward J F, Moul J W. Rising prostate-specific antigen after primary prostate cancer therapy. *Nat Clin Pract Urol.* 2005; 2(4):174-182). This risk of recurrence is elevated to approximately 50% for men with locally advanced disease, a condition that is primarily managed by radiation therapy (Bolla M, et al. Long-term results with immediate androgen suppression and external irradiation in patients with locally advanced prostate cancer (an EORTC study): a phase III randomised trial. *Lancet.* 2002; 360(9327): 103-106; Walz J, et al. A nomogram predicting 10-year life expectancy in candidates for radical prostatectomy or radiotherapy for prostate cancer. *J Clin Oncol.* 2007; 25(24):3576-3581). Thus, new technologies that improve the therapeutic index of radiation therapy for local disease will significantly affect the morbidity and mortality of PCa.

Ionizing radiation (IR) causes multiple types of cellular injury, of which DNA double-strand breaks (DSBs) are considered the most cytotoxic (Smith G C, Jackson S P. The DNA-dependent protein kinase. *Genes Dev.* 1999; 13(8):916-934). Naturally occurring mutations in genes that sense or repair DNA damage are associated with increased sensitivity to IR (Helleday T, Lo J, van Gent D C, Engelward B P. DNA double-strand break repair: from mechanistic understanding to cancer treatment. *DNA Repair (Amst).* 2007; 6(7):923-935; Pollard J M, Gatti R A. Clinical radiation sensitivity with DNA repair disorders: an overview. *Int J Radiat Oncol Biol Phys.* 2009; 74(5):1323-1331). Chemical or siRNA inhibition of DNA repair proteins, such as ataxia telangiectasia mutated (ATM) or NBS1, also results in cellular hypersensitivity to IR (Chalmers A J, Bentzen S M, Buffa F M, A general framework for quantifying the effects of DNA repair inhibitors on radiation sensitivity as a function of dose. *Theor Biol Med. Model.* 2007; 4:25; Collis S J, Swartz M J, Nelson W G, DeWeese T L. Enhanced radiation and chemotherapy-mediated cell killing of human cancer cells by small inhibitory RNA silencing of DNA repair factors. *Cancer Res.* 2003; 63(7):1550-1554; Ohnishi K, Scuric Z, Schiestl R H, Okamoto N, Takahashi A, Ohnishi T. siRNA targeting NBS1 or XIAP increases radiation sensitivity of human cancer cells independent of TP53 status. *Radiat Res.* 2006; 166(3):454-462). Although these approaches have potential, they lack a means to selectively target cancer cells or specific tissues. Prostate-targeted radiosensitization approaches will both increase the therapeutic effect of IR and reduce radiation-associated damage to other pelvic tissues. RNAi is a promising new therapeutic approach. The challenge for translating RNAi therapy is delivery, particularly for specific cell types.

A prostate-specific membrane antigen-targeted (PSMA-targeted) RNA aptamers was previously developed (Lupold S E, Hicke B J, Lin Y, Coffey D S. Identification and characterization of nuclease-stabilized RNA molecules that bind human prostate cancer cells via the prostate-specific membrane antigen. *Cancer Res.* 2002; 62(14):4029-4033), which are capable of targeting drugs, nanoparticles, and toxins to PSMA-expressing PCa cells and tumors (Cheng J, et al. Formulation of functionalized PLGA-PEG nanoparticles for in vivo targeted drug delivery. *Biomaterials.* 2007; 28(5):869-876; Chu T C, et al. Aptamer:toxin conjugates that specifically target prostate tumor cells. *Cancer Res.* 2006; 66(12): 5989-5992; Chu T C, et al. Labeling tumor cells with fluorescent nanocrystal-aptamer bioconjugates. *Biosens Bioelectron.* 2006; 21(10):1859-1866; Farokhzad O C, et al. Targeted nanoparticle aptamer bioconjugates for cancer chemotherapy in vivo. *Proc Natl Acad Sci USA.* 2006; 103(16): 6315-6320; Farokhzad O C, Jon S, Khademhosseini A, Tran T N, Lavan D A, Langer R. Nanoparticle-aptamer bioconjugates: a new approach for targeting prostate cancer cells. *Cancer Res.* 2004; 64(21):7668-7672). When conjugated to siRNAs and shRNAs, these PSMA aptamers are also capable of delivering cell-selective gene knockdown (Chu T C, Twu K Y, Ellington A D, Levy M. Aptamer mediated siRNA delivery. *Nucleic Acids Res.* 2006; 34(10):e73; Dassie J P, et al. Systemic administration of optimized aptamer-siRNA chimeras promotes regression of PSMA-expressing tumors. *Nat. Biotechnol.* 2009; 27(9):839-849; McNamara J O 2nd, et al. Cell type-specific delivery of siRNAs with aptamer-siRNA chimeras. *Nat Biotechnol.* 2006; 24(8):1005-1015; Pastor F, Kolonias D, Giangrande P H, Gilboa E. Induction of tumour immunity by targeted inhibition of nonsense-mediated mRNA decay. *Nature.* 2010; 465(7295):227-230; Wullner U, Neef I, Eller A, Kleines M, Tur M K, Barth S. Cell-specific induction of apoptosis by rationally designed bivalent aptamer-siRNA transcripts silencing eukaryotic elongation factor 2. *Curr Cancer Drug Targets.* 2008; 8(7):554-565). Because PSMA is highly expressed in PCa, targeted aptamer-inhibitory nucleic acid (e.g., shRNA) chimeras could be used to inhibit DNA repair pathways in prostatic cells for enhanced radiation therapy of locally advanced PCa.

Dose-escalated radiation therapy for localized prostate cancer (PCa) has a clear therapeutic benefit; however, escalated doses may also increase injury to noncancerous tissues. Radiosensitizing agents can improve ionizing radiation (IR) potency, but without targeted delivery, these agents will also sensitize surrounding normal tissues. The prostate-targeted RNAi agents of the invention selectively sensitized prostate-specific membrane antigen-positive (PSMA-positive) cells to IR. siRNA library screens identified DNA-activated protein kinase, catalytic polypeptide (DNAPK) as a preferred radiosensitization target. As described herein, DNAPK shRNAs, delivered by PSMA-targeting RNA aptamers, selectively reduced DNAPK in PCa cells, xenografts, and human prostate tissues. Aptamer-targeted DNAPK shRNAs, combined with IR, dramatically and specifically enhanced PSMA-positive tumor response to IR.

Cancer cells on which the claimed chimeric aptamer-inhibitory nucleic acid (e.g., shRNA) molecules exert a therapeutic effect are not particularly limited. The results described herein demonstrate that the chimeric aptamers are effective in treating any localized cancer cells (e.g., prostate cancer cells). Therefore, in aspects of the invention, the chimeric aptamers are used in combination with radiotherapy, and in embodiments, use of the chimeric aptamers enhances the efficacy of the radiotherapy. It is readily within the skill of the ordinary artisan to choose the appropriate aptamer and shRNA for use with a particular type of cancer cell.

Use of the chimeric aptamers reduces the dosage of radiotherapy, and can suppress the side effects that accompany radiotherapy.

Aptamers

The aptamers of the invention may be prepared by any known method, including synthetic, recombinant, and purification methods, and may be used alone or in combination with other aptamers specific for the same target. Illustrative methods of preparing aptamers are disclosed in U.S. Pat. Nos. 5,582,981 and 5,840,867, both of which are incorporated by reference in their entirety. Further, as described more fully herein, the term "aptamer" specifically includes "secondary aptamers" containing a consensus sequence derived from comparing two or more known aptamers to a given target.

As used herein, the term "binding" refers to an interaction or complexation between a target and an oligonucleotide or aptamer, resulting in a sufficiently stable complex so as to permit separation of oligonucleotide:target complexes from uncomplexed oligonucleotides under given binding complexation or reaction conditions. Binding is mediated through hydrogen bonding or other molecular forces. As used herein, the term "binding" specifically excludes the normal "Watson-Crick"-type binding interactions (i.e., adenine-thymine and guanine-cytosine base-pairing) traditionally associated with the DNA double helix.

In general, a minimum of approximately 3 nucleotides, at least 5 nucleotides, and the like, are necessary to effect specific binding. The only apparent limitations on the binding specificity of the target/oligonucleotide complexes of the invention concern sufficient sequence to be distinctive in the binding oligonucleotide and sufficient binding capacity of the target substance to obtain the necessary interaction. Oligonucleotides of sequences shorter than 10 can be used when the appropriate interaction can be obtained in the context of the environment in which the target is placed. Although the oligonucleotides generally described herein are single-stranded or double-stranded, it is contemplated that aptamers may sometimes assume triple-stranded or quadruple-stranded structures.

As further explained below, the specifically binding oligonucleotides need to contain the sequence-conferring specificity, but may be extended with flanking regions and otherwise derivatized.

The aptamers found to bind to the targets may be isolated, sequenced, and then resynthesized as conventional DNA or RNA moieties, or may be "modified" oligomers which are those conventionally recognized in the art. As the resulting aptamers of the invention include intermediates in their synthesis, any of the hydroxyl groups ordinarily present may be replaced by phosphonate groups, phosphate groups, protected by a standard protecting group, or activated to prepare additional linkages to additional nucleotides, or may be conjugated to solid supports. The 5' terminal OH is conventionally free but may be phosphorylated; OH substituents at the 3' terminus may also be phosphorylated. The hydroxyls may also be derivatized to standard protecting groups. One or more phosphodiester linkages may be replaced by alternative linking groups. These alternative linking groups include, but are not limited to embodiments wherein P(O)O is replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotide through O or S, Not all linkages in an oligomer need to be identical.

"Analogous" forms of purines and pyrimidines are those generally known in the art, many of which are used as chemotherapeutic agents. An exemplary but not exhaustive list includes 2'-fluoro-modified pyrimidine, aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine.

Aptamer oligonucleotides may contain analogous forms of ribose or deoxyribose that are generally known in the art. An exemplary, but not exhaustive list includes locked-nucleic acids (LNA), 2' substituted sugars such as 2'-O-methyl-, 2'-fluoro- or 2'-azido-ribose, carbocyclic sugar analogs, α-anomeric sugars, epimeric sugars such as arabinose, xyloses or lyxoses, pyranose sugars, sedoheptuloses, acyclic analogs and abasic nucleoside analogs such as methyl riboside.

In most instances, the conventional sugars and bases will be used in applying the method of the invention; substitution of analogous forms of sugars, purines and pyrimidines may be advantageous in designing the final product.

Aptamers containing the specific binding sequences discerned through the method of the invention can also be derivatized in various ways. For example, if the aptamer is to be used for separation of the target substance, conventionally the oligonucleotide will be derivatized to a solid support to permit chromatographic separation. If the oligonucleotide is to be used to label cellular components or otherwise for attaching a detectable moiety to target, the oligonucleotide will be derivatized to include a radionuclide, a fluorescent molecule, a chromophore or the like. If the oligonucleotide is to be used in specific binding assays, coupling to solid support or detectable label is also desirable. If it is to be used therapeutically, the oligonucleotide may be derivatized to include ligands which permit easier transit of cellular barriers, toxic moieties which aid in the therapeutic effect, or enzymatic activities which perform desired functions at the targeted site. The aptamer may also be included in a suitable expression system to provide for in situ generation of the desired sequence.

The oligonucleotides used as starting materials in the process of the invention to determine specific binding sequences may be single-stranded or double-stranded DNA or RNA. In embodiments of this invention, the sequences are single-stranded RNA.

In aspects of the invention, the aptamer specifically targets antigens specific to cancer cells, which are also known as cancer antigens or tumor antigens. Such antigens are well known in the art, and it is within the skill of the ordinary artisan to select the appropriate cancer antigen for use with a specific cancer. For example, as described in detail herein, the aptamer in an aptamer-inhibitory nucleic acid chimera can be specific to PSMA. Other illustrative non-limiting examples of aptamer targeted cancer cell antigens includes Muc1, HER2, TGFbeta-receptor, Guanylyl cyclase C (GC-C), and PSCA.

Inhibitory Nucleic Acids

Inhibitory nucleic acid molecules are those oligonucleotides that inhibit the expression or activity of a target gene in a cancer cell, wherein such inhibition results in the cancer cell becoming radiosensitized. Such oligonucleotides include single and double stranded nucleic acid molecules (e.g., DNA, RNA, and analogs thereof) that bind a nucleic acid molecule that encodes a target radiosensitivity protein (e.g., antisense molecules, siRNA, shRNA) as well as nucleic acid molecules that bind directly to a radiosensitivity protein and thereby modulate its biological activity.

shRNA

Small hairpin RNAs consist of a stem-loop structure with optional 3' UU-overhangs. A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The term "hairpin" is also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The multiple stem-loop structures can be linked to one another through a linker, such as, for example, a nucleic acid linker, a miRNA flanking sequence, other molecule, or some combination thereof.

While there may be variation, stems can range from 21 to 31 bp (e.g., 25 to 29 bp), and the loops can range from 4 to 30 bp (desirably 4 to 23 bp). For expression of shRNAs within cells, any method well known in the art for introducing a nucleic acid construct into cells can be employed. A non-limiting example includes use of plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the poly-thymidine tract, and the transcript is typically cleaved after the second uridine. Cleavage at this position generates a 3' UU overhang in the expressed shRNA, which is similar to the 3' overhangs of synthetic siRNAs. Furthermore, as described herein, shRNAs may be covalently linked to aptamers to generate the aptamer-shRNA chimeras of the invention.

shRNA also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. In some instances the precursor miRNA molecule can include more than one stem-loop structure. MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Thus, one of ordinary skill in the art can readily design and express artificial miRNAs based on the features of existing miRNA genes.

siRNA

Short twenty-one to twenty-five nucleotide double-stranded RNAs are effective at down-regulating gene expression (Zamore et al., Cell 101: 25-33; Elbashir et al., Nature 411: 494-498, 2001, each of which is hereby incorporated by reference). The therapeutic effectiveness of an siRNA in vivo is well known in the art (see McCaffrey et al, (Nature 418: 38-39.2002), which is hereby incorporated by reference). Given the sequence of a target gene, siRNAs may be designed to inactivate that gene. Such siRNAs, for example, could be administered directly to an affected tissue, or administered systemically. The nucleic acid sequence of a gene can be used to design small interfering RNAs (siRNAs) for that gene. The 21 to 25 nucleotide siRNAs may be used, for example, when screening for additional target genes the inhibition of which would radiosensitize a cancer cell. Further, as described herein, siRNA may be coupled with an aptamer to deliver the siRNA to a cancer cell.

Ribozymes

Catalytic RNA molecules or ribozymes that target an antisense target sequence of the present invention can be used to inhibit expression of a target gene nucleic acid molecule in vivo, wherein inhibition of the target gene sensitizes the cancer cell to radiation. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In embodiments of this invention, the catalytic nucleic acid molecule is formed in a hammerhead or hairpin motif. Examples of such hammerhead motifs are well known in the art (see Rossi et al., Aids Research and Human Retroviruses, 8:183, 1992, which is hereby incorporate by reference). Example of hairpin motifs are also well known in the art (see Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990, each of which is hereby incorporated by reference). These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Further, catalytic RNAs of the invention may be covalently linked to an aptamer wherein the aptamer delivers the catalytic RNA to a cancer cell and the catalytic RNA inhibits the production of a target protein and thereby radiosensitizes the cancer cell.

The inhibitory nucleic acid molecules of the present invention may be employed as double-stranded RNAs for RNA interference (RNAi)-mediated knock-down of the expression of a target radiosensitivity protein. In one embodiment, DNAPK expression is reduced in a prostate cancer cell. RNAi is a method for decreasing the cellular expression of specific proteins of interest (reviewed in Tuschl, Chembiochem 2:239-245, 2001; Sharp, Genes & Devel, 15:485-490, 2000; Hutvagner and Zamore, Curr. Opin. Genet. Devel. 12:225-232, 2002; and Hannon, Nature 418:244-251, 2002).

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

In aspects of the invention, shRNA are coupled with an aptamer to deliver the shRNA to a cancer cell.

Pharmaceutical Compositions

For therapeutic uses, the compositions or agents identified using the methods disclosed herein may be administered systemically, for example, formulated in a pharmaceutically-acceptable carrier. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a radiosensitizing aptamer-inhibitory nucleic acid (e.g., shRNA) chimeric therapeutic in a physiologically-acceptable carrier. Suitable carriers and their formulation are described, for example, in Remington's Pharmaceutical Sciences by E. W. Martin. The amount of the therapeutic aptamer-inhibitory nucleic acid (e.g., shRNA) chimera to be administered varies depending upon the manner of administration, the age and body weight of the patient, and the clinical symptoms of the cancer. Generally, amounts will be in the range of those used for other agents used in the treatment of cancer, although in certain instances lower amounts will be needed because of the increased specificity of the compound. A compound is administered at a dosage that radiosenitizes a cancer cell as determined by a diagnostic method known to one skilled in the art, or using any assay that measures sensitivity to ionizing radiation (e.g., induction of apoptosis).

Formulation of Pharmaceutical Compositions

The administration of an agent of the invention or analog thereof for the treatment of cancer may be by any suitable means that results in a concentration of the therapeutic that, combined with ionizing radiation, is effective in ameliorating, reducing, or stabilizing cancer or a symptom thereof. In one embodiment, administration of the agent and ionizing radiation results in an increase in apoptosis of the cancer cells. In another embodiment, the agent and ionizing radiation results in an increase in the average survival time or quality of life of the subject.

Methods of administering such agents are known in the art. The invention provides for the therapeutic administration of an agent by any means known in the art. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. In embodiments, the therapeutic composition is administered directly to the cancer mass. In related embodiments, the therapeutic composition is administered directly to the prostate of a subject. The pharmaceutical compositions may be formulated according to conventional pharmaceutical practice (see, e.g., Remington: The Science and Practice of Pharmacy (20th ed.), ed. A. R, Gennaro, Lippincott Williams & Wilkins, 2000 and Encyclopedia of Pharmaceutical Technology, eds. J. Swarbrick and J. C. Boylan, 1988-1999, Marcel Dekker, New York). Suitable formulations include forms for oral administration, depot formulations, formulations for delivery by a patch, semisolid dosage forms to be topically or transdermally delivered.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target cancer by using carriers or chemical derivatives to deliver the therapeutic agent to a particular cell type (e.g., prostate cancer cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra. Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active therapeutic (s), the composition may include suitable parenterally acceptable carriers and/or excipients.

The active therapeutic (s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active therapeutic(s) are dissolved or suspended in a parenterally acceptable liquid vehicle.

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Therapeutic Methods

The present invention provides methods of treating cancer by increasing the cancer's sensitivity to ionizing radiation, and exposing the cancer to ionizing radiation when the cancer is in the sensitive state. The methods comprise administering a therapeutically effective amount of a pharmaceutical composition comprising an aptamer-inhibitory nucleic acid (e.g., shRNA) chimera. Not wishing to be bound by any theory, it is believed that the aptamer portion delivers the aptamer-inhibitory nucleic acid (e.g., shRNA) chimera to a cancer cell; the shRNA portion enters the cell, is processed to an siRNA that knocks-down the levels of a target protein; and knock-down of the target protein results in the sentization of the cancer cell to ionizing radiation. Once the cancer cell has been sensitized to ionizing radiation the cancer is exposed to therapeutic amounts of ionizing radiation.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g., opinion) or objective (e.g., measurable by a test or diagnostic method).

The therapeutic methods of the invention, which include prophylactic treatment, in general comprise administration of a therapeutically effective amount of the agent herein to a subject (e.g., animal, human) in need thereof, including a mammal, e.g., a human.

Combination Therapies

The present invention also provides combination therapies. The chimeric aptamers of the present invention are suitable for use in combination with other chemotherapeutics, including, but not limited to, an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs well known in the art. Further, the chimeric aptamers can be used with a cancer treatment adjunct, such as a leucopenia (neutrophenia) treatment drug, thrombocytopenia treatment drug, antiemetic and cancer pain intervention drug, or combinations thereof.

In aspects, the chimeric aptamers can be used with other immunomodulators. Immunomodulators are well known in the art. Examples of the immunomodulator include, but are not limited to, various cytokines that stimulate immune responses such as GM-CSF, M-CSF, G-CSF, interferon-α, β, or γ, IL-1, IL-2, IL-3 and IL-12.

In other aspects, the chimeric aptamers can be used with targeted radiation-therapeutics such as radio-labeled antibodies (e.g., $I^{131}$, $Bi^{213}$, or $Y^{90}$) or radioactive substances that are taken up by bone (e.g., MDP). In addition, the chimeric aptamers can be used in combination with radiation mimetic drugs such as bleomycin or neocarzinostatin.

Kits

The invention provides kits for the treatment or amelioration of cancer or its symptoms. In one embodiment, the kit includes a therapeutic or prophylactic composition containing an effective amount of an agent of the invention (e.g., aptamer-inhibitory nucleic acid chimera) in unit dosage form. In embodiments, the kit comprises a container which contains a therapeutic or prophylactic compound; such containers can be sterile, and such containers can be in the form of boxes, ampoules, bottles, vials, tubes, bags, pouches, blister-packs, and the like. Such containers can be made of plastic, glass, laminated paper, metal foil, or other materials suitable for holding medicaments.

If desired, an agent of the invention is provided together with instructions for administering it to a subject having cancer. The instructions will generally include information about the use of the composition for the treatment of cancer. In other embodiments, the instructions include at least one of the following: description of the compound; dosage schedule and administration for treatment of cancer or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Neovascularization

Angiogenesis is the growth of new blood vessels from pre-existing vessels. Angiogenesis plays a critical role in tumor formation and is essential for growth of tumors beyond 1 mm in diameter. Tumor-associated neovascular endothelial cells express antigens that can serve as targets for the claimed aptamer-inhibitory nucleic acid chimeras. For example, tumor-associate neovascular endothelia cells express prostate-specific membrane antigen (PSMA). (Chang et al., Five different anti-prostate-specific membrane antigen (PSMA) antibodies cofirm PSMA expression in tumor-associated neovasculature, *Cancer Res.*, vol. 59, pages 3192-3198). In one aspect of the invention, methods are provided for targeting neoplasia associated neovascularization by contacting neovascular endothelia cells with aptamer-inhibitory nucleic acid chimeras and exposing neovascular endothelia cells to ionizing radiation.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the agents and therapeutic methods of the invention, and are not intended to limit the scope of what the inventors regard as their invention.

EXAMPLES

It should be appreciated that the invention should not be construed to be limited to the examples that are now described; rather, the invention should be construed to include any and all applications provided herein and all equivalent variations within the skill of the ordinary artisan.

Example 1

Identification of siRNAs that Radiosensitize a Cell

Figure 1:
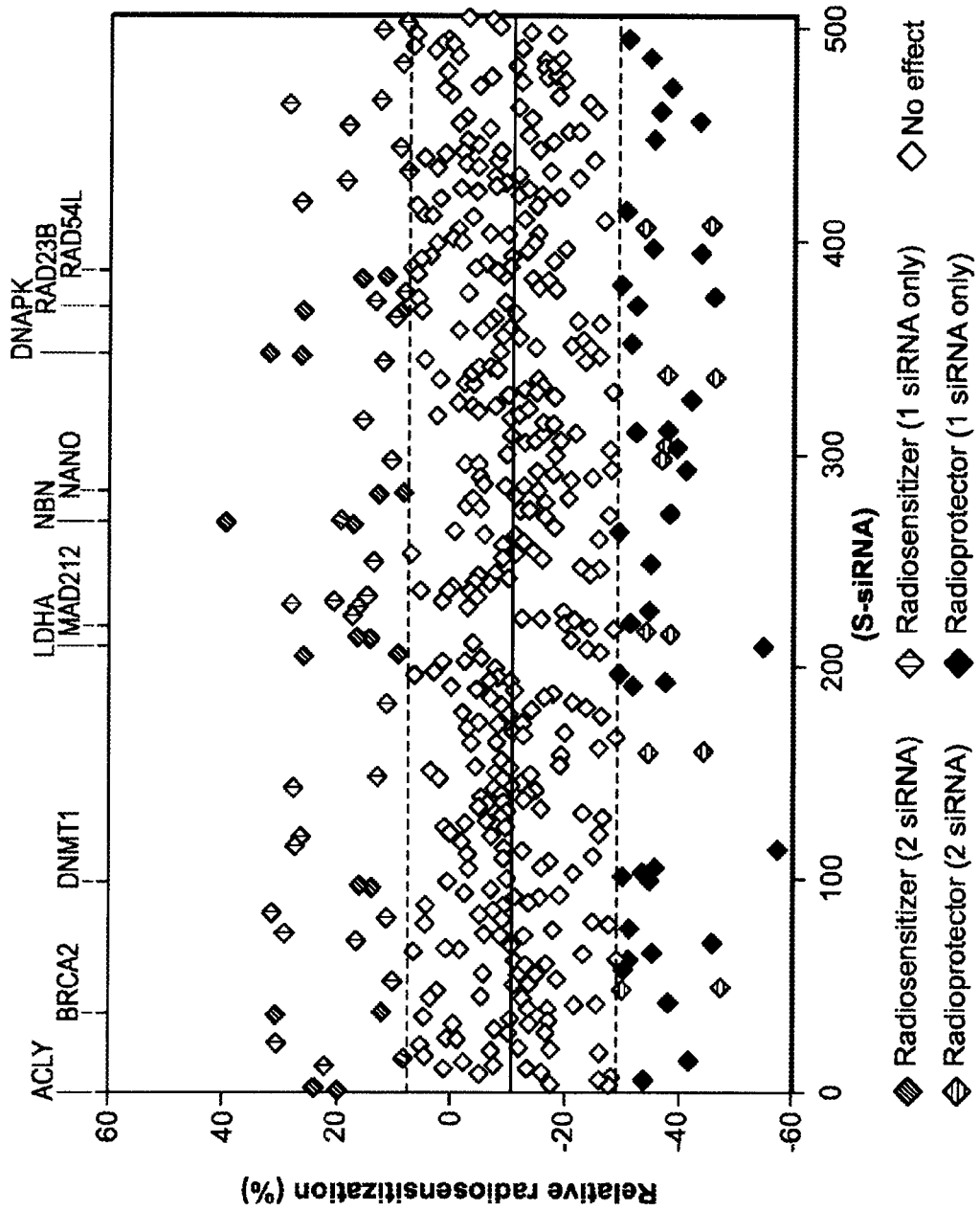
FIG. 1 is a plot showing the results of a screen for radiosensitization target genes and their cognate siRNAs. An siRNA library screen for candidate radiosensitization targets was carried out in DU145 cells. Cells were transfected with library siRNAs or controls. Transfected cells were untreated or irradiated (6 Gy) 72 hours later. Radiosensitization was calculated as percent increased cell death associated with a gene-specific siRNA after radiation therapy compared with irradiated cells transfected with a control siRNA. Each diamond represents an siRNA (triplicate, average) organized alphabetically. Mean library radiosensitization and SD are shown by solid and dashed lines, respectively.
Figure 4:
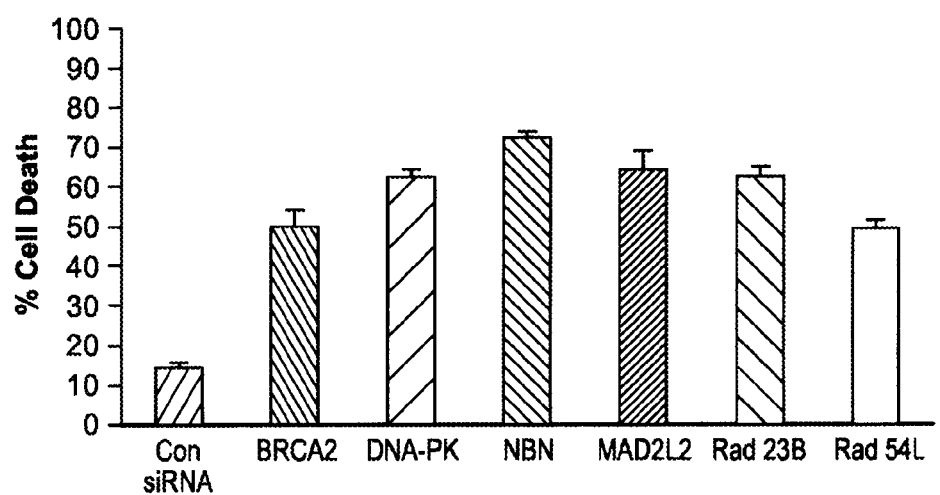
FIG. 4 is a graph showing the results of siRNA-mediated radiation sensitization of a panel of radiosensitization target genes. LNCaP cells were seeded in 6-well plates at $2\times10^5$ cells per well. After 24 hours, cells were either transfected with 100 nM of DNA-PK, BRCA2, NBN, MAD2L2, RAD23B, RAD54L siRNAs or control siRNAs separately using HiPerfectTransfection Reagent. 48 hours later, cells were seeded in 96 well plate at 2000 cells per well. 24 hours later, cells were then irradiated with Gy IR using a Gammacell 40 (Nordion, Ottawa, ONT, Canada) 137Cs radiator at approximately 0.6 Gy/min. Cell viability was assessed after 12 days by MTS. means±S.E.M, n=3.

To explore the combination of IR with siRNA, a custom siRNA library was screened against 249 mRNAs, primarily encoding critical DNA repair proteins. The goal was to identify radiosensitizing target genes and corresponding siRNAs. Radiosensitization was calculated as percent increased cell death associated with a gene-specific siRNA after radiation therapy (6 Gy) compared with irradiated cells transfected with a control siRNA. Candidate targets were defined as those for which 2 separate siRNAs, targeting the same gene, enhanced radiation-induced cell death above the SD of the library mean (FIG. 1 and Table 1). In total, 10 candidate genes were identified as PCa radiosensitization targets, 6 of which were separately confirmed by clonogenic survival assays (FIG. 2). Effective target gene knockdown at the time of irradiation was confirmed by quantitative RT-PCR (qRT-PCR; FIG. 3). The dose-modifying factor ($DMF_{0.1}$) was calculated for each target as the ratio of IR dose required for 90% cell kill by control siRNA versus gene-specific siRNA, and 3 target genes—specifically, the catalytic subunit of DNA-activated protein kinase, catalytic polypeptide (DNAPK); mitotic spindle assembly checkpoint protein MAD2B (MAD2L2); and breast cancer type 2 susceptibility protein (BRCA2)-achieved $DMF_{0.1}$ of 1.6 by siRNA inhibition. The remaining 3 target genes achieved $DMF_{0.1}$ of 1.3 in clonogenic survival assays. All 6 candidate genes were verified as radiosensitizing targets in a second cell line, the PSMA-positive cell and tumor model LNCaP (FIG. 4). Interestingly, the siRNA screen primarily identified genes involved in DSB repair, except RAD23B, a gene involved in excision repair (Mu D, Hsu D S, Sancar A. Reaction mechanism of human DNA repair excision nuclease. *J Biol. Chem.* 1996; 271(14): 8285-8294).

TABLE 1

|  | 0 Gy Avg | 0 Gy St dev | 6 Gy Avg | 6 Gy St dev | Relative Sensitization |
| --- | --- | --- | --- | --- | --- |
| control siRNA | 1 | 0.124472004 | 1 | 0.094211712 | 0.00% |
| ACLY | 1.860022981 | 0.121168192 | 1.495426898 | 0.442145785 | 19.60% |
| ACLY | 1.336293046 | 0.125416099 | 1.016535256 | 0.152135228 | 23.93% |
| AHCY | 1.647376301 | 0.074640222 | 2.111917098 | 0.261125426 | 28.20% |
| AHCY | 2.065322609 | 0.029588199 | 2.424329804 | 0.104705175 | 17.38% |
| AKT1 | 1.026513645 | 0.043308969 | 1.297762747 | 0.15662083 | 26.42% |
| AKT1 | 1.165931683 | 0.039687706 | 1.559469303 | 0.020034444 | −33.75% |
| AKT2 | 1.062967649 | 0.05816065 | 1.359677419 | 0.119615338 | 27.91% |
| AKT2 | 1.220621724 | 0.177839016 | 1.418938606 | 0.023089508 | 16.25% |
| ALKBH2 | 0.992821292 | 0.041468292 | 1.044196918 | 0.198307671 | 5.17% |
| ALKBH2 | 1.134315823 | 0.090214712 | 1.2873918 | 0.182010182 | 13.50% |
| ALKBH3 | 1.840593335 | 0.072838311 | 1.821536382 | 0.208577626 | 1.04% |
| ALKBH3 | 0.654305512 | 0.097023714 | 0.509484118 | 0.060718889 | 22.13% |
| APEX1 | 0.758026278 | 0.040990649 | 0.815590223 | 0.027601053 | 7.59% |
| APEX1 | 0.826198015 | 0.027713131 | 0.846079577 | 0.040360728 | 2.41% |
| APEX1 | 1.019446955 | 0.078334922 | 1.447086368 | 0.062142199 | −41.95% |
| APEX2 | 0.99622068 | 0.166587825 | 0.913306046 | 0.090975723 | 8.32% |
| APEX2 | 1.077546042 | 0.066916344 | 1.029546624 | 0.234397258 | 4.45% |
| AR | 1.057364902 | 0.108014404 | 1.334313215 | 0.051292945 | 26.19% |
| AR | 0.826369058 | 0.078424208 | 0.969927159 | 0.058317607 | 17.37% |
| ARMET | 0.464436401 | 0.041606696 | 0.499541479 | 0.035553201 | 7.56% |
| ARMET | 1.083684937 | 0.078618231 | 1.215325773 | 0.059524345 | 12.15% |
| ATM | 1.811971169 | 0.297400989 | 1.717774273 | 0.609641954 | 5.20% |
| ATM | 1.879487447 | 0.047891941 | 1.301148907 | 0.172167965 | 30.77% |
| ATR | 0.827678681 | 0.021027422 | 0.839313521 | 0.253657593 | 1.41% |
| ATR | 1.139033091 | 0.041048611 | 1.133949574 | 0.102873886 | 0.45% |
| BIRC2 | 1.041596304 | 0.044036623 | 1.047771889 | 0.067265294 | 0.59% |
| BIRC2 | 0.689337914 | 0.103040786 | 0.686322809 | 0.037473851 | 0.44% |
| BIRC4 | 1.093635358 | 0.028595307 | 1.275185987 | 0.125032344 | 16.60% |
| BIRC4 | 1.212271201 | 0.150139005 | 1.339478988 | 0.04263207 | 10.49% |
| BIRC5 | 0.965236126 | 0.037132307 | 1.044786146 | 0.021190889 | 8.24% |
| BIRC5 | 1.152700945 | 0.045995234 | 1.30989525 | 0.031959076 | 13.64% |

TABLE 1-continued

|  | 0 Gy Avg | 0 Gy St dev | 6 Gy Avg | 6 Gy St dev | Relative Sensitization |
|---|---|---|---|---|---|
| BLM | 0.838862632 | 0.026110645 | 0.843013703 | 0.118823653 | 0.49% |
| BLM | 0.731519295 | 0.04504036 | 0.857191253 | 0.005359138 | 17.18% |
| BRCA1 | 0.933036602 | 0.04001633 | 1.032488101 | 0.024911891 | 10.66% |
| BRCA1 | 0.891096529 | 0.036928642 | 0.850381964 | 0.030689307 | 4.57% |
| BRCA2 | 1.963229917 | 0.170562503 | 1.35791845 | 0.222474753 | 30.83% |
| BRCA2 | 1.704899196 | 0.066633739 | 1.498715927 | 0.254634012 | 12.09% |
| C18orf37 | 1.001514005 | 0.113452665 | 1.140479212 | 0.19351858 | 13.88% |
| C18orf37 | 0.819561715 | 0.067014617 | 0.959145082 | 0.072471853 | 17.03% |
| CANX | 1.552491382 | 0.344356396 | 1.886911467 | 0.886718735 | 21.54% |
| CANX | 1.215057203 | 0.01066571 | 1.524633072 | 0.071152097 | 25.48% |
| CARM1 | 0.526865164 | 0.051063897 | 0.72835447 | 0.41977691 | −38.24% |
| CARM1 | 1.064868324 | 0.032061914 | 1.198975598 | 0.049979816 | 12.59% |
| CBX3 | 1.207602411 | 0.028772199 | 1.164993539 | 0.165527336 | 3.53% |
| CBX3 | 0.950717211 | 0.035486509 | 1.000646911 | 0.120997246 | 5.25% |
| CCNH | 1.123477774 | 0.141124798 | 1.094947326 | 0.152009453 | 2.54% |
| CCNH | 1.098082345 | 0.0691399 | 1.069784607 | 0.112084229 | 2.58% |
| CCT4 | 0.405966926 | 0.021478927 | 0.527947393 | 0.083764296 | −30.05% |
| CCT4 | 0.294367014 | 0.011728925 | 0.43405131 | 0.051809487 | −47.45% |
| CCT5 | 1.010978024 | 0.037455863 | 1.12570176 | 0.0223163 | 11.35% |
| CCT5 | 0.381291368 | 0.065450694 | 0.434632848 | 0.06932378 | 13.99% |
| CDC2 | 1.306876615 | 0.110871263 | 1.173740185 | 0.011830356 | 10.19% |
| CDC2 | 0.578121415 | 0.052542672 | 0.685739452 | 0.015592135 | 18.62% |
| CDK7 | 1.484940283 | 0.19507667 | 1.660103627 | 0.105763156 | 11.80% |
| CDK7 | 0.623245935 | 0.11527591 | 0.65857175 | 0.076873494 | 5.67% |
| CDKN1A | 1.100953046 | 0.028537044 | 1.264711005 | 0.090780349 | 14.87% |
| CDKN1A | 1.128535104 | 0.014977281 | 1.305665447 | 0.092554062 | 15.70% |
| CDKN2A | 0.877570938 | 0.145223487 | 1.143704475 | 0.042522887 | −30.33% |
| CDKN2A | 0.778022772 | 0.104083061 | 0.88371488 | 0.097923994 | 13.58% |
| CDKN2B | 1.116985966 | 0.033413553 | 1.305789853 | 0.035445274 | 16.90% |
| CDKN2B | 1.097556241 | 0.077339843 | 1.221293324 | 0.03406237 | 11.27% |
| CDKN2C | 1.088782779 | 0.082766972 | 1.427483765 | 0.158641889 | −31.11% |
| CDKN2C | 1.194103146 | 0.075179945 | 1.537956259 | 0.098110371 | 28.80% |
| CDKN2D | 0.572041383 | 0.033747449 | 0.705033465 | 0.0791769 | 23.25% |
| CDKN2D | 1.117529455 | 0.106303492 | 1.512876017 | 0.154025732 | −35.38% |
| CDKN3 | 1.163690536 | 0.043745101 | 1.085933481 | 0.142287485 | 6.68% |
| CDKN3 | 0.719730449 | 0.037050282 | 0.728734707 | 0.213212127 | 1.25% |
| CETN2 | 0.623747687 | 0.06176773 | 0.616511679 | 0.052325066 | 1.16% |
| CETN2 | 0.930421083 | 0.084747927 | 1.028270407 | 0.02810361 | 10.52% |
| CHEK1 | 0.991817264 | 0.142118845 | 1.447037621 | 0.830679326 | −45.90% |
| CHEK1 | 1.002715972 | 0.03867027 | 0.836629872 | 0.029912339 | 16.56% |
| CHEK2 | 1.28579161 | 0.105754821 | 1.399794586 | 0.037026965 | 8.87% |
| CHEK2 | 0.720797198 | 0.041990255 | 0.814099632 | 0.047447296 | 12.94% |
| CKS2 | 1.811205126 | 0.194266251 | 1.917503942 | 0.247453229 | 5.87% |
| CKS2 | 1.46840071 | 0.068376853 | 1.039062852 | 0.16501012 | 29.24% |
| CLU | 1.138744929 | 0.079983171 | 1.345226543 | 0.0921184 | 18.13% |
| CLU | 1.067741998 | 0.151957353 | 1.400636959 | 0.095978125 | −31.18% |
| COL1A2 | 0.359429204 | 0.053593975 | 0.458834443 | 0.011955923 | 27.66% |
| COL1A2 | 1.266232009 | 0.094068616 | 1.210780903 | 0.181226478 | 4.38% |
| COPB2 | 0.239756844 | 0.037202802 | 0.299693574 | 0.054748087 | 25.00% |
| COPB2 | 1.149373113 | 0.048861171 | 1.251403521 | 0.034123819 | 8.88% |
| CRIP2 | 0.652390404 | 0.139328733 | 0.577607569 | 0.146551051 | 11.46% |
| CRIP2 | 1.095512621 | 0.068560075 | 1.149935575 | 0.109379194 | 4.97% |
| DCLRE1A | 1.591281033 | 0.111652076 | 1.091732372 | 0.418836143 | 31.39% |
| DCLRE1A | 1.052335445 | 0.05026272 | 1.12643005 | 0.040626099 | 7.04% |
| DCLRE1B | 0.833270011 | 0.105735905 | 0.906439419 | 0.111711577 | 8.78% |
| DCLRE1B | 0.685756564 | 0.043878988 | 0.654767496 | 0.136268103 | 4.52% |
| DCLRE1C | 0.993012287 | 0.055026948 | 1.133835933 | 0.175782264 | 14.18% |
| DCLRE1C | 1.005726043 | 0.097130704 | 1.145355925 | 0.128195999 | 13.88% |
| DDB1 | 0.770155555 | 0.039104923 | 0.851262767 | 0.012161393 | 10.53% |
| DDB1 | 0.856499544 | 0.079866395 | 0.988878107 | 0.085105856 | 15.46% |
| DDB2 | 1.157631626 | 0.048063944 | 1.282426357 | 0.041339678 | 10.78% |
| DDB2 | 1.0688876 | 0.068378244 | 1.271354761 | 0.058499126 | 18.94% |
| DMC1 | 1.033828469 | 0.072739098 | 1.060052321 | 0.022626912 | 2.54% |
| DMC1 | 1.033586095 | 0.055406574 | 1.105989614 | 0.035412173 | 7.01% |
| DNMT1 | 1.735506111 | 0.026980137 | 1.486776301 | 0.172839324 | 14.33% |
| DNMT1 | 1.533166197 | 0.172790108 | 1.286821356 | 0.450139636 | 16.07% |
| DNMT3A | 0.745025161 | 0.032365367 | 0.74117926 | 0.015546111 | 0.52% |
| DNMT3A | 0.821945885 | 0.076881199 | 0.901400816 | 0.046183218 | 9.67% |
| DNMT3A | 1.094108079 | 0.145429841 | 1.472372529 | 0.0492144 | −34.57% |
| DNMT3B | 1.043382053 | 0.091970002 | 1.356821179 | 0.129786815 | −30.04% |
| DNMT3B | 0.959238339 | 0.035026724 | 1.163096216 | 0.206177031 | 21.25% |
| DOT1L | 0.583786444 | 0.025379453 | 0.780671239 | 0.192908096 | −33.73% |
| DOT1L | 1.264805019 | 0.061232483 | 1.299605738 | 0.091357589 | 2.75% |
| DUT | 1.10487393 | 0.037379504 | 1.497847777 | 0.123138745 | −35.57% |
| DUT | 0.792367864 | 0.048672338 | 0.918140877 | 0.177527823 | 15.87% |
| DVL3 | 0.405515512 | 0.033604624 | 0.807163776 | 0.447926414 | −99.05% |
| DVL3 | 0.980367716 | 0.064516677 | 1.146382414 | 0.082073988 | 16.93% |
| E2F5 | 1.061978463 | 0.080035003 | 1.159404162 | 0.06011161 | 9.17% |

TABLE 1-continued

| | 0 Gy Avg | 0 Gy St dev | 6 Gy Avg | 6 Gy St dev | Relative Sensitization |
|---|---|---|---|---|---|
| E2F5 | 1.156427726 | 0.059250675 | 1.443308203 | 0.064070848 | 24.81% |
| EHMT1 | 0.892199404 | 0.038581048 | 0.918137288 | 0.168632819 | 2.91% |
| EHMT1 | 0.76504688 | 0.036265048 | 0.84316615 | 0.105879905 | 10.21% |
| EIF4A3 | 0.195084885 | 0.023282535 | 0.219374175 | 0.014285702 | 12.45% |
| EIF4A3 | 0.267511379 | 0.011053333 | 0.420766657 | 0.064542057 | −57.29% |
| ERCC1 | 0.392806156 | 0.075434221 | 0.429691372 | 0.074023734 | 9.39% |
| ERCC1 | 1.744733452 | 0.185704447 | 1.267447623 | 0.342173015 | 27.36% |
| ERCC2 | 0.786482816 | 0.218273403 | 0.800450552 | 0.333277067 | 1.78% |
| ERCC2 | 0.961999238 | 0.043331064 | 1.025028308 | 0.065354518 | 6.55% |
| ERCC3 | 0.53626519 | 0.16759708 | 0.39288128 | 0.079007759 | 26.74% |
| ERCC3 | 0.856012603 | 0.069645025 | 0.913240405 | 0.059447555 | 6.69% |
| ERCC4 | 1.017000796 | 0.063861889 | 1.283862403 | 0.134446188 | 26.24% |
| ERCC4 | 1.060316471 | 0.060040828 | 1.061301784 | 0.090313161 | 0.09% |
| ERCC5 | 0.998164548 | 0.031775952 | 1.090282365 | 0.039962071 | 9.23% |
| ERCC5 | 0.987503633 | 0.008047825 | 0.978894592 | 0.077568635 | 0.87% |
| ERCC6 | 0.920310931 | 0.046930892 | 0.990726641 | 0.012528521 | 7.65% |
| ERCC6 | 0.923288667 | 0.029801806 | 0.946897817 | 0.056996782 | 2.56% |
| ERCC8 | 0.863625935 | 0.009022114 | 0.915053272 | 0.10272711 | 5.95% |
| ERCC8 | 0.96050001 | 0.06268134 | 1.215247195 | 0.160933046 | 26.52% |
| EXO1 | 0.785190963 | 0.010413493 | 0.86552501 | 0.096729266 | 10.23% |
| EXO1 | 0.835987091 | 0.037022998 | 0.908938462 | 0.109179185 | 8.73% |
| EZH2 | 1.357805388 | 0.025484382 | 1.674783819 | 0.106377867 | 23.34% |
| EZH2 | 1.125274171 | 0.044033774 | 1.231793188 | 0.064529549 | 9.47% |
| FANCA | 0.921970535 | 0.091443109 | 1.06678112 | 0.124781298 | 15.71% |
| FANCA | 0.877016246 | 0.152461723 | 0.922047225 | 0.075566524 | 5.13% |
| FANCC | 0.867300301 | 0.013956345 | 0.945706923 | 0.102383262 | 9.04% |
| FANCC | 1.012032132 | 0.056223141 | 1.073991644 | 0.032935617 | 6.12% |
| FANCD2 | 0.867092552 | 0.148666839 | 0.977216821 | 0.05624289 | 12.70% |
| FANCD2 | 1.034065102 | 0.064945126 | 1.093802095 | 0.063329712 | 5.78% |
| FANCE | 0.990079983 | 0.022110333 | 1.122779275 | 0.057955865 | 13.40% |
| FANCE | 1.078944635 | 0.05420914 | 1.17105931 | 0.106630156 | 8.54% |
| FANCF | 0.876489393 | 0.045808435 | 1.004861358 | 0.043934195 | 14.65% |
| FANCF | 0.888939874 | 0.054700626 | 0.958432847 | 0.037646362 | 7.82% |
| FANCG | 1.039463649 | 0.05237549 | 0.751350098 | 0.040050399 | 27.72% |
| FANCG | 1.138147374 | 0.09357871 | 1.254812312 | 0.084518567 | 10.25% |
| FAP | 0.783324921 | 0.092675649 | 0.8783528 | 0.034157238 | 12.13% |
| FAP | 0.934107282 | 0.066698723 | 1.015109169 | 0.053117056 | 8.67% |
| FEN1 | 1.956370347 | 0.101173521 | 1.916197342 | 0.327589619 | 2.05% |
| FEN1 | 0.9836917 | 0.039574795 | 0.856409355 | 0.080129664 | 12.94% |
| FLJ35220 | 0.909145138 | 0.090843227 | 1.037163135 | 0.021970932 | 14.08% |
| FLJ35220 | 0.892304869 | 0.044923291 | 0.961159951 | 0.038823588 | 7.72% |
| G3BP1 | 1.152515685 | 0.131429656 | 1.113507604 | 0.060789059 | 3.38% |
| G3BP1 | 1.137040226 | 0.01768681 | 1.253652718 | 0.04649044 | 10.26% |
| GTF2H1 | 1.028694835 | 0.006924532 | 1.075376322 | 0.043473843 | 4.54% |
| GTF2H1 | 1.201796039 | 0.104581252 | 1.431037339 | 0.059869531 | 19.07% |
| GTF2H2 | 1.024306638 | 0.079546063 | 1.116590528 | 0.076126393 | 9.01% |
| GTF2H2 | 0.900765209 | 0.072862706 | 0.978856741 | 0.035748865 | 8.67% |
| GTF2H3 | 1.264952639 | 0.094175773 | 1.507106649 | 0.019866063 | 19.14% |
| GTF2H3 | 1.121294132 | 0.027453019 | 1.338203625 | 0.196008137 | 19.34% |
| GTF2H4 | 0.827905295 | 0.15953647 | 1.114360042 | 0.056431067 | −34.60% |
| GTF2H4 | 0.958792698 | 0.03563308 | 1.38280437 | 0.024077758 | −44.22% |
| H2AFX | 0.909705991 | 0.791921993 | 1.579365868 | 0.180969505 | −73.61% |
| H2AFX | 1.433854103 | 0.068855513 | 1.807606931 | 0.036722217 | 26.07% |
| H2AFZ | 1.43657509 | 0.113374705 | 1.54629421 | 0.409551322 | 7.64% |
| H2AFZ | 1.892370904 | 0.085788012 | 1.956431629 | 0.470600702 | 3.39% |
| HDAC1 | 1.076726189 | 0.035884843 | 1.162361046 | 0.080159851 | 7.95% |
| HDAC1 | 1.378250707 | 0.121219923 | 1.776364179 | 0.029219212 | 28.89% |
| HDAC10 | 1.167302251 | 0.093962651 | 1.316469536 | 0.186286463 | 12.78% |
| HDAC10 | 1.265100258 | 0.040689297 | 1.405360633 | 0.063882576 | 11.09% |
| HDAC11 | 0.526505315 | 0.021192524 | 0.631193628 | 0.041775621 | 19.88% |
| HDAC11 | 1.048976836 | 0.056671452 | 1.080258483 | 0.137293172 | 2.98% |
| HDAC2 | 0.993750769 | 0.030449241 | 1.12066395 | 0.245415742 | 12.77% |
| HDAC2 | 1.390134088 | 0.062017949 | 1.54527383 | 0.113485364 | 11.16% |
| HDAC4 | 0.953083342 | 0.083100984 | 1.03145133 | 0.039446365 | 8.22% |
| HDAC4 | 0.918648939 | 0.080711928 | 0.964058412 | 0.062250727 | 4.94% |
| HDAC6 | 1.118438681 | 0.042367796 | 1.235008611 | 0.07702996 | 10.42% |
| HDAC6 | 1.164950309 | 0.070419053 | 1.199467669 | 0.164185371 | 2.96% |
| HLTF | 1.368384795 | 0.083804062 | 1.726567936 | 0.0217327 | 26.18% |
| HLTF | 0.986074548 | 0.070984414 | 1.009376139 | 0.074536946 | 2.36% |
| HNRNPA2B1 | 0.922302866 | 0.166113356 | 1.051784117 | 0.346638883 | 14.04% |
| HNRNPA2B1 | 1.235354902 | 0.105006002 | 1.528973263 | 0.123246142 | 23.77% |
| HSP90B1 | 1.770152164 | 0.100831368 | 1.929218292 | 0.6011219 | 8.99% |
| HSP90B1 | 0.687175737 | 0.133561854 | 0.609191259 | 0.048822099 | 11.35% |
| HSPD1 | 0.906482962 | 0.08775712 | 1.101746016 | 0.10132525 | 21.54% |
| HSPD1 | 1.05752245 | 0.040245058 | 1.131597257 | 0.144315988 | 7.00% |
| HSPE1 | 0.793203106 | 0.193945844 | 0.848884884 | 0.070819712 | 7.02% |
| HSPE1 | 0.651833281 | 0.040807423 | 0.75791845 | 0.098718014 | 16.27% |
| HUS1 | 2.100630245 | 0.106357851 | 2.471908087 | 0.44322413 | 17.67% |

TABLE 1-continued

| | 0 Gy Avg | 0 Gy St dev | 6 Gy Avg | 6 Gy St dev | Relative Sensitization |
|---|---|---|---|---|---|
| HUS1 | 0.966569717 | 0.050318208 | 1.073796416 | 0.053323535 | 11.09% |
| IARS | 1.631393851 | 0.211565456 | 1.701419239 | 0.097191131 | 4.29% |
| IARS | 1.405236951 | 0.173116431 | 1.407794548 | 0.334264592 | 0.18% |
| IFNGR2 | 0.535583595 | 0.452033381 | 0.707441455 | 0.54022995 | −32.09% |
| IFNGR2 | 1.027375072 | 0.135597374 | 1.136661522 | 0.008499378 | 10.64% |
| IGF1R | 0.939071022 | 0.080118676 | 1.292851633 | 0.2689938 | −37.67% |
| IGF1R | 1.283545876 | 0.239291152 | 1.374337538 | 0.055778733 | 7.07% |
| ILF2 | 0.763082645 | 0.053578429 | 0.826544991 | 0.029521512 | 8.32% |
| ILF2 | 1.015317243 | 0.022874379 | 0.949965331 | 0.056634536 | 6.44% |
| ITGB3 | 0.864865389 | 0.015373447 | 1.119827822 | 0.159795099 | −29.48% |
| ITGB3 | 0.709136435 | 0.167351123 | 0.687492225 | 0.169761376 | 3.05% |
| KDELR2 | 1.089923814 | 0.011828729 | 1.174998322 | 0.157686543 | 7.81% |
| KDELR2 | 1.15283249 | 0.023051809 | 1.13945738 | 0.094693411 | 1.16% |
| KIAA0101 | 1.125698118 | 0.039174475 | 1.104860352 | 0.167193939 | 1.85% |
| KIAA0101 | 0.991867078 | 0.125229112 | 0.975964768 | 0.098017306 | 1.60% |
| KPNA2 | 0.66307224 | 0.067796131 | 0.680810339 | 0.040902805 | 2.68% |
| KPNA2 | 0.856375901 | 0.019620509 | 0.900824906 | 0.031907025 | 5.19% |
| LDHA | 1.235070859 | 0.159647246 | 0.916062176 | 0.090692611 | 25.83% |
| LDHA | 1.583899161 | 0.114930832 | 1.439513404 | 0.210851066 | 9.12% |
| LIG1 | 1.316863401 | 0.218038446 | 1.658301419 | 0.344683257 | 25.93% |
| LIG1 | 1.817995056 | 0.116370189 | 2.256273936 | 0.168285885 | 24.11% |
| LIG3 | 0.515364744 | 0.014590155 | 0.797800086 | 0.066154726 | −54.80% |
| LIG3 | 0.312289334 | 0.02141388 | 0.582248285 | 0.056561565 | −86.45% |
| LIG4 | 1.188668258 | 0.218374363 | 1.233783683 | 0.058202656 | 3.80% |
| LIG4 | 1.134882276 | 0.031025365 | 1.376651489 | 0.108683022 | 21.30% |
| MAD2L2 | 1.131775126 | 0.100003295 | 0.969817447 | 0.080246876 | 14.31% |
| MAD2L2 | 0.584499938 | 0.097607811 | 0.488520028 | 0.078809175 | 16.42% |
| MAPK1 | 1.090312669 | 0.01643541 | 1.508818939 | 0.07590002 | −38.38% |
| MAPK1 | 1.149358395 | 0.021244124 | 1.542611863 | 0.020252454 | −34.22% |
| MBD1 | 1.032162891 | 0.033178014 | 1.324550272 | 0.193153997 | 28.33% |
| MBD1 | 0.825928298 | 0.009873938 | 1.0271205 | 0.178708358 | 24.36% |
| MBD2 | 0.884241604 | 0.132033611 | 1.060563894 | 0.149834619 | 19.94% |
| MBD2 | 1.020128496 | 0.065484971 | 1.340125899 | 0.125954093 | −31.37% |
| MBD3 | 0.712131816 | 0.033331493 | 0.867946051 | 0.051206979 | 21.88% |
| MBD3 | 0.882666995 | 0.200837669 | 1.022959944 | 0.051471831 | 15.89% |
| MBD4 | 1.103881301 | 0.046525652 | 1.240466125 | 0.053908808 | 12.37% |
| MBD4 | 0.94057725 | 0.053769515 | 0.775530599 | 0.063311909 | 17.55% |
| MCL1 | 0.904772996 | 0.055246785 | 1.083750093 | 0.151223466 | 19.78% |
| MCL1 | 1.134726994 | 0.056068185 | 1.530243089 | 0.118152703 | −34.86% |
| MCM3 | 1.123037853 | 0.164055084 | 1.152653828 | 0.271277652 | 2.64% |
| MCM3 | 0.900477914 | 0.074173861 | 0.750922633 | 0.220000661 | 16.61% |
| MECP2 | 1.028622167 | 0.156557379 | 0.739761207 | 0.07149122 | 28.08% |
| MECP2 | 1.138672484 | 0.098527939 | 1.118347585 | 0.264519109 | 1.78% |
| MGMT | 0.832090224 | 0.061160229 | 0.659307969 | 0.151432941 | 20.76% |
| MGMT | 0.937411095 | 0.031078032 | 0.971289192 | 0.030613894 | 3.61% |
| MLH1 | 1.341202688 | 0.12140842 | 1.141833746 | 0.296881041 | 14.86% |
| MLH1 | 1.042796302 | 0.064639691 | 1.075865839 | 0.134241881 | 3.17% |
| MLH3 | 1.026020567 | 0.076563554 | 1.017453438 | 0.105029182 | 0.83% |
| MLH3 | 0.926041342 | 0.041804849 | 0.87786498 | 0.024686386 | 5.20% |
| MLL | 0.937778186 | 0.038073653 | 0.936090926 | 0.047482141 | 0.18% |
| MLL | 0.984291592 | 0.013820563 | 1.0191236 | 0.021751586 | 3.54% |
| MMP9 | 1.013177628 | 0.139768588 | 1.053814668 | 0.194962418 | 4.01% |
| MMP9 | 1.036513428 | 0.079869992 | 1.105124248 | 0.144166699 | 6.62% |
| MMS19 | 1.009518287 | 0.0758167 | 1.110000224 | 0.155881203 | 9.95% |
| MMS19 | 0.997996299 | 0.039405677 | 1.075850738 | 0.061939209 | 7.80% |
| MNAT1 | 0.868856972 | 0.016039672 | 0.91034436 | 0.122152111 | 4.77% |
| MNAT1 | 0.955903272 | 0.03020709 | 1.031251588 | 0.022277812 | 7.88% |
| MPG | 1.127739281 | 0.025061122 | 1.396432037 | 0.17750059 | 23.83% |
| MPG | 1.004017935 | 0.024471619 | 1.260481202 | 0.195839574 | 25.54% |
| MRE11A | 0.756796654 | 0.137423182 | 0.929066031 | 0.060433439 | 22.76% |
| MRE11A | 1.056120064 | 0.060981219 | 1.422158169 | 0.127685446 | −34.66% |
| MRPL3 | 1.511925903 | 0.203105158 | 1.303717053 | 0.065137095 | 13.77% |
| MRPL3 | 0.79346283 | 0.082893271 | 0.921088595 | 0.034167244 | 16.08% |
| MRPS12 | 0.794995335 | 0.031077941 | 0.863983604 | 0.097011025 | 8.68% |
| MRPS12 | 0.67566038 | 0.022143849 | 0.751410133 | 0.075278165 | 11.21% |
| MSH2 | 1.048071347 | 0.059056559 | 0.974792547 | 0.045328435 | 6.99% |
| MSH2 | 0.97716411 | 0.060961516 | 1.115703773 | 0.187484054 | 14.18% |
| MSH3 | 0.849364634 | 0.087060425 | 0.950763344 | 0.074436738 | 11.94% |
| MSH3 | 1.096343617 | 0.035353941 | 1.234489087 | 0.092999264 | 12.60% |
| MSH4 | 0.98332814 | 0.032249944 | 1.071687947 | 0.023182138 | 8.99% |
| MSH4 | 0.865517122 | 0.030142067 | 0.979364336 | 0.092463868 | 13.15% |
| MSH5 | 0.997166094 | 0.028414811 | 1.120972357 | 0.127389282 | 12.42% |
| MSH5 | 1.033211048 | 0.07621348 | 1.30280411 | 0.030119616 | 26.09% |
| MSH6 | 0.963906497 | 0.033863944 | 1.069180702 | 0.190779091 | 10.92% |
| MSH6 | 0.928860949 | 0.05137645 | 0.981435371 | 0.081732297 | 5.66% |
| MTHFD2 | 0.64122458 | 0.138498582 | 0.828580375 | 0.116876916 | −29.22% |
| MTHFD2 | 0.848636791 | 0.15836051 | 0.851948637 | 0.059538097 | 0.39% |
| MUTYH | 0.982433665 | 0.11341215 | 1.162797641 | 0.169143086 | 18.36% |

TABLE 1-continued

| | 0 Gy Avg | 0 Gy St dev | 6 Gy Avg | 6 Gy St dev | Relative Sensitization |
|---|---|---|---|---|---|
| MUTYH | 0.648789767 | 0.081549299 | 0.768405862 | 0.110945125 | 18.44% |
| NBN | 1.493506041 | 0.211299898 | 1.236494706 | 0.429566775 | 17.21% |
| NBN | 0.865246004 | 0.405302674 | 0.523090786 | 0.046915698 | 39.54% |
| NCBP2 | 0.76796654 | 0.043102805 | 0.61892456 | 0.097193977 | 19.41% |
| NCBP2 | 1.132921835 | 0.072889009 | 1.321688935 | 0.00044993 | 16.66% |
| NEIL1 | 1.4067659 | 0.089279444 | 1.798562104 | 0.030132906 | 27.85% |
| NEIL1 | 1.366096691 | 0.146802815 | 1.891230163 | 0.109594132 | −38.44% |
| NEIL2 | 0.92867283 | 0.054608129 | 1.044941627 | 0.013051774 | 12.52% |
| NEIL2 | 1.065787196 | 0.119529982 | 1.215825231 | 0.105074406 | 14.08% |
| NEIL3 | 1.114399408 | 0.095004343 | 1.172068264 | 0.170227137 | 5.17% |
| NEIL3 | 0.815445326 | 0.012160387 | 0.837034402 | 0.005685218 | 2.65% |
| NFKB1 | 0.89081698 | 0.093046762 | 1.038117987 | 0.172160929 | 16.54% |
| NFKB1 | 1.267047109 | 0.196696199 | 1.311910627 | 0.108812065 | 3.54% |
| NME1 | 1.294944028 | 0.02940933 | 1.556969155 | 0.029324398 | 20.23% |
| NME1 | 1.270070119 | 0.074679937 | 1.41467051 | 0.071370835 | 11.39% |
| NONO | 1.21936697 | 0.183332247 | 1.063708042 | 0.193841121 | 12.77% |
| NONO | 1.84397089 | 0.062994624 | 1.693174138 | 0.199637423 | 8.18% |
| NTHL1 | 1.001350369 | 0.131660656 | 1.147143805 | 0.028701554 | 14.56% |
| NTHL1 | 0.574183719 | 0.115223842 | 0.645347702 | 0.083707156 | 12.39% |
| NUDT1 | 0.733691246 | 0.02877895 | 0.802191846 | 0.043445081 | 9.34% |
| NUDT1 | 0.764389177 | 0.059789195 | 0.806341786 | 0.004894415 | 5.49% |
| NUP205 | 0.662804988 | 0.079274607 | 0.800806452 | 0.040496562 | 20.82% |
| NUP205 | 0.730562082 | 0.081662056 | 0.909885536 | 0.09129767 | 24.55% |
| OGG1 | 1.345697704 | 0.198202209 | 1.414246971 | 0.036288628 | 5.09% |
| OGG1 | 0.769677206 | 0.070479563 | 0.904829439 | 0.120057041 | 17.56% |
| OGT | 0.80438673 | 0.049329366 | 0.922861934 | 0.006202001 | 14.73% |
| OGT | 0.787301772 | 0.148415465 | 1.006394466 | 0.153674726 | 27.83% |
| PAFAH1B3 | 1.340924127 | 0.194142412 | 1.888533453 | 0.766722412 | −40.84% |
| PAFAH1B3 | 1.699745813 | 0.053856671 | 1.745167831 | 0.189695117 | 2.67% |
| PAICS | 0.763027884 | 0.056611495 | 0.800057591 | 0.007461821 | 4.85% |
| PAICS | 0.979213509 | 0.037642874 | 1.002134255 | 0.028226997 | 2.34% |
| PARP1 | 1.494063164 | 0.097813841 | 1.335751295 | 0.318840968 | 10.60% |
| PARP1 | 1.343744559 | 0.052759186 | 1.841450777 | 0.909471525 | −37.04% |
| PARP2 | 1.069814409 | 0.577670361 | 1.261365172 | 0.855459643 | 17.91% |
| PARP2 | 1.041099685 | 0.038000202 | 1.139920347 | 0.203874733 | 9.49% |
| PCNA | 0.239193013 | 0.024341727 | 0.40204751 | 0.062477143 | −68.08% |
| PCNA | 0.285742404 | 0.044824887 | 0.364907398 | 0.101843788 | 27.71% |
| PIK3CB | 1.113006852 | 0.11716295 | 1.551939489 | 0.212096704 | −39.44% |
| PIK3CB | 1.118131175 | 0.090924768 | 1.541290339 | 0.154474956 | −37.85% |
| PLK1 | 0.202583655 | 0.019092656 | 0.228835323 | 0.036005583 | 12.96% |
| PLK1 | 0.258539643 | 0.034356536 | 0.296868664 | 0.058995452 | 14.83% |
| PMS1 | 0.846372688 | 0.08377974 | 1.010688212 | 0.030975732 | 19.41% |
| PMS1 | 0.920999098 | 0.045914146 | 1.013652455 | 0.055106511 | 10.06% |
| PMS2 | 0.846212077 | 0.085815047 | 1.029160757 | 0.194627073 | 21.62% |
| PMS2 | 1.02962014 | 0.026774353 | 1.363986962 | 0.148601365 | −32.47% |
| PMS2L3 | 1.042924273 | 0.02122765 | 1.436602497 | 0.037274537 | −37.75% |
| PMS2L3 | 0.730327128 | 0.046156347 | 0.849869927 | 0.113296622 | 16.37% |
| PNKP | 0.757307392 | 0.027266692 | 0.840811694 | 0.040156354 | 11.03% |
| PNKP | 0.900686765 | 0.020236289 | 1.062638684 | 0.031067462 | 17.98% |
| POLB | 1.692921063 | 0.031845939 | 1.971705339 | 0.359410185 | 16.47% |
| POLB | 0.718136491 | 0.102179626 | 0.606477685 | 0.091200501 | 15.55% |
| POLD1 | 1.171269172 | 0.091136261 | 1.289896889 | 0.133305242 | 10.13% |
| POLD1 | 0.65189128 | 0.083766021 | 0.635923235 | 0.019171176 | 2.45% |
| POLE | 0.36006371 | 0.015961676 | 0.404298934 | 0.015887855 | 12.29% |
| POLE | 0.470378449 | 0.078029927 | 0.493576979 | 0.046345196 | 4.93% |
| POLG | 0.944969905 | 0.221379113 | 1.073833009 | 0.220369446 | 13.64% |
| POLG | 0.779944631 | 0.066445735 | 0.809255213 | 0.060983479 | 3.76% |
| POLH | 1.177088124 | 0.071660795 | 1.268782572 | 0.107372389 | 7.79% |
| POLH | 0.909068661 | 0.063508841 | 0.921845622 | 0.03107983 | 1.41% |
| POLH | 1.00422917 | 0.019700222 | 1.425858481 | 0.056130679 | −41.99% |
| POLI | 1.365580022 | 0.056515253 | 1.609846602 | 0.113150911 | 17.89% |
| POLI | 1.350941075 | 0.067718606 | 1.484974986 | 0.095899691 | 9.92% |
| POLK | 1.084093984 | 0.037743481 | 1.247390915 | 0.114134048 | 15.06% |
| POLK | 1.392372986 | 0.057872984 | 1.782824769 | 0.097741764 | 28.04% |
| POLL | 0.713837777 | 0.065188911 | 0.804749564 | 0.081876458 | 12.74% |
| POLL | 0.685357684 | 0.034839121 | 0.795568881 | 0.008595048 | 16.08% |
| POLM | 1.03348222 | 0.062915947 | 1.069833275 | 0.064646037 | 3.52% |
| POLM | 1.072140854 | 0.030338963 | 1.096462458 | 0.039015514 | 2.27% |
| POLN | 0.776518454 | 0.040834685 | 0.894710097 | 0.023406799 | 15.22% |
| POLN | 0.831107848 | 0.033379191 | 0.814895743 | 0.051254906 | 1.95% |
| POLN | 0.977173324 | 0.136833629 | 1.430306972 | 0.053064726 | −46.37% |
| POLN | 1.070522321 | 0.10944335 | 1.474115505 | 0.026108428 | −37.70% |
| POLQ | 1.817925415 | 0.038128927 | 1.969002027 | 0.204668642 | 8.31% |
| POLQ | 1.079758319 | 0.030115834 | 1.120026551 | 0.068909376 | 3.73% |
| PPP2R5C | 0.780877652 | 0.033221846 | 0.838660501 | 0.081104022 | 7.40% |
| PPP2R5C | 0.743679163 | 0.014577188 | 0.781763979 | 0.053803136 | 5.12% |
| PRDX2 | 0.53556403 | 0.053850774 | 0.469370175 | 0.070958632 | 12.36% |
| PRDX2 | 1.306975028 | 0.070782665 | 1.613391644 | 0.183006563 | 23.44% |

TABLE 1-continued

|  | 0 Gy Avg | 0 Gy St dev | 6 Gy Avg | 6 Gy St dev | Relative Sensitization |
|---|---|---|---|---|---|
| PRDX4 | 0.955348037 | 0.052991499 | 0.908832674 | 0.134937811 | 4.87% |
| PRDX4 | 0.681417345 | 0.049799999 | 0.858149366 | 0.395648804 | 25.94% |
| PRKDC | 1.831923117 | 0.152474241 | 1.346834873 | 0.258136718 | 26.48% |
| PRKDC | 1.154253282 | 0.586521468 | 0.782879027 | 0.072359299 | 32.17% |
| PRMT1 | 0.666284281 | 0.021117386 | 0.722716263 | 0.055869548 | 8.47% |
| PRMT1 | 0.391012405 | 0.05150105 | 0.486118875 | 0.027183459 | 24.32% |
| PSMA1 | 0.479104796 | 0.02879132 | 0.547809211 | 0.02634527 | 14.34% |
| PSMA1 | 0.349269202 | 0.002616508 | 0.423552537 | 0.016236708 | 21.27% |
| PSMC4 | 0.251666872 | 0.034694173 | 0.331279197 | 0.020436708 | −31.63% |
| PSMC4 | 1.407651618 | 0.106571263 | 1.728920253 | 0.060840825 | 22.82% |
| PSME2 | 0.944288633 | 0.070159459 | 1.05595252 | 0.054089041 | 11.83% |
| PSME2 | 0.785637616 | 0.051126589 | 0.85705361 | 0.04163169 | 9.09% |
| PTMA | 1.092683317 | 0.168241686 | 1.213737726 | 0.157280281 | 11.08% |
| PTMA | 1.177508049 | 0.097012191 | 1.190297256 | 0.255281267 | 1.09% |
| RAD1 | 0.825203812 | 0.092998017 | 0.867506818 | 0.068775224 | 5.13% |
| RAD1 | 0.718548769 | 0.06679937 | 0.792198113 | 0.093348839 | 10.25% |
| RAD17 | 0.792180976 | 0.057811504 | 0.84131985 | 0.103258346 | 6.20% |
| RAD17 | 1.072846911 | 0.048075596 | 1.352243039 | 0.202140925 | 26.04% |
| RAD18 | 2.044047495 | 0.111956878 | 2.491777427 | 0.415969557 | 21.90% |
| RAD18 | 0.957394135 | 0.12954875 | 1.024520714 | 0.087694526 | 7.01% |
| RAD23A | 0.723549761 | 0.083643221 | 0.651144065 | 0.138278479 | 10.01% |
| RAD23A | 1.100861845 | 0.075767502 | 1.223847547 | 0.065045321 | 11.17% |
| RAD23B | 1.588948083 | 0.088358794 | 1.44217166 | 0.314714968 | 9.24% |
| RAD23B | 1.044117135 | 0.140404355 | 0.772065781 | 0.2128863 | 26.06% |
| RAD50 | 0.974337547 | 0.024550727 | 0.921468799 | 0.122931539 | 5.43% |
| RAD50 | 1.272432033 | 0.033422429 | 1.686015307 | 0.05132537 | −32.50% |
| RAD51 | 0.511182187 | 0.131272877 | 0.559586522 | 0.035667246 | 9.47% |
| RAD51 | 0.925017955 | 0.147411912 | 0.798785798 | 0.137513654 | 13.65% |
| RAD51C | 0.768457762 | 0.093630788 | 0.724393177 | 0.052532638 | 5.73% |
| RAD51C | 0.717585157 | 0.073467415 | 0.673763911 | 0.026263698 | 6.11% |
| RAD51L1 | 0.817873018 | 0.094902225 | 1.194446518 | 0.211469443 | −46.04% |
| RAD51L1 | 1.201168501 | 0.170081516 | 1.232813316 | 0.056555848 | 2.63% |
| RAD51L3 | 0.70513791 | 0.149672924 | 0.646015277 | 0.136603096 | 8.38% |
| RAD51L3 | 0.979560939 | 0.032141582 | 1.16006071 | 0.155376595 | 18.43% |
| RAD52 | 1.030707118 | 0.042929649 | 1.185290239 | 0.242449811 | 15.00% |
| RAD52 | 0.937906403 | 0.037925306 | 1.214674927 | 0.165845884 | −29.51% |
| RAD54B | 1.352737114 | 0.064491212 | 1.583341616 | 0.166379203 | 17.05% |
| RAD54B | 1.113199656 | 0.057171838 | 1.272206209 | 0.152437673 | 14.28% |
| RAD54L | 0.972644924 | 0.053778984 | 0.819365228 | 0.367401917 | 15.76% |
| RAD54L | 0.776457272 | 0.164819999 | 0.686010468 | 0.009817277 | 11.65% |
| RAD9A | 0.850043592 | 0.014605471 | 0.923031319 | 0.039630503 | 8.59% |
| RAD9A | 0.660196699 | 0.019886843 | 0.618815319 | 0.033428832 | 6.27% |
| RBM4 | 0.994264213 | 0.084276284 | 1.069414096 | 0.065704696 | 7.56% |
| RBM4 | 1.012618731 | 0.035887922 | 1.050866406 | 0.061712412 | 3.78% |
| RECQL4 | 0.998043697 | 0.040026929 | 1.101089376 | 0.024145818 | 10.32% |
| RECQL4 | 0.945621689 | 0.029731666 | 0.995334036 | 0.029924898 | 5.26% |
| REV1 | 1.058741041 | 0.054179002 | 1.246378509 | 0.147637522 | 17.72% |
| REV1 | 0.973667809 | 0.0044165 | 0.918140643 | 0.023286175 | 5.70% |
| REV3L | 0.875296349 | 0.039583261 | 0.964191947 | 0.026776987 | 10.16% |
| REV3L | 0.848988207 | 0.044018351 | 0.812998628 | 0.026009492 | 4.24% |
| RFC4 | 0.751851396 | 0.069120099 | 1.080011927 | 0.161376804 | −43.65% |
| RFC4 | 0.539180711 | 0.045344645 | 0.609647815 | 0.102207721 | 13.07% |
| RPA1 | 0.474494591 | 0.027492229 | 0.56901295 | 0.108270301 | 19.92% |
| RPA1 | 0.396088704 | 0.047348825 | 0.535485025 | 0.104865168 | −35.19% |
| RPA2 | 0.542762303 | 0.016064604 | 0.619293655 | 0.099365573 | 14.10% |
| RPA2 | 0.969049084 | 0.064344594 | 0.940927012 | 0.462411173 | 2.90% |
| RPA3 | 0.781107083 | 0.063542864 | 0.791808527 | 0.050814142 | 1.37% |
| RPA3 | 0.817204301 | 0.045263551 | 0.819672409 | 0.029970272 | 0.30% |
| RPA4 | 1.090301582 | 0.080537699 | 1.252547733 | 0.031526223 | 14.88% |
| RPA4 | 1.060783906 | 0.089242319 | 1.165631955 | 0.063527532 | 9.88% |
| RPL13 | 0.982410581 | 0.015371703 | 1.045761587 | 0.03335435 | 6.45% |
| RPL13 | 1.134950313 | 0.01694113 | 1.14710476 | 0.133957623 | 1.07% |
| RPL27 | 0.317302885 | 0.021821095 | 0.424388826 | 0.050024839 | −33.75% |
| RPL27 | 0.404767142 | 0.047657271 | 0.588718155 | 0.072362476 | −45.45% |
| RPL35 | 0.260419931 | 0.010107865 | 0.425816625 | 0.17020649 | −63.51% |
| RPL35 | 0.346634632 | 0.053329427 | 0.43852219 | 0.033930958 | 26.51% |
| RRM2B | 1.835265852 | 0.088012263 | 2.067402568 | 0.263075495 | 12.65% |
| RRM2B | 1.732616038 | 0.311187984 | 1.787474656 | 0.143368398 | 3.17% |
| SDHC | 0.746738249 | 0.063002438 | 0.71617799 | 0.058123403 | 4.09% |
| SDHC | 0.839902721 | 0.064063922 | 0.795450311 | 0.065602835 | 5.29% |
| SDHC | 1.072763419 | 0.061501225 | 1.397684703 | 0.047562692 | −30.29% |
| SETD7 | 1.268470907 | 0.138721625 | 1.657721234 | 0.068811337 | −30.69% |
| SETD7 | 0.91142822 | 0.188260736 | 1.046449988 | 0.189063493 | 14.81% |
| SETD8 | 0.328771893 | 0.060194006 | 0.308267628 | 0.052808991 | 6.24% |
| SETD8 | 1.725512727 | 0.107258939 | 1.267312458 | 0.291727995 | 26.55% |
| SMARCA4 | 1.083999862 | 0.03674433 | 1.058021944 | 0.028473389 | 2.40% |
| SMARCA4 | 1.052491257 | 0.101614772 | 1.248526024 | 0.102740888 | 18.63% |
| SMUG1 | 0.469722694 | 0.070949326 | 0.543709877 | 0.025514302 | 15.75% |

TABLE 1-continued

| | 0 Gy Avg | 0 Gy St dev | 6 Gy Avg | 6 Gy St dev | Relative Sensitization |
|---|---|---|---|---|---|
| SMUG1 | 0.814282874 | 0.046241008 | 0.907566441 | 0.012424282 | 11.46% |
| SND1 | 1.120638285 | 0.08028654 | 1.164821401 | 0.01387382 | 3.94% |
| SND1 | 0.764382411 | 0.048384332 | 0.866380371 | 0.060316309 | 13.34% |
| SNRPE | 0.250774748 | 0.04218319 | 0.254021176 | 0.034499364 | 1.29% |
| SNRPE | 1.093036945 | 0.058778876 | 1.176291437 | 0.094178192 | 7.62% |
| SNRPF | 0.360808144 | 0.044821314 | 0.393053766 | 0.030910898 | 8.94% |
| SNRPF | 0.458969565 | 0.216341599 | 0.373257585 | 0.02361055 | 18.67% |
| SOX4 | 1.368212572 | 0.065414864 | 1.668455753 | 0.146408279 | 21.94% |
| SOX4 | 1.126756059 | 0.144170173 | 1.208726767 | 0.143286316 | 7.27% |
| SPO11 | 0.962674423 | 0.053744433 | 1.072683613 | 0.024790567 | 11.43% |
| SPO11 | 0.938592847 | 0.039822107 | 1.099918004 | 0.082286484 | 17.19% |
| SSBP1 | 1.114802047 | 0.190161168 | 1.027618833 | 0.079890785 | 7.82% |
| SSBP1 | 2.017305616 | 0.105782625 | 1.961883307 | 0.321744314 | 2.75% |
| SSR1 | 0.923155753 | 0.048337445 | 0.964801735 | 0.032101674 | 4.51% |
| SSR1 | 0.902292785 | 0.018146642 | 0.923065196 | 0.043842017 | 2.30% |
| SSR1 | 1.178185433 | 0.371732748 | 1.469901145 | 0.040405264 | 24.76% |
| SUV39H1 | 1.130696475 | 0.046219036 | 1.220559619 | 0.112912001 | 7.95% |
| SUV39H1 | 1.034445311 | 0.014717011 | 0.986652438 | 0.081736941 | 4.62% |
| SUV39H2 | 1.156991741 | 0.084704866 | 1.140530989 | 0.310941747 | 1.42% |
| SUV39H2 | 1.066428043 | 0.076814973 | 1.08658212 | 0.224213368 | 1.89% |
| TARS | 1.092703313 | 0.135950105 | 1.185712049 | 0.181531826 | 8.51% |
| TARS | 1.315167917 | 0.160206793 | 1.513997946 | 0.436690366 | 15.12% |
| TDG | 1.043664473 | 0.059542555 | 0.94854697 | 0.131023792 | 9.11% |
| TDG | 1.965110206 | 0.130389798 | 2.049921153 | 0.455489286 | 4.32% |
| TDP1 | 1.364669701 | 0.084413264 | 1.605672067 | 0.071219197 | 17.66% |
| TDP1 | 1.120892628 | 0.016110377 | 1.1483347 | 0.159712848 | 2.45% |
| TGIF1 | 1.080145189 | 0.098050022 | 1.461869573 | 0.227788929 | −35.34% |
| TGIF1 | 0.948912052 | 0.041567691 | 1.074693339 | 0.210315008 | 13.26% |
| TMEM30A | 0.9571411 | 0.045285335 | 1.170162012 | 0.181927153 | 22.26% |
| TMEM30A | 1.328010825 | 0.160492727 | 1.59742239 | 0.102380157 | 20.29% |
| TOP2A | 0.709872223 | 0.068846446 | 0.758393165 | 0.084125223 | 6.84% |
| TOP2A | 0.690695675 | 0.081985123 | 0.734594824 | 0.030496926 | 6.36% |
| TP53BP1 | 1.65385285 | 0.098191519 | 1.349628295 | 0.498273727 | 18.39% |
| TP53BP1 | 1.145060761 | 0.03948085 | 1.156386574 | 0.164304495 | 0.99% |
| TPX2 | 0.345317843 | 0.044176878 | 0.49504574 | 0.10285601 | −43.36% |
| TPX2 | 0.847127517 | 0.017319157 | 0.964526158 | 0.058915548 | 13.86% |
| TRAF4 | 0.75428712 | 0.120454756 | 0.769903588 | 0.070453027 | 2.07% |
| TRAF4 | 0.58248247 | 0.180237487 | 0.938872875 | 0.305702298 | −61.18% |
| TRDMT1 | 1.013820144 | 0.055052864 | 1.27108059 | 0.056221051 | 25.38% |
| TRDMT1 | 1.003455036 | 0.064872547 | 1.369734518 | 0.192587955 | 36.50% |
| TREX1 | 0.803082358 | 0.163382387 | 0.895175537 | 0.096258278 | 11.47% |
| TREX1 | 1.003493857 | 0.032700862 | 1.246846309 | 0.153152632 | 24.25% |
| TREX2 | 1.114725058 | 0.078651636 | 0.794619488 | 0.317513264 | 28.72% |
| TREX2 | 0.604256366 | 0.064314841 | 0.970910778 | 0.077896404 | −60.68% |
| TSTA3 | 0.904537183 | 0.129294758 | 0.790154108 | 0.331863616 | 12.65% |
| TSTA3 | 0.73016857 | 0.172535519 | 0.864076584 | 0.205934855 | 18.34% |
| TUBB | 0.811779371 | 0.068025776 | 0.805962282 | 0.048349847 | 0.72% |
| TUBB | 0.957394135 | 0.077029388 | 0.939713404 | 0.141855363 | 1.85% |
| UBE2A | 0.791691522 | 0.033880413 | 0.786828599 | 0.056549419 | 0.61% |
| UBE2A | 1.36456453 | 0.181344495 | 1.344878207 | 0.055772107 | 1.44% |
| UBE2A | 1.020187963 | 0.067432635 | 1.40991155 | 0.07672793 | −38.20% |
| UBE2B | 1.077871265 | 0.026494129 | 1.126469095 | 0.066458707 | 4.51% |
| UBE2B | 1.014317371 | 0.020335035 | 1.135801023 | 0.048036463 | 11.98% |
| UBE2N | 0.923202105 | 0.100131378 | 1.107473351 | 0.028225986 | 19.96% |
| UBE2N | 1.045687476 | 0.024308099 | 1.22086213 | 0.084046203 | 16.75% |
| UBE2S | 1.144693955 | 0.040318695 | 1.221230625 | 0.187321024 | 6.69% |
| UBE2S | 0.978823812 | 0.06026047 | 1.158156076 | 0.15539387 | 18.32% |
| UBE2V2 | 1.610606219 | 0.109388676 | 1.593872494 | 0.224505875 | 1.04% |
| UBE2V2 | 0.947681867 | 0.057566223 | 1.10214361 | 0.036703067 | 16.30% |
| UNG | 0.726633042 | 0.040307347 | 0.806248551 | 0.061815077 | 10.96% |
| UNG | 1.121411518 | 0.055191263 | 1.315767212 | 0.047598982 | 17.33% |
| WRN | 1.088721752 | 0.182807012 | 0.989637306 | 0.345886214 | 9.10% |
| WRN | 0.989820297 | 0.061506019 | 1.149818437 | 0.06864358 | 16.16% |
| XAB2 | 0.205523006 | 0.031549473 | 0.244671095 | 0.014958665 | 19.05% |
| XAB2 | 0.27561039 | 0.052777351 | 0.370596524 | 0.117461503 | −34.46% |
| XPA | 1.022956269 | 0.050251198 | 1.032232244 | 0.084341859 | 0.91% |
| XPA | 1.006665282 | 0.022237175 | 1.125727227 | 0.043821683 | 11.83% |
| XPC | 1.013901873 | 0.058506357 | 0.981179962 | 0.042709163 | 3.23% |
| XPC | 1.019112912 | 0.036188718 | 1.140291281 | 0.01786393 | 11.89% |
| XRCC1 | 0.393049897 | 0.030277741 | 0.365307502 | 0.062157112 | 7.06% |
| XRCC1 | 0.996953014 | 0.123844963 | 0.975635469 | 0.003643983 | 2.14% |
| XRCC2 | 0.598558446 | 0.087284639 | 0.596891192 | 0.057007034 | 0.28% |
| XRCC2 | 1.121637062 | 0.026148695 | 1.111026512 | 0.093941714 | 0.95% |
| XRCC3 | 1.478139993 | 0.029208955 | 1.932478548 | 0.027419033 | −30.74% |
| XRCC3 | 0.503628983 | 0.004624957 | 0.469668356 | 0.013361831 | 6.74% |
| XRCC4 | 1.015334149 | 0.01682787 | 1.197805479 | 0.181934329 | 17.97% |
| XRCC4 | 1.054678856 | 0.02970874 | 1.198054291 | 0.211292253 | 13.59% |
| XRCC5 | 1.064328421 | 0.080256697 | 0.931825807 | 0.618120205 | 12.45% |

TABLE 1-continued

|  | 0 Gy Avg | 0 Gy St dev | 6 Gy Avg | 6 Gy St dev | Relative Sensitization |
|---|---|---|---|---|---|
| XRCC5 | 0.248575256 | 0.049170377 | 0.625690577 | 0.629193334 | −151.71% |
| XRCC6 | 0.972196254 | 0.069516122 | 1.048572879 | 0.021400333 | 7.86% |
| XRCC6 | 0.8919705 | 0.151343437 | 0.818378822 | 0.105603542 | 8.25% |
| ZDHHC17 | 1.244753352 | 0.097540066 | 1.332637577 | 0.169147293 | 7.06% |
| ZDHHC17 | 1.258531185 | 0.057937462 | 1.293708379 | 0.021835192 | 2.80% |

Example 2

Figure 5A:
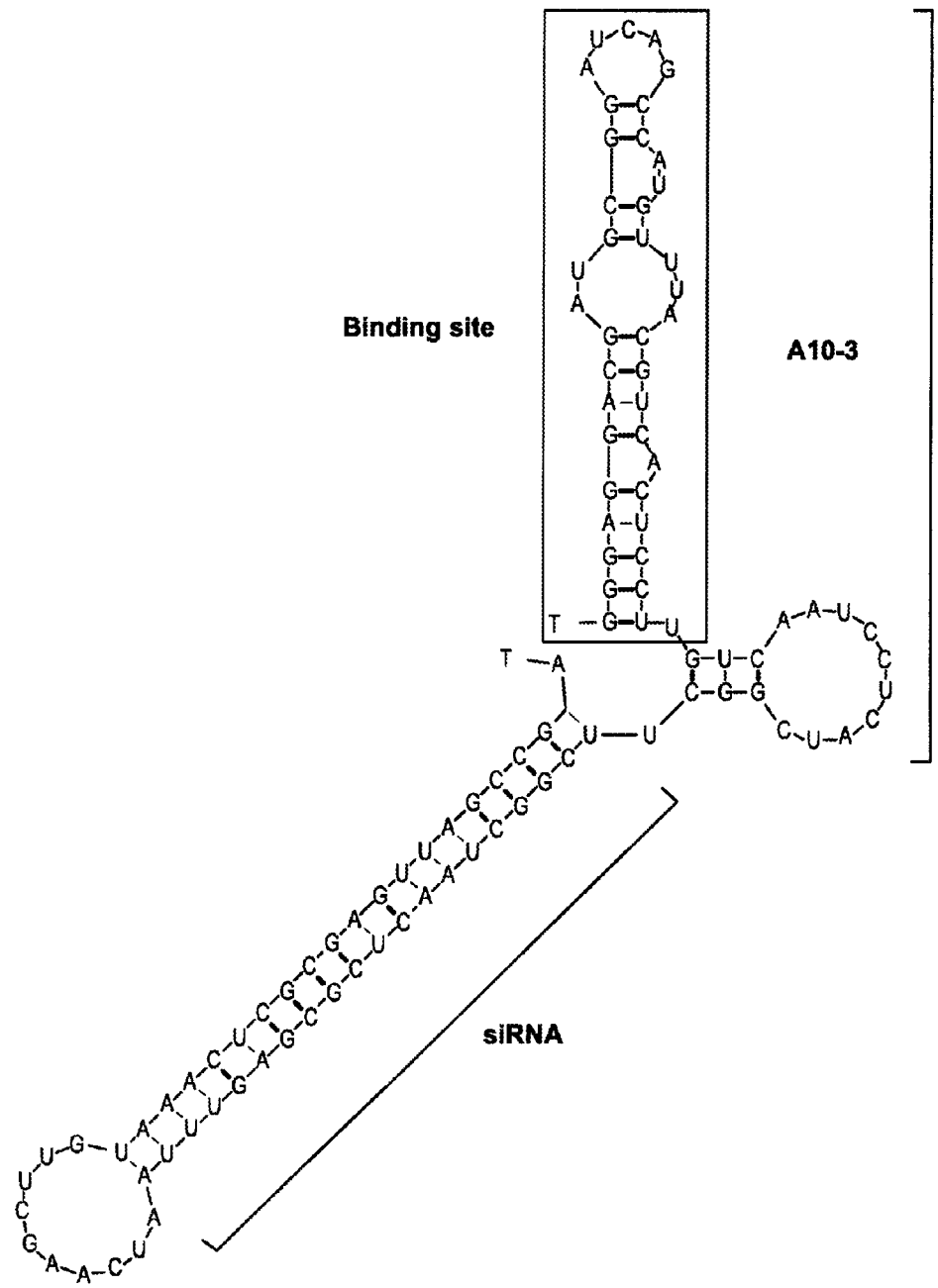
FIGS. 5A -5F demonstrate the ability of aptamer-shRNA chimeras to mediate target gene knock-down in PSMA expressing cells.
Figure 5B:
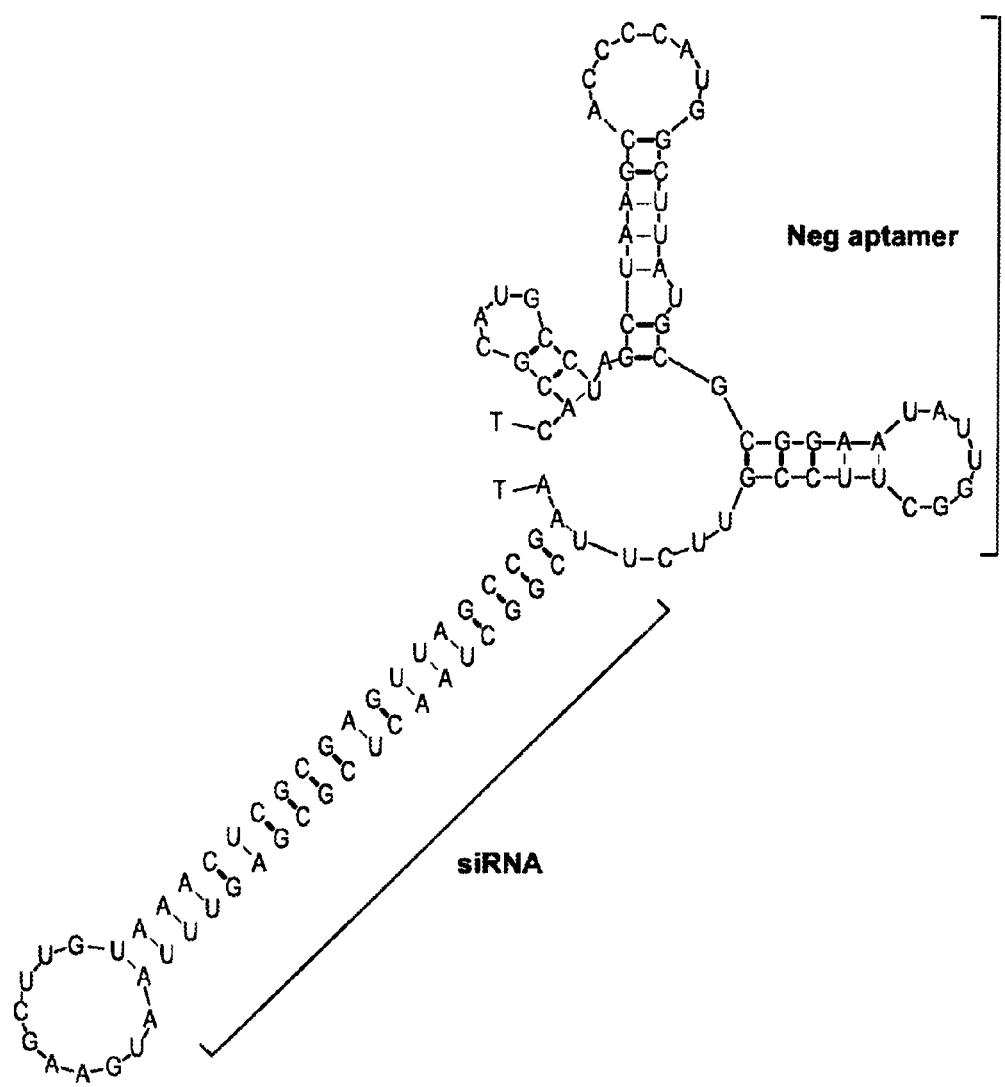
Figure 5C:
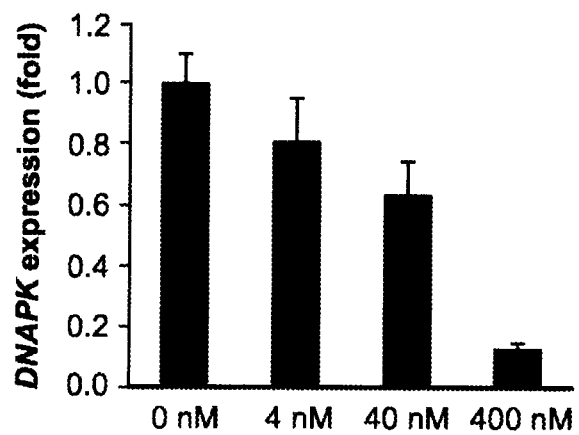
Figure 5D:
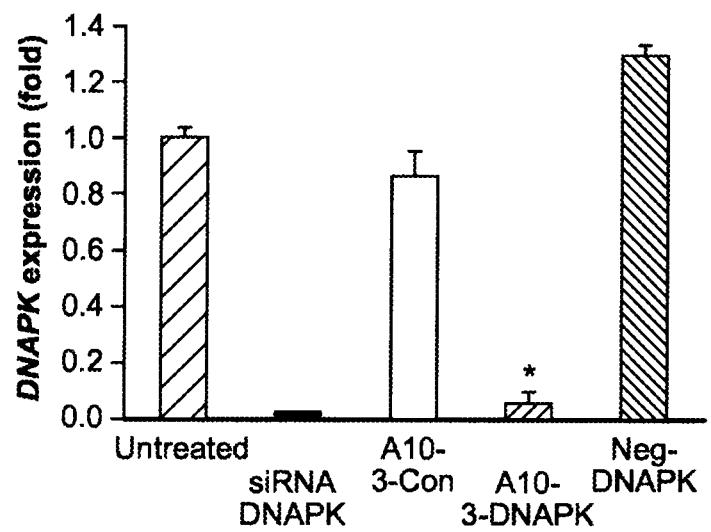
Figure 5E:
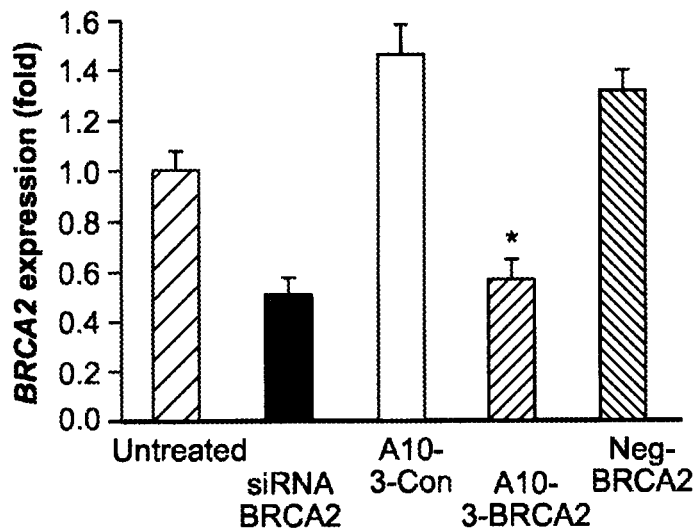
Figure 5F:
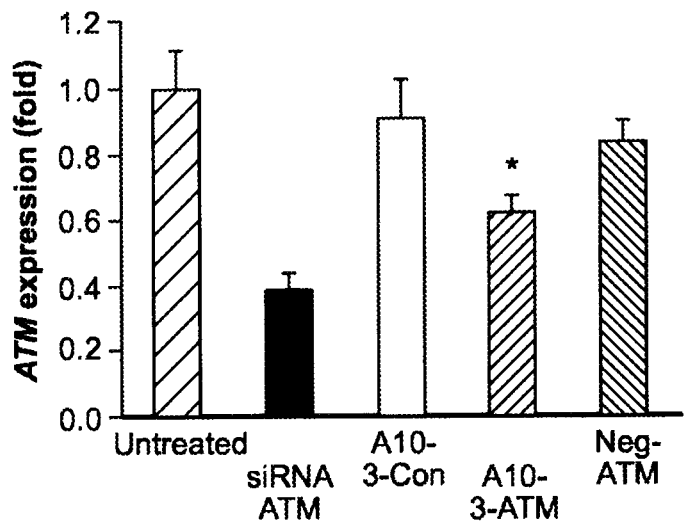

Generation of Aptamer-shRNAs Chimeras that Selectively Target PSMA-expressing Cells Candidate and previously identified radiosensitizing siRNAs (Collis S J, Swartz M J, Nelson W G, DeWeese T L. Enhanced radiation and chemotherapy-mediated cell killing of human cancer cells by small inhibitory RNA silencing of DNA repair factors. Cancer Res. 2003; 63(7):1550-1554) were linked to the PSMA-targeting A10-3 aptamer for selective cell delivery. Aptamer-shRNA chimeras were designed as a single intact nuclease-stabilized 2' fluoro-modified pyrimidine transcript. The 3'-terminus of the A10-3 aptamer was conjugated to the passenger (sense) strand of the siRNA, followed by a 10-mer loop sequence and then by the guide or silencing (antisense) strand of the siRNA. The secondary structures of each aptamer-shRNA chimera were evaluated by mFold to predict proper folding of the aptamer portion (FIG. 5A). Control chimeras were generated with nonspecific shRNAs (referred to herein as A10-3-Con) or nontargeting aptamer portions (denoted by the prefix Neg– followed by the target gene; FIG. 5B). LNCaP cells were treated with aptamer-shRNA chimeras, in the absence of transfection reagents, and changes in target gene mRNA were evaluated by qRT-PCR relative to untreated cells. The efficiency of chimera A10-3-DNAPK was first evaluated at 4, 40, and 400 nM in LNCaP cells, and 400 nM was determined to be the most effective dose (FIG. 5C). Within 48 hours of treatment at 400 nM, aptamer targeted shRNA caused significant reductions in DNAPK, BRCA2, and ATM mRNA levels (FIGS. 5D-5F). A10-3-Con and aptamer control chimeras (Neg-DNAPK, Neg-BRCA2, and Neg-ATM) had no detectable effect on target mRNA levels. Transfected siRNA served as a positive control for knockdown of each gene. Because delivered shRNAs could potentially induce nonspecific inflammatory responses that cause cellular toxicity (Sledz C A, Holko M, de Veer M J, Silverman R H, Williams B R. Activation of the interferon system by short-interfering RNAs. Nat Cell Biol. 2003; 5(9):834-839), whether INF-β was induced in LNCaP cells transfected with DNAPK siRNAs or treated with aptamer-shRNA chimeras was evaluated by ELISA. The applied treatment conditions failed to cause any detectable increases in INF-β (FIG. 6).

Figure 7A:
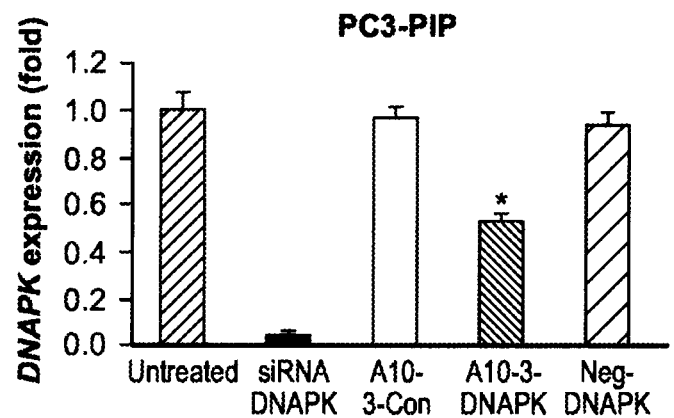
FIGS. 7A-7H show the PSMA selectivity of the aptamer-shRNA chimeras.
Figure 7B:
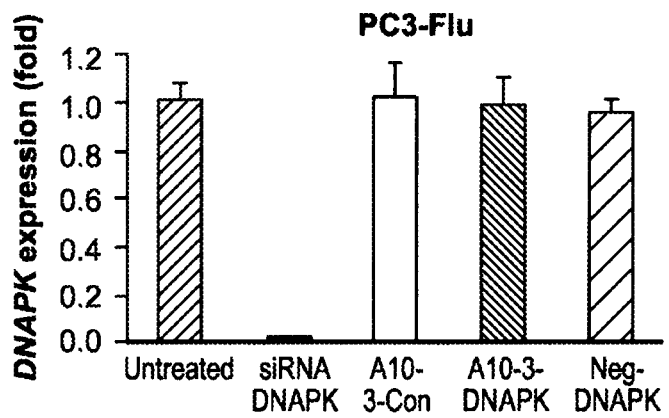

To further confirm PSMA-selective targeting, a second and previously described isogenic cell model of PSMA-expressing PC3 cells (PC3-PIP) and PSMA-negative control cells (PC3-Flu) (Chang S S, Reuter V E, Heston W D, Bander N H, Grauer L S, Gaudin P B. Five different anti-prostate-specific membrane antigen (PSMA) antibodies confirm PSMA expression in tumor-associated neovasculature. Cancer Res. 1999; 59(13):3192-3198) was subjected to aptamer-shRNA chimera treatment. A10-3-DNAPK treatment selectively reduced DNAPK levels in PC3-PIP cells, but not in PC3-Flu cells (FIGS. 7A and 7B).

Example 3

Aptamer-shRNA Chimeras Enter Cells and are Processed by the RNAi Machinery

Figure 7C:
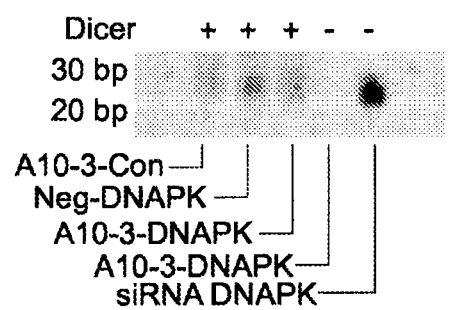
Figure 7D:
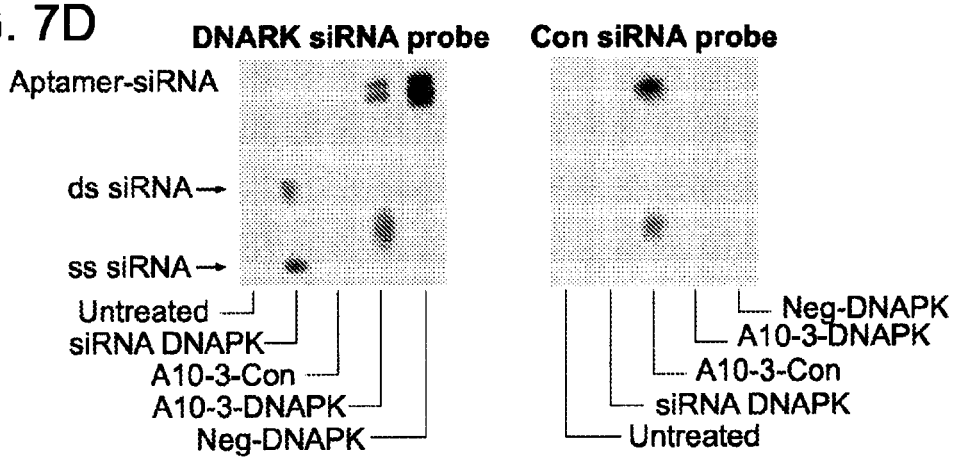

The processing of aptamer-shRNA chimeras by RNAi machinery was evaluated. Aptamer-shRNA himeras were incubated in the presence or absence of recombinant human Dicer for 1 hour at 37° C. shRNA cleavage products were obtained in samples treated with Dicer, whereas no cleavage products were detected in its absence (FIG. 7C). Aptamer-shRNA chimera processing was further interrogated in an intact cell model. LNCaP cells were treated with A10-3 aptamer-shRNA chimeras in the absence of transfection reagents and evaluated for the presence of the desired siRNA product by Northern blotting. A10-3-DNAPK and A10-3-Con were effectively internalized and processed to produce antisense siRNAs (FIG. 7D). Collectively, these results support that A10-3 aptamer-shRNA bound PSMA, were internalized into cells, and were processed by RNAi machinery, whereas Neg-DNAPK could not enter cells to be processed. In the absence of extensive cell washing, the unprocessed chimeras were detectable by Northern blot, and levels indicated that approximately half of the A10-3 aptamer-shRNA chimeras were internalized and processed to the mature siRNAs in the experimental time period. Processed siRNAs from aptamer-shRNA chimeras resulted in products that were slightly different compared with reference siRNA.

Example 4

Aptamer-shRNA Chimeras Target PSMA Expressing Cells In Vivo

Figure 7E:
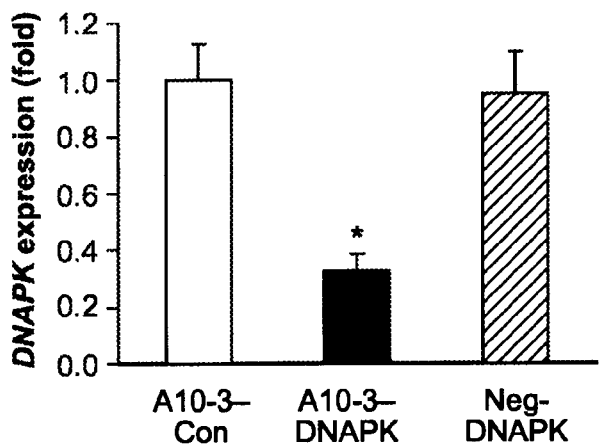
Figure 7F:
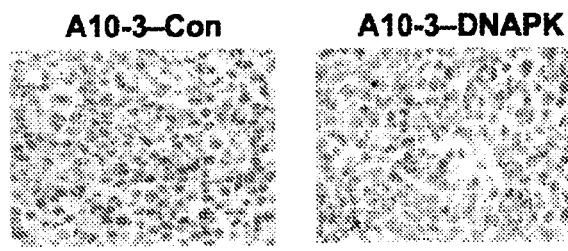
Figure 7G:
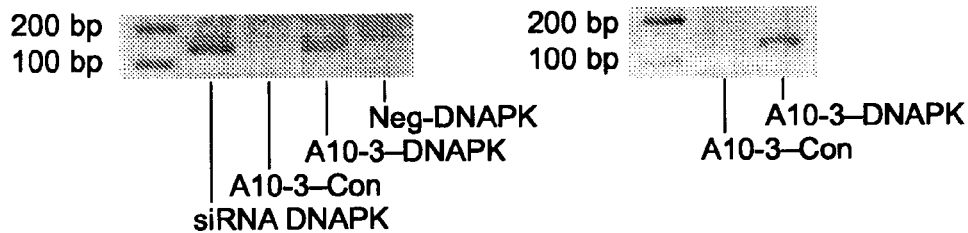
Figure 7H:
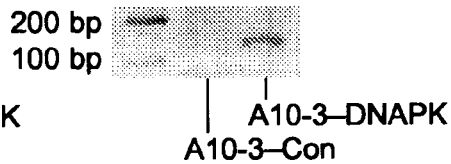

Aptamer-targeted DNAPK RNAi was evaluated in vivo. LNCaP xenografts were established subcutaneously in nude male mice and treated with 200 pmol of targeted and control aptamer-shRNA chimeras by 2 consecutive intratumoral injections. qRT-PCR and immunohistochemistry demonstrated reduction of DNAPK mRNA and DNAPK protein after treatment with A10-3-DNAPK, but not controls (FIGS. 7E and 7F). Quantification of total DNAPK protein staining per nuclear area by FrIDA image analysis (Gurel B, et. al. Nuclear MYC protein overexpression is an early alteration in human prostate carcinogenesis. Mod Pathol. 2008; 21(9): 1156-1167) indicated a 52% protein reduction in A10-3-DNAPK-treated tumors compared with A10-3-Con treatment. That aptamer-shRNA chimera-mediated DNAPK knockdown occurs through RNAi was confirmed by identifying DNAPK mRNA cleavage products with 5'-rapid amplification of cDNA ends (5'-RACE) in cell line and animal model treatments (FIGS. 7G and 7H).

Example 5

Aptamer-targeted Radiosensitization in Human PCa Cell and Tumor Models

Figure 8A:
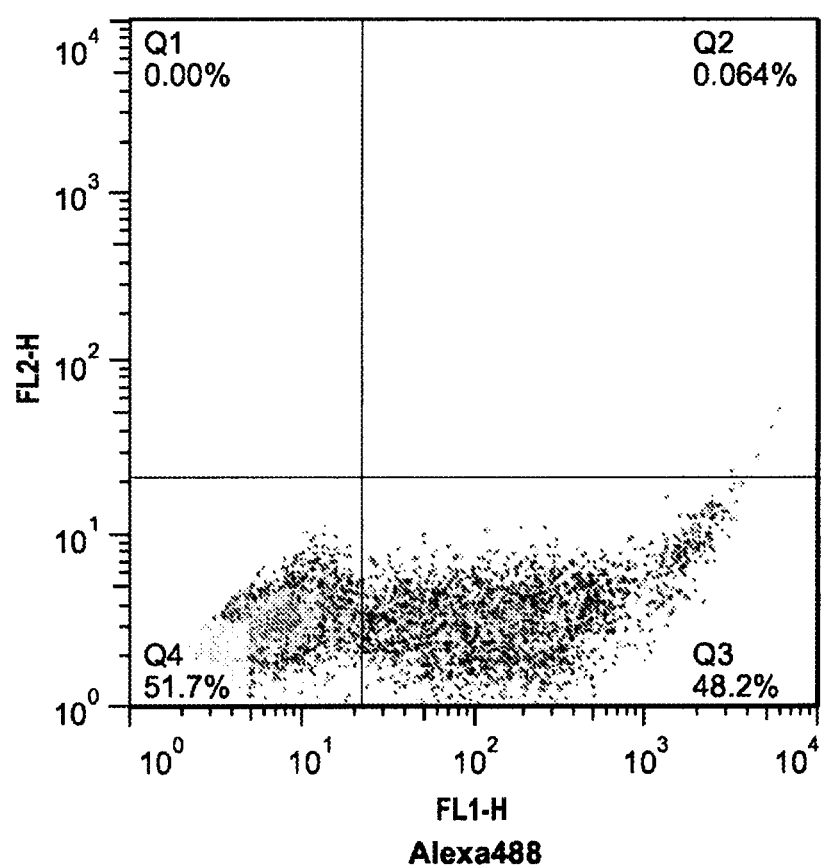
FIGS. 8A and 8B include flow cytometry results showing the cell surface expression of PSMA. PSMA positive PC3-PIP cells and PSMA negative PC3-Flu cells were incubated with anti-PSMA (J591) antibody and stained with secondary antibody conjugated with Alexa488. PSMA expression was then determined by flow cytometry. 48.2% of PC3-PIP (FIG. 8A) cells expressed PSMA when compared to PC3-Flu (FIG. 8B) cells.
Figure 8B:
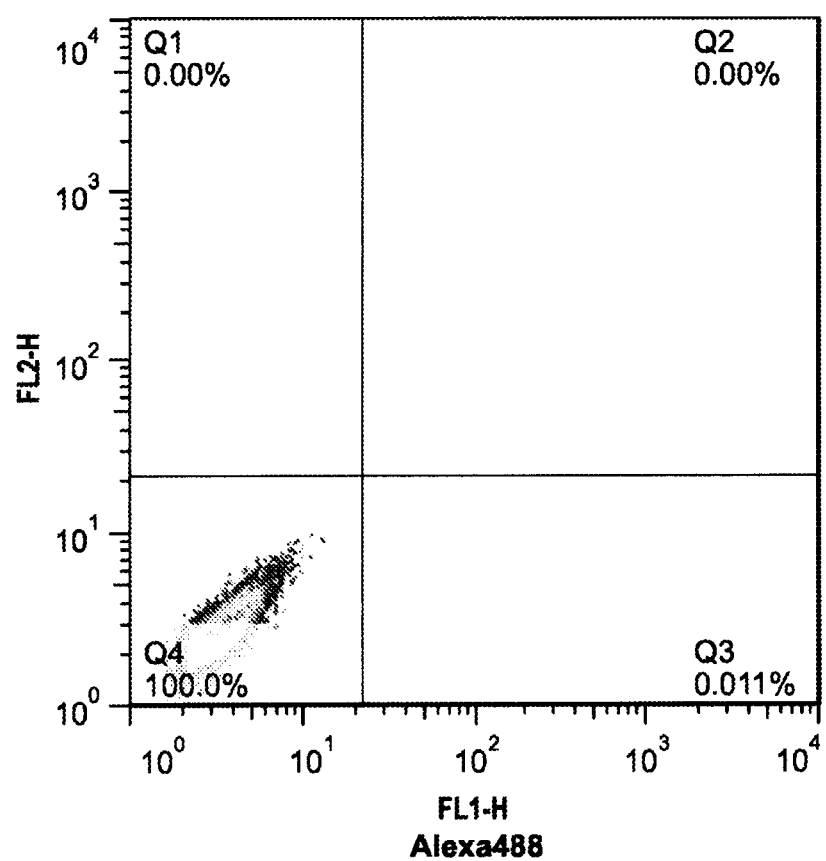
Figure 9A:
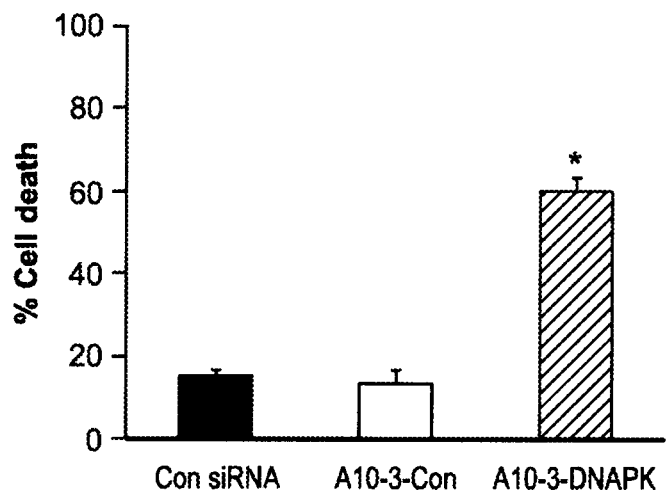
FIGS. 9A-9D are graphs showing aptamer-shRNA mediated radiosensitization in vitro and in vivo PCa models.

The aptamer-shRNA chimera targeting the catalytic subunit of DNAPK was used in targeted radiosensitization studies in LNCaP cells. LNCaP, rather than PC3-PIP, was selected for these studies due to the cells' consistent and high-level PSMA expression (FIG. 8). Treatment of LNCaP cells with A10-3-DNAPK in the absence of transfection reagents significantly increased cell death after IR compared with controls (FIG. 9A).

Figure 9B:
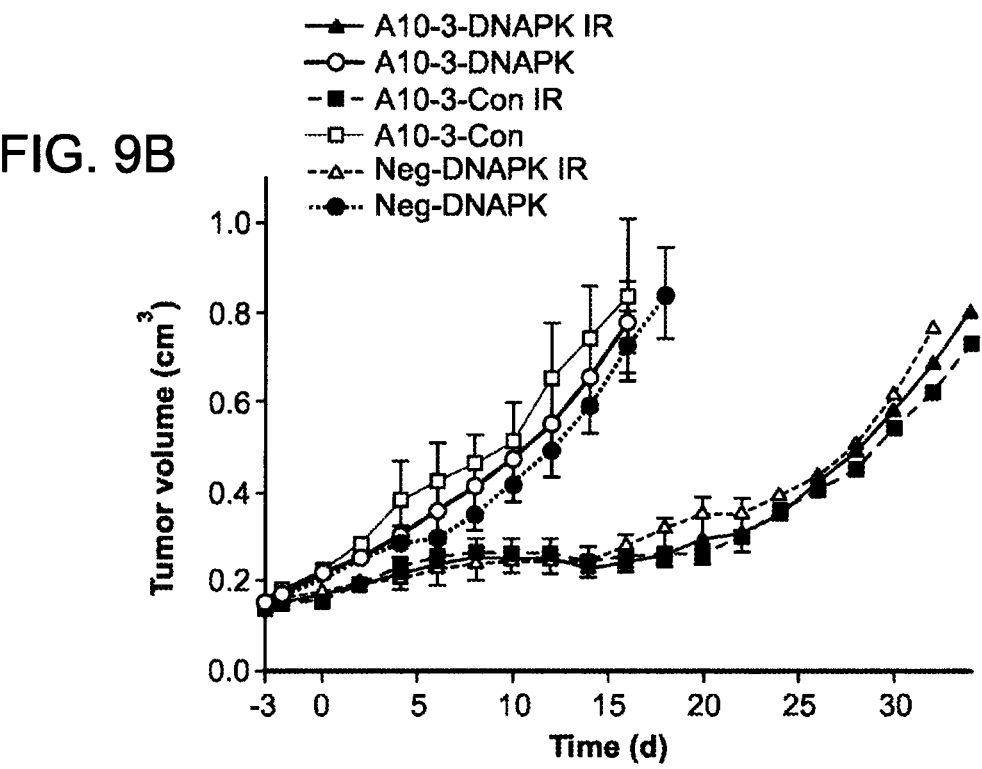
Figure 9C:
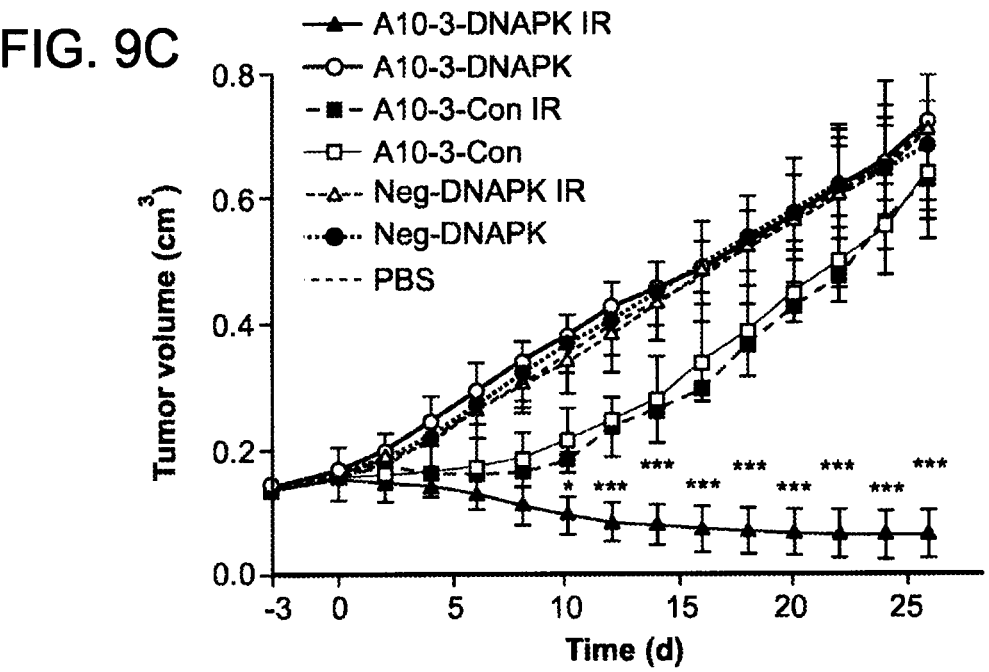
Figure 9D:
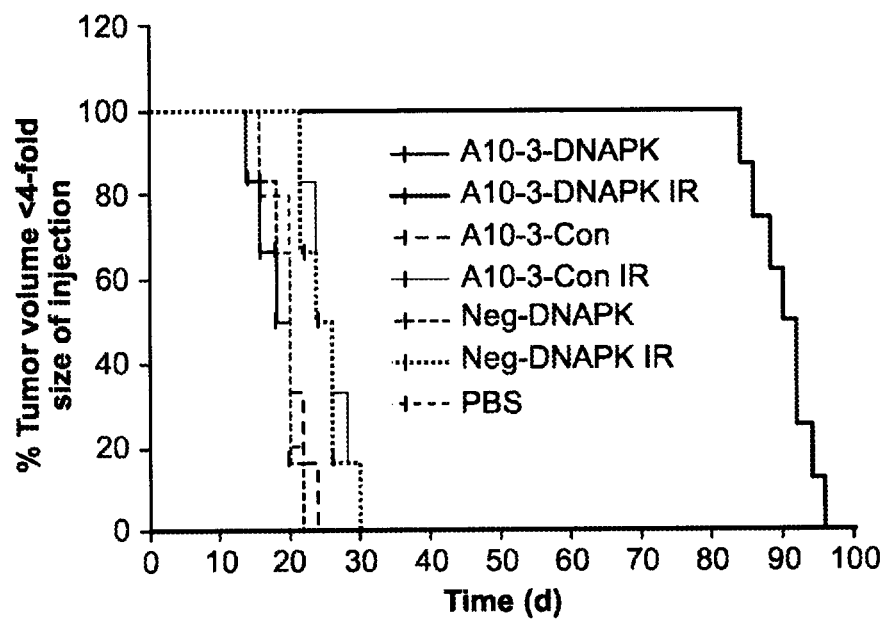
Figures 10A, 10B:
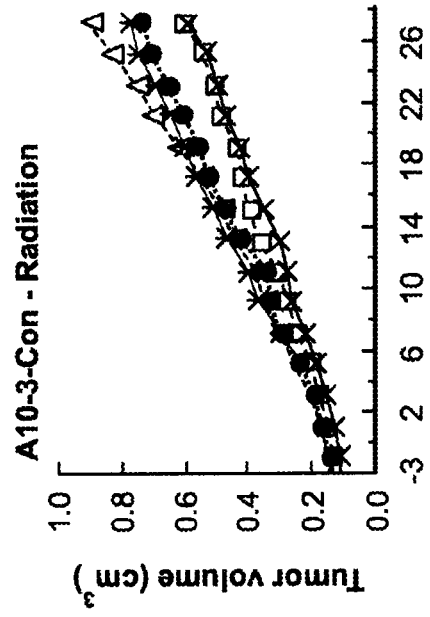
FIGS. 10A-10G are graphs showing aptamer-shRNA chimera mediated radiosensitization in individual LNCaP tumors in vivo. Established LNCaP tumors were intratumorally injected with 200 pmol aptamer-shRNAs on days −3 and day −2. On day 0, animals were divided into groups that received either 6 Gy radiation (+R) or no radiation (−R). Tumors were measured every other day until reaching four times the volume at time of radiation.
Figures 10C, 10D:
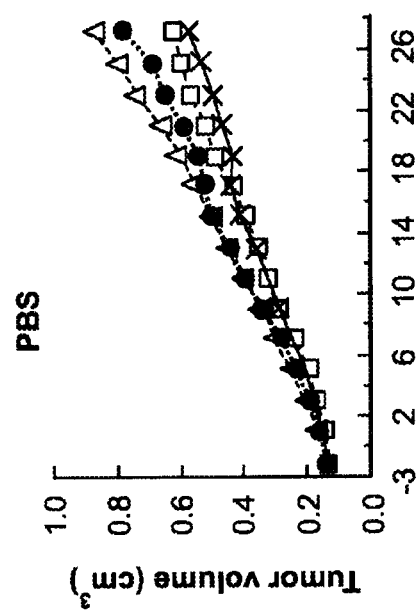
Figure 10E:
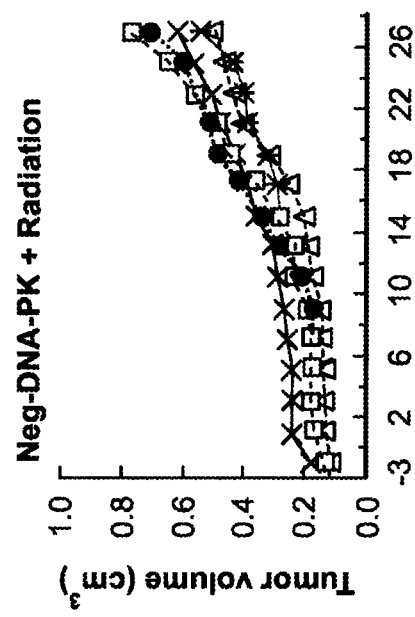
Figure 10F:
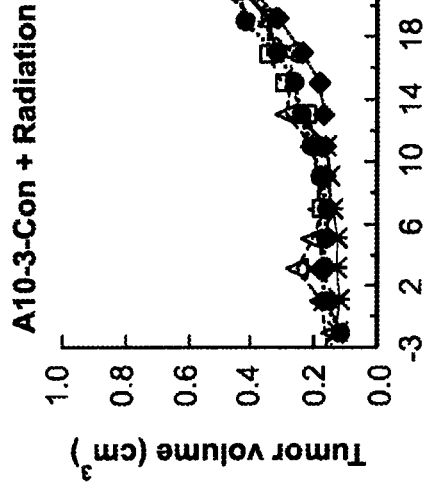
Figure 10G:
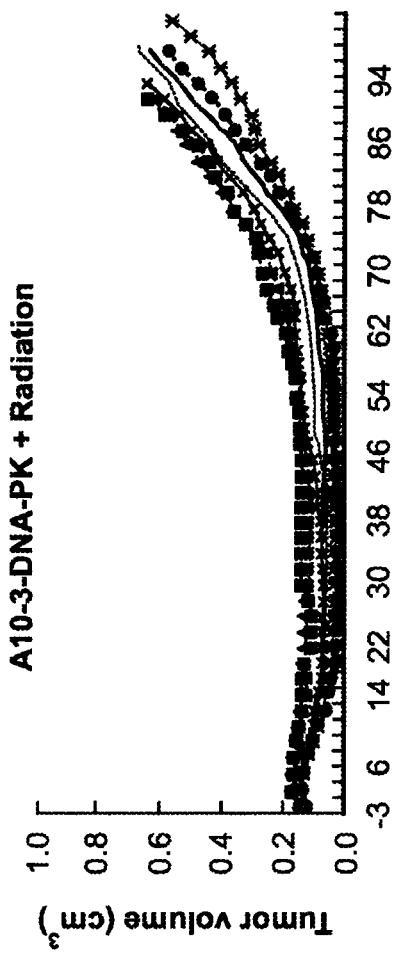

LNCaP tumors and PC3 tumors were then established subcutaneously in male nude mice and intratumorally injected twice with 200 pmol targeted or control aptamer-shRNA chimeras (days −3 and −2). Half of each cohort then received either no radiation treatment or a single radiation treatment (6 Gy) 2 days after aptamer-shRNA chimera injection (day 0). No differences in tumor volume were observed between nonirradiated cohorts (FIGS. 9B and 9C; see FIG. 10 for individual tumor curves), which suggests that chimera treatment alone had no detectable therapeutic effect in either tumor model. In both LNCaP and PC3 tumor models, irradiated tumors treated with control aptamer-shRNA chimeras resulted in a significant but temporary reduction in tumor volume compared with nonirradiated samples (FIG. 9D). Notably, the combination of A10-3-DNAPK and radiation resulted in a significant and extended tumor response in LNCaP tumors, but not PC3 tumors. This combination treatment dramatically extended the time to reach quadruple tumor volume, by approximately 10 weeks compared with 1 week in tumors treated with radiation and control aptamer-shRNA chimeras (FIG. 9D). Thus, in cell and tumor models, aptamer-targeted knockdown of DNAPK selectively enhanced radiosensitivity and increased therapeutic effect.

Example 6

Figures 11, 12A:
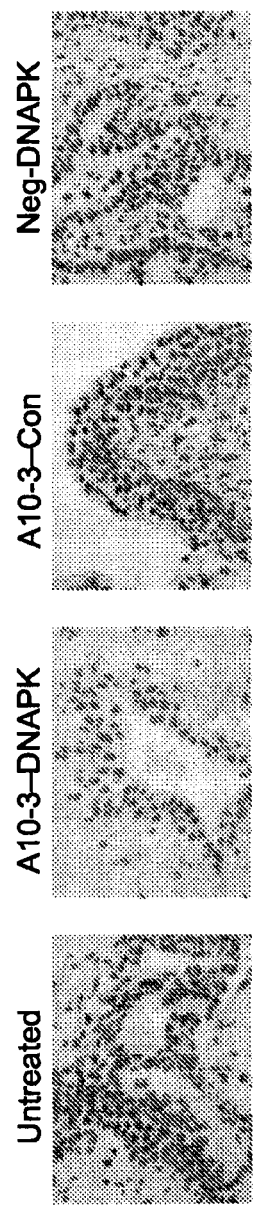
FIG. 11 shows the result of ex vivo treatment of human prostate tissue with aptamer-shRNA chimeras. Sections of normal human prostate tissue were obtained from fresh radical prostatectomy specimens and maintained ex vivo. These were treated with 200 nM aptamer-shRNA chimeras, and DNAPK levels were detected by immunohistochemistry 48 hours after treatment. Quantitative image analysis determined a 25% reduction in DNAPK Staining for A10-3-DNAPK-treated samples. Original magnification, x400.
FIGS. 12A-12C illustrate an the design of an aptamer-siRNA chimera.

Aptamer-shRNA Chimera-specific Knockdown of the Target Gene in Human Prostate Tissue To determine whether aptamer-shRNA chimeras would be effective in human tissue, a unique human tissue model was used in which fresh sections of histologically normal human prostate were obtained from radical prostatectomy specimens and immediately maintained ex vivo (Kiviharju-af Hallstrom T M, et al. Human prostate epithelium lacks Wee1 A-mediated DNA damage-induced checkpoint enforcement. *Proc Natl Acad Sci USA*. 2007; 104(17):7211-7216). PSMA expression in these noncancerous tissue sections was confirmed by qRT-PCR prior to treatment. Tissue was then treated with A10-3-DNAPK and control aptamer-shRNA chimeras in the absence of transfection reagents. Quantitative image analysis found DNAPK immunostaining to be decreased by 25% in normal prostate epithelial cells 2 days after treatment with A10-3-DNAPK compared with those treated with control aptamer-shRNA chimeras (FIG. 11). Thus, aptamer-shRNA chimeras are effective in treating human prostate tissues. Further, knockdown in cancer specimens is expected to be much more substantial because PSMA expression is known to be elevated in primary prostate tumors compared to normal prostatic epithelium.

DNA repair pathways are an attractive therapeutic target for radiosensitization. Double stranded breaks (DSBs) are generally regarded as the most lethal of all DNA lesions; if unrepaired, they severely threaten not only the integrity of the genome, but also the survival of the organism (Hoeijmakers J H. Genome maintenance mechanisms for preventing cancer. *Nature*. 2001; 411(6835):366-374; van Gent D C, Hoeijmakers J H, Kanaar R. Chromosomal stability and the DNA double-stranded break connection. *Nat Rev Genet*. 2001; 2(3):196-206; Vilenchik M M, Knudson A G. Endogenous DNA double-strandbreaks: production, fidelity of repair, and induction of cancer. *Proc Natl Acad Sci USA*. 2003; 100(22): 12871-12876). To combat the intricate nature of DSBs, complex repair pathways have evolved. Thus, multiple steps of DSB repair pathways, enzymes, and proteins are targets for RNAi induced radiosensitization therapy. Described herein is the first high-throughput screen of DNA repair pathways by RNAi in combination with radiation therapy. Of 249 mRNAs screened, 10 candidates were identified, 6 of which were identified by at least 2 siRNAs and confirmed in separate PCa cell line models. Given the ubiquity of the identified target genes, these target genes are suitable targets for radiosensitization in a variety of tissue and cancer types.

Since the discovery of RNAi, this pathway has been widely recognized as a new frontier for human therapeutics, and many human clinical trials using this technology are currently planned or in progress. As with other therapeutic approaches, there is a need for selective tissue targeting to minimize damage to normal tissues (Aagaard L, Rossi J J. RNAi therapeutics: principles, prospects and challenges. *Adv Drug Deliv Rev*. 2007; 59(2-3):75-86; Castanotto D, Rossi J J. The promises and pitfalls of RNA-interference-based therapeutics. *Nature*. 2009; 457(7228):426-433; Jinek M, Doudna J A. A three-dimensional view of the molecular machinery of RNA interference. *Nature*. 2009; 457(7228):405-412; Siomi H, Siomi M C. On the road to reading the RNA-interference code, *Nature*. 2009; 457(7228):396-404). PSMA-targeting aptamers were previously developed as a means to selectively deliver therapeutic and imaging agents to PCa cells (Lupold S E, Hicke B J, Lin Y, Coffey D S. Identification and characterization of nuclease-stabilized RNA molecules that bind human prostate cancer cells via the prostate-specific membrane antigen. *Cancer Res*. 2002; 62(14):4029-4033). These aptamers have been used to target therapeutics, including siRNAs and shRNAs (Chu T C, Twu K Y, Ellington A D, Levy M. Aptamer mediated siRNA delivery. *Nucleic Acids Res*. 2006; 34(10):e73; Dassie J P, et al. Systemic administration of optimized aptamer-siRNA chimeras promotes regression of PSMA-expressing tumors. *Nat. Biotechnol*. 2009; 27(9): 839-849; McNamara J O 2nd, et al. Cell type-specific delivery of siRNAs with aptamer-siRNA chimeras. *Nat. Biotechnol*. 2006; 24(8):1005-1015; Wullner U, Neef I, Eller A, Kleines M, Tur M K, Barth S. Cell-specific induction of apoptosis by rationally designed bivalent aptamer-siRNA transcripts silencing eukaryotic elongation factor 2. *Curr Cancer Drug Targets*. 2008; 8(7):554-565).

The present invention relates to aptamer-inhibitory nucleic acid chimeras suitable for use as selective radiosensitizing agents. Described in detail herein is the generation of 2' fluoro-modified pyrimidine aptamer-shRNA chimera radiosensitizing agents. The conjugates retained PSMA targeting ability, and the inhibitory nucleic acid portion of the chimera was effectively processed by RNAi machinery to the predicted antisense siRNA. There was a slight difference in the siRNA product size compared with the reference siRNA, which may be caused by 2'-fluoro-modifications or by cleavage somewhere in the aptamer loop. Similar size differences have been seen in aptamer-siRNA chimera studies (Dassie J P, et al. Systemic administration of optimized aptamer-siRNA chimeras promotes regression of PSMA-expressing tumors. *Nat. Biotechnol*. 2009; 27(9):839-849). The resulting siRNA product was then free to degrade the target transcript at the predicted site, as demonstrated by 5'-RACE. These results demonstrate that aptamer-inhibitory nucleic acid (e.g., shRNA) chimeras can be developed for virtually any target gene, including those that sensitize cancer cells to standard therapeutic approaches.

Advantages of aptamer-inhibitory nucleic acid (e.g., shRNA) chimeras include their simplicity, potential for chemical synthesis, safety, and low toxicity (Behlke M A. Chemical modification of siRNAs for in vivo use. *Oligonucleotides*. 2008; 18(4):305-319; Reynolds A, Leake D, Boese Q, Scaringe S, Marshall W S, Khvorova A. Rational siRNA design for RNA interference. *Nat. Biotechnol*. 2004;

22(3):326-330; Soundararajan S, Chen W, Spicer E K, CourtenayLuck N, Fernandes D J. The nueleolin targeting aptamer AS1411 destabilizes Bcl-2 messenger RNA in human breast cancer cells. *Cancer Res.* 2008; 68(7):2358-2365). The invention described herein demonstrates the utility of such agents in individuals being treated with radiation therapy for localized cancers. Although radiation therapy is highly successful, there are treatment-related risks that would be diminished with a radiation dose-reducing strategy predicated on the claimed aptamer-shRNA chimera method. Moreover, treatment efficacy of local tumors would be improved with radiosensitization while also minimizing side effects.

Also described herein, DNAPK knockdown improved therapeutic efficacy by almost 10-fold. Further, the current A10-3-DNAPK chimeras are suitable for targeting metastatic disease. In addition, inhibition of DNA repair pathways can also sensitize cells to chemotherapeutics, such as alkylating agents and topoisomerase inhibitors, therefore providing a mechanism for systemic chemosensitization (Collis S J, Swartz M J, Nelson W G, DeWeese T L. Enhanced radiation and chemotherapy-mediated cell killing of human cancer cells by small inhibitory RNA silencing of DNA repair factors. *Cancer Res.* 2003; 63(7):1550-1554).

In summary, the claimed aptamer-inhibitory nucleic acid (e.g., shRNA) chimeras retain cancer cell antigen (e.g., PSMA)-selective targeting, proper Dicer shRNA processing, and subsequent target gene knockdown in cancerous cells (e.g., PCa cells, tumor xenografts, and normal human prostatic tissue models). Targeted treatment markedly enhances the benefits of radiation therapy in both cellular and tumor models, demonstrating the utility of these chimeras to enhance radiation therapy for locally advanced cancers.

Example 7

Generation of Aptamer-siRNA Chimeras

Figure 12B:
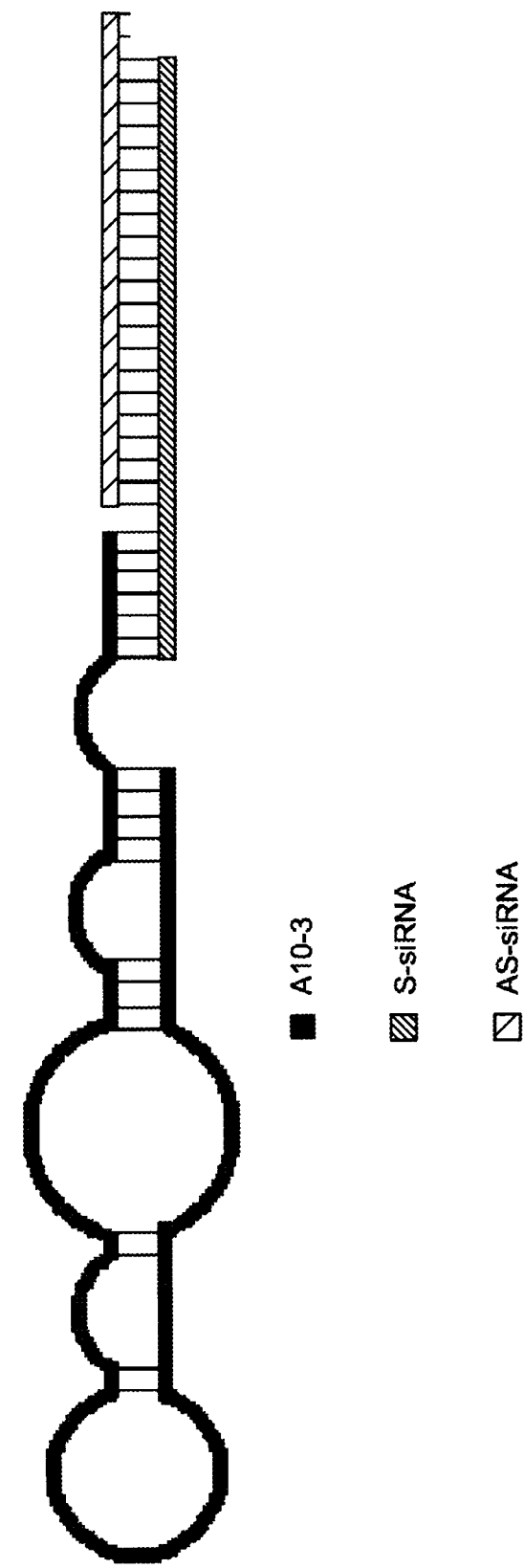
Figure 12C:
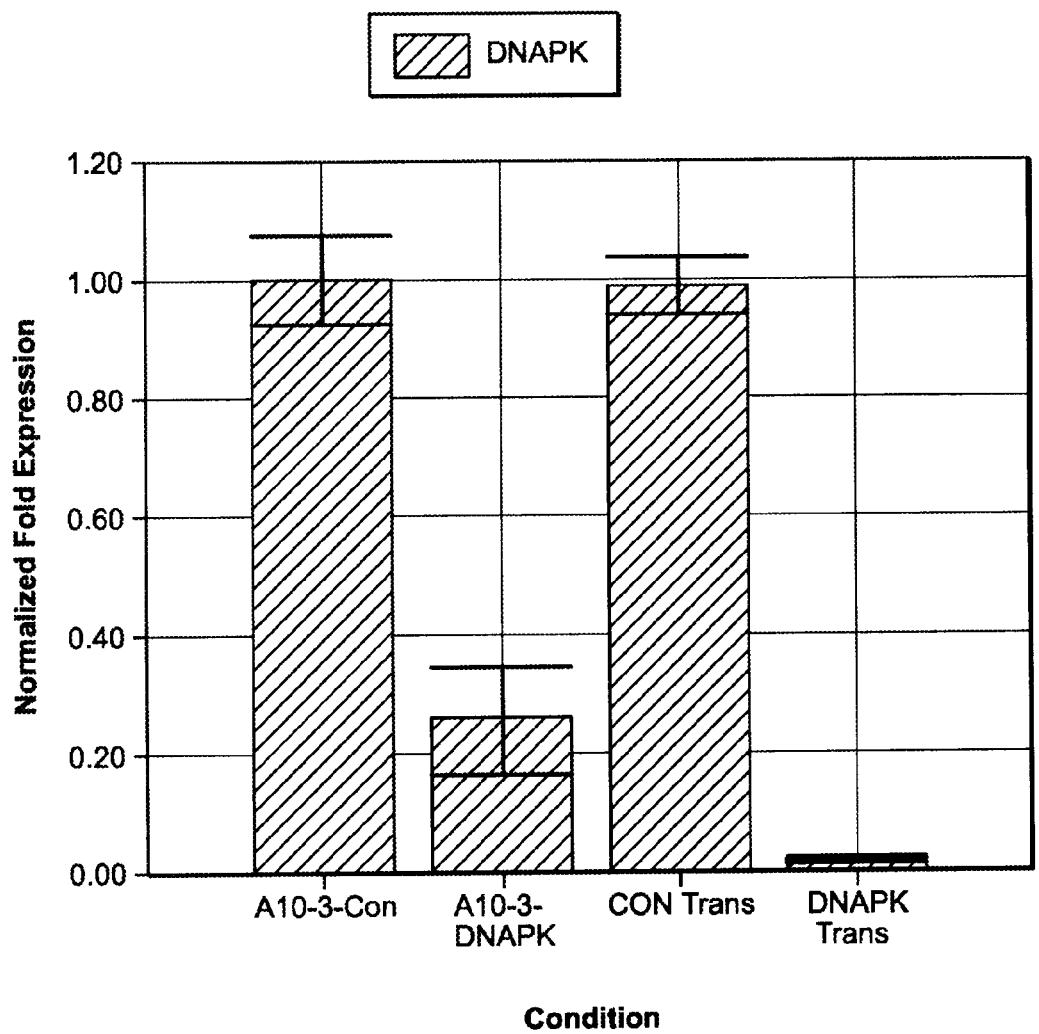

An aptamer-inhibitory nucleic acid chimera was generated that comprises an aptamer that is bonded to an siRNA molecule by Watson-Crick binding. To generate aptamer-siRNA chimeras, three oligonucleotides were synthesized (FIG. 12A) where the first oligonucleotide corresponds to the aptamer, the second oligonucleotide corresponds to the sense strand of the siRNA molecule, and the third strand corresponds to the anti-sense strand of the siRNA. The anti-sense siRNA strand includes a two-nucleotide 3'-overhang. The three oligonucleotides were mixed in a 1:1:1 molar ratio, heated to 90° C. for 5 minutes followed by a 25° C. incubation for 30 minutes. Once formed the aptamer-siRNA chimeras were stored at −20° C. The structure of the annealed aptamer-siRNA is shown in FIG. 12B. LNCaP cells were treated with 400 nM aptamer-siRNA (A10-3-DNAPK) or A10-3 Con as a control. In addition, LNCaP cells were Hyperfect transfected with DNAPK siRNA as an additional control. The levels of DNAPK expression were measured by quantitative reverse transcription coupled to polymerase chain reaction (QT-PCR). As shown in FIG. 12C, the aptamer-siRNA chimera treatment resulted in a significant decrease in DNAPK expression.

The results described above were obtained using the following methods and materials.

Cell Culture.

PCa cell lines DU145 (ATCC no. HTB-81), LNCaP (ATCC no. CRL1740), PC3 (ATCC no. CRL-1435), PC3-PIP, and PC3-Flu (gift of W. Heston, Lerner Research Institute, Cleveland, Ohio, USA) were grown in RPMI 1640 supplemented with 10% FBS and maintained at 37° C. and 5% CO2.

DNA Repair siRNA Library Screen.

A custom siRNA library included 496 siRNAs targeting 249 genes and controls (Qiagen). $2 \times 10^3$ DU145 were Hiperfect reverse transfected (Qiagen) in triplicate in 96-well plates formatted with 5 nM siRNA. 72 hours later, cells were irradiated (6 Gy in a Gammacell 40 [Nordion] 137Cs radiator at approximately 0.6 Gy/min) and grown for 72 hours. Cell viability was quantified by 3-(4,5-dimethylthiazol-2-yl)-5-(3-carboxymethoxyphenyl)-2-(4-sulfophenyl)-2H-tetrazolium (MTS; Promega). Irradiated and nonirradiated viability was normalized to the control siRNA for each siRNA, and radiosensitization was determined as the ratio of increased cell death relative to the control siRNA. Significance was assigned as P<0.05 by Student's t test. Candidate sensitizing siRNAs were confirmed by repeat assays and clonogenic survival assays.

Clonogenic Survival Assays.

Clonogenic survival assays were confirmed in a larger format, in which $1.7 \times 10^5$ DU145 cells were reverse transfected with 5 nM control and candidate siRNAs and grown for 72 hours, after which cell dilutions were plated into 100-mm culture dishes and irradiated immediately. Exposures were carried out as described above. The cells were grown for 14 days and stained with crystal violet; colonies with greater than 30 cells were scored, and survival fraction was calculated.

qRT-PCR.

mRNA (1 µg) from PCa cells treated with the various siRNAs or aptamer-shRNA chimeras was reverse transcribed using QuantiTect Reverse Transcription Kit (Qiagen). Sybrgreen-based real-time qRT-PCR was performed using SYBR GreenER qPCR SuperMix (Invitrogen) according to the manufacturer's instructions. All reactions were done in triplicate. Standard curves were generated by serial dilution of each sample, and the relative amount of target gene mRNA was normalized to GAPDH mRNA (see Table 2 for primers).

TABLE 2

(TABLE 2 discloses SEQ ID NOS 12-27, respectively, in order of appearance)
Primers for q-PCR

| Name | Forward | Reverse |
|---|---|---|
| DNA-PK | AGAAGGCGGCTTACCTGAGT | GACATTTTTGTCAGCCAATCTTT |
| BRCA2 | GCGCGGTTTTTGTCAGCTTA | TGGTCCTAAATCTGCTTTGTTGC |
| ATM | TGGATCCAGCTATTTGGTTTGA | CCAAGTATGTAACCAACAATAGAAGAAGTAG |
| MAD2L2 | CGAGTTCCTGGAGGTGGCTGTGCATC | CTTGACGCAGTGCAGCGTGTCCTGGATA |
| RAD23B | ATGGTAGACAAAACTATAATCCAGCATC | GCCACATCTCCCAACCCA |

TABLE 2-continued (TABLE 2 discloses SEQ ID NOS 12-27, respectively, in order of appearance)
Primers for q-PCR

| Name | Forward | Reverse |
|---|---|---|
| NBN | ATGGAGGCCATATTTCCATGAC | CAAGCAGCCAGAACTTGGAAG |
| RAD54L | CGAAGCCGTAGCAGTGACAAAG | ATGGACATCGTGCCATCCAG |
| GAPDH | TCGCTCTCTGCTCCTCCTGTTC | CGCCCAATACGACCAAATCC |

Aptamer-shRNA Chimeras.

Aptamer-shRNA chimeras were generated as follows. 15 PSMA-targeting (A10-3) or nontargeting (Neg) template primers (Table 3) were fused to a corresponding shRNA by PCR with Pfu polymerase (NEB).

TABLE 3

(TABLE 3 discloses the "Forward" primers as SEQ ID NOS 28, 33, 37 and 40, respectively, in order of appearance and the "Reverse" primers as SEQ ID NOS 29-32, 34-36, 38-39 and 41-42, respectively, in order of appearance)
Primers and templates for aptamer-shRNAs synthesis

| Name | Forward | Reverse | Name |
|---|---|---|---|
| | | 1$^{st}$ PCR primers | |
| A10-3 Temlate primer | TAATACGACTCACTATAGGGAGGACG ATGCGGATCA GCCATGTTTACGTCACTCCTTGTCAA TCCTCATCGGC | AATTCTCCGAACGTGTCACGTCAAGCTTCATACGTGA CACGTTCGGAGAATTGCCGATGAGCATTGACAAG TTCGGCTAACTCGCCAGTTTACAAGCTTCATTAAACT GGCGAGTTAGCCGAAGCCGATGAGGATTGACAAG CAGGACACAATTACAACTAAACAAGCTTCATTTTAGT TGTAATTGTGTCCTGGCCGATGAGGATTGACAAG AGGCTATTCAGTGTGCGAGACAAGCTTCATTCTCGC ACACTGAATAGCCTTGCCGATGAGGATTGACAAG | Con-S1RNA- loop primer DNA-PK-loop primer BRCA2-loop primer ATM-loop primer |
| Neg Temlate primer | TAATACGACTCACTATACAGGCATGC CTAGCTAAGCA GCCCATGGCTTATGCGCGGAATATTG GCTTCCGTTC | TTCGGCTAACTCGCCAGTTTACAAGCTTCATTAAACT GGCGAGTTAGCCGAAGAACGGAAGCCAATATTCC CAGGACACAATTACAACTAAACAAGCTTCATTTTAGT TGTAATTGTGTTCCTGGAACGGAAGCCAATATTCC AAGGCTATTCAGTGTGCGAGACAAGCTTCATTCTCG CACACTGAATAGCCTTGAACGGAAGCCAATATTCC | Neg-DNA-PK- loop primer Neg-BRCA2- loop primer Neg-ATM- loop primer |
| | | 2$^{nd}$ PCR primers | |
| A10-3 5'- primer | TAATACGACTCACTATAGGGAGGAC GATGCGG | AATTCTCCGAACGTGTCACGTCAAGC TTCGGCTAACTCGCCAGTTTACAAGC | Con-loop 2$^{nd}$ primer DNA-PK-loop 2$^{nd}$ primer |
| Neg 5'- primer | TAATACGACTCACTATACAGGCATG CCTAGCT | CAGGACACAATTACAACTAAACAAGC AAGGCTATTCAGTGTGCGAGACAAGC | BRCA2-loop 2$^{nd}$ primer ATM-loop 2$^{nd}$ primer |

These first DNA templates were column purified (Qiagen) and separately used as templates for secondary PCR with A10-3 or Neg 5'-primer and the appropriate second primer for each gene by Taq polymerase (Qiagen). After column purification, products were TA cloned (Promega) and sequenced. PCR products from plasmid or the secondary PCR were used as templates for DuraScribe T7 transcription according to the manufacturer's instructions (Epicenter Biotechnologies). Aptamer-shRNA chimeras (Table 4) were purified by gel electrophoresis (Lupold S E, Hicke B J, Lin Y, Coffey D S.

TABLE 4

(TABLE 4 discloses SEQ ID NOS 43-49, respectively, in order of appearance)
Aptamer-shRNA

| Name | |
|---|---|
| A10-3-Con | GGGAGGACGAUGCGGAUCAGCCAUGUUUACGUCACUCCUUGUCAAUCCUCAUCG GCAAUUCUCCGAACGUGUCACGUAUGAAGCUUGACGUGACACGUUCGGAGAAUU |

TABLE 4-continued (TABLE 4 discloses SEQ ID NOS 43-49, respectively, in order of appearance)

Aptamer-shRNA

| Name | |
|---|---|
| A10-3-DNA-PK | GGGAGGACGAUGCGGAUCAGCCAUGUUUACGUCACUCCUUGUCAAUCCUCAUCG GCUUCGGCUAACUCGCCAGUUUAAUGAAGCUUGUAAACUGGCGAGUUAGCCGAA |
| A10-3-BRCA2 | GGGAGGACGAUGCGGAUCAGCCAUGUUUACGUCACUCCUUGUCAAUCCUCAUCG GCCAGGACACAAUUACAACUAAAAUGAAGCUUGUUUAGUUGUAAUUGUGUCCUG |
| A10-3-ATM | GGGAGGACGAUGCGGAUCAGCCAUGUUUACGUCACUCCUUGUCAAUCCUCAUCG GCAAGGCUAUUCAGUGUGCGAGAAUGAAGCUUGUCUCGCACACUGAAUAGCCUU |
| Neg-DNA-PK | CAGGCAUGCCUAGCUAAGCAGCCCAUGGCUUAUGCGCGGAAUAUUGGCUUCCGU UCUUCGGCUAACUCGCCAGUUUAAUGAAGCUUGUAAACUGGCGAGUUAGCCGAA |
| Neg-BRCA2 | CAGGCAUGCCUAGCUAAGCAGCCCAUGGCUUAUGCGCGGAAUAUUGGCUUCCGU UCCAGGACACAAUUACAACUAAAAUGAAGCUUGUUUAGUUGUAAUUGUGUCCUG |
| Neg-ATM | CAGGCAUGCCUAGCUAAGCAGCCCAUGGCUUAUGCGCGGAAUAUUGGCUUCCGU UCAAGGCUAUUCAGUGUGCGAGAAUGAAGCUUGUCUCGCACACUGAAUAGCCUU |

Identification and characterization of nuclease-stabilized RNA molecules that bind human prostate cancer cells via the prostate-specific membrane antigen. Cancer Res. 2002; 62(14):4029-4033).

Aptamer-shRNA Chimera-Mediated Gene Silencing and Radiosensitization Assay.

$2\times10^5$ cells (LNCaP, PC3-PIP, or PC3-Flu) were Hiperfect transfected with 100 nM siRNA (Table 5) in 6-well plates or treated with 4, 40, or 400 nM of aptamer-shRNA chimeras.

TABLE 5

(TABLE 5 discloses SEQ ID NOS 50-57, respectively, in order of appearance)

siRNA

| Name | sense | anti-sense |
|---|---|---|
| DNA-PK | UUCGGCUAACUCGCC AGUUUA | UAAACUGGCGAGUUA GCCGAA |
| BRCA2 | CAGGACACAAUUACA ACUAAA | UUUAGUUGUAAUUGU GUCCUG |
| ATM | AAGGCUAUUCAGUGU GCGAGA | UCUCGCACACUGAAU AGCCUU |
| Con siRNA | AAUUCUCCGAACGUG UCACGU | ACGUGACACGUUCGG AGAAUU |

After 48 hours, cells were either collected for qRT-PCR or seeded in 96-well plates at 2,000 cells/well. 24 hours later, cells were irradiated with 6 Gy using a Gammacell 40 (Nordion) 137Cs radiator at approximately 0.6 Gy/min. Cell viability was assessed after 12 days by MTS.

Dicer Processing Analysis

For in vitro Dicer assay, 1 μg of each aptamer-shRNA chimera was incubated with recombinant human Dicer following the manufacturer's recommendations (Recombinant Human Turbo Dicer Kit; GTS). For cellular Dicer assay, RNA from aptamer-shRNA chimera-treated LNCaP cells (as described above) were evaluated by Northern blot. Probes were as follows: DNAPK siRNA antisense, 5'-TTCG-GCTAACTCGCCAGTTTA-3' (SEQ ID NO: 58); control siRNA antisense, 5'-AATTCTCCGAACGTGTCACGT-3' (SEQ ID NO: 59).

5' RACE mRNA (5 μg) from LNCaP cells or LNCaP tumor treated with aptamer-shRNA chimeras was ligated to GeneRacer adaptor (Invitrogen). Ligated RNA was reverse transcribed using a gene-specific primer (GSP[DNAPK] reverse 1, 5'-GAGGGCTCCTTGACAAACACATCCAT-3' (SEQ ID NO: 60)). To detect cleavage products, PCR was performed using primers complementary to the RNA adaptor (GR 5' primer, 5'-CTCTAGAGCGACTGGAGCACGAG-GACACTA-3' (SEQ ID NO: 61)) and gene-specific primer (GSP[DNAPK] reverse 2, 5'-GGAAGGCCCGGAGT-GCGTGTACCAT-3' (SEQ ID NO: 62)). Amplification products were resolved by agarose gel electrophoresis, visualized by ethidium bromide staining, and confirmed by sequencing.

Animal Model Studies.

Studies were performed according to the protocols approved by the Animal Care and Use Committee at Johns Hopkins University. 8-week-old athymic nude mice (nu/nu; Harlan Laboratories Inc.) were obtained from the Animal Center Isolation Facility at Johns Hopkins University and maintained in a sterile environment according to guidelines established by the Association for Assessment and Accreditation of Laboratory Animal Care. Mice were inoculated with $5\times10^6$ (50% Matrigel) PC3 cells or LNCaP cells subcutaneously, and tumors were grown to at least 0.8 cm in diameter. For aptamer-shRNA chimera knockdown, tumors were injected with 200 pmol chimeras on days −3 and −2. On day 0, the tumor was harvested and partitioned for RNA extraction or formalin fixation. For radiosensitization, LNCaP or PC3 tumors were randomized into no-radiation and radiation groups and treated with aptamer-shRNA chimeras as above. On day 0, radiation groups received 6 Gy local IR (5.8 Gy/min) to the tumor-bearing leg from a J.L. Shepherd Mark 137Cs irradiator with the remainder of the body shielded from the source. Tumors were measured every 2 days to calculate tumor volume: (w×l×h)×0.52. Tumor response was determined as reaching 4 times its volume at the start of radiation treatment.

Immunohistochemistry.

Paraffin-embedded sections (4 μm) were taken from xenograft tumors or human tissues. Slides were deparaffinized and rehydrated through a series of ethanol gradients, then treated with 0.1% Tween 20 detergent in deionized water and incubated in Target Retrieval solution (Dako) and in steam (Black and Decker Vegetable Steamer), then washed in PBS with Tween. After 3% hydrogen peroxide incubation, primary antibody anti-DNAPK (Ab-2, mouse mAb; Calbiochem) was added to each slide, A second antibody, Powervision (Poly-HRP anti-mouse IgG; Leica Biosystems) was applied to the specimens according to the manufacturer's standard protocol. The staining was developed with diaminobenzidine (DAB kit; Vector Laboratories) and counterstained with Mayer hematoxylin. Images were captured for presentation using a Nikon 50i microscopy with Nikon NIS-Elements software and an attached charge-coupled device digital camera. Brightfield setting was the same for all images. For quantification of DNAPK, whole DAB staining slides were scanned via ScanScope CS system (Aperio Technologies Inc.) at the Tissue Micro Array Core of Johns Hopkins University School of Medicine, and total DNAPK expression per cell nucleus was measured from 5-8 areas of tissue specimen for 500-1,000 cells using Framework for Image Dataset Analysis (FrIDA) software as previously described (Gurel B, et al. Nuclear MYC protein overexpression is an early alteration in human prostate carcinogenesis. *Mod Pathol.* 2008; 21(9):1156-1167).

Ex Vivo Human Prostate Tissue Model.

Fresh human prostate tissue samples were obtained from the Department of Pathology of Johns Hopkins University. This study was approved by the Institutional Review Board at Johns Hopkins Medical Institution (approval no. NA_00015481), and informed consent was obtained from patients participating in the study. Fresh tissue representing histologically normal areas was bored from radical prostatectomy specimens and sliced at 300 µm with a Krumdieck precision tissue slicer (Alabama Research and Development Corp.; Kiviharju-af Hallstrom T M, et al. Human prostate epithelium lacks Weel A-mediated DNA damage-induced checkpoint enforcement, *Proc Natl Aced Sci USA.* 2007; 104 (17):7211-7216). The tissue slices were loaded onto titanium grids in 6-well plates containing culture medium with 200 nM aptamer-shRNA chimeras and rotated on an inclined plane in a humidified tissue culture incubator at 37° C. for 48 hours before being processed for immunohistochemical staining and quantification as above.

Statistics.

Statistical analysis data of tumor size was evaluated by 2-way ANOVA. A P value of 0.05 or less was considered significant. For the extension of tumor quadrupling experiments, events (animals whose tumor volume was not yet 4-fold the size at injection) were plotted on Kaplan-Meier curve and analyzed by log-rank (Mantel-Cox) test. Paired samples were evaluated by 2-tailed Student's t test.

Materials.

Unless otherwise noted, all DNA primers were purchased from Sigma-Aldrich, siRNAs were purchased from IDT and all cell culture products were purchased from Gibco BRL/LifeTechnologies.

Interferon Assay.

For evaluating the interferon β response, $2 \times 10^5$ LNCaP cells were either transfected with siRNA DNA-PK or incubated with 400 nM A10-3-Con, A10-3-DNA-PK or NegDNA-PK, Poly(I:C) (invivogen) as a positive control, for 48 hours before the secretion of interferon β into the cell culture supernatant was analyzed. Detection of interferon β was accomplished by using a commercially available sandwich interferon β ELISA kit (PBL) following the manufacturer's recommendations. The results obtained were compared to serial dilutions of an interferon β positive control provided with the kit.

RNA Secondary Structure.

M-fold was used to predict the structures of Aptamer-shRNAs. The most stable structures with the lowest energies for each RNA oligo were compared.

PSMA Cell-Surface Expression.

PSMA cell-surface expression was determined by flow cytometry using antibodies specific to human PSMA (J591 from Neil Bander, Weill Medical College of Cornell University). PC3—PIP or PC3-Flu cells were trypsinized and washed three times in PBS. $1 \times 10^6$ cells were resuspended in 100 µl cell sorting buffer (1×PBS, 0.5% bovine serum albumin (BSA), 2 mmol/L EDTA) with a 1:5000 dilution of Human PSMA antibody J591 and incubated at 4° C. for 20 min. Cells were then washed in 1 ml cold cell sorting buffer and incubated at 4° C. for 20 min with a 1:1,000 dilution of Alexa Fluor 488 F(ab')2 fragment of antihuman IgG (A11013; Invitrogen) in cell sorting buffer. Cells were washed and incubated at 4° C. for 20 min with 4% PFA (1 ml). After fixation, cells were then resuspended in cell sorting buffer and analyzed by flow cytometry (Becton Dickson Calibur FACS Analytic cytometer).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Incorporation by Reference

All patents, publications, and nucleotide accession numbers mentioned in this specification are herein incorporated by reference to the same extent as if each independent patent, publication, and accession number record was specifically and individually indicated to be incorporated by reference.

What is claimed is:

1. A method of inducing cell death or terminal differentiation in a neoplastic cell, the method comprising:
   a) contacting the neoplastic cell with an effective amount of an aptamer-inhibitory nucleic acid chimera, wherein the aptamer-inhibitory nucleic acid chimera comprises a 2'fluoro-modified pyrimidine RNA aptamer-shRNA chimera, wherein the aptamer-shRNA chimera specifically binds prostate-specific membrane antigen (PSMA), and wherein the shRNA decreases the expression of DNA-activated protein kinase (DNAPK); and
   b) exposing the neoplastic cell to ionizing radiation, thereby inducing cell death or terminal differentiation in the neoplastic cell.

2. A method of reducing the growth, proliferation or survival of a neoplastic cell, the method comprising:
   a) contacting the neoplastic cell with an effective amount of an aptamer-inhibitory nucleic acid chimera, wherein the aptamer-inhibitory nucleic acid chimera comprises a 2'fluoro-modified pyrimidine RNA aptamer-shRNA chimera, wherein the aptamer-shRNA chimera specifically binds prostate-specific membrane antigen (PSMA), and wherein the shRNA decreases the expression of DNA-activated protein kinase (DNAPK); and
   b) exposing the neoplastic cell to ionizing radiation, thereby reducing growth, proliferation or survival of the neoplastic cell.

3. A method of treating neoplasia in a subject comprising:
   a) administering an aptamer-inhibitory nucleic acid chimera to the subject, wherein the aptamer-inhibitory nucleic acid chimera comprises a 2'fluoro-modified pyrimidine RNA aptamer-shRNA chimera, wherein the aptamer-shRNA chimera specifically binds prostate-specific membrane antigen (PSMA), and wherein the shRNA decreases the expression of DNA-activated protein kinase (DNAPK); and
   b) exposing the neoplasia to ionizing radiation, thereby treating neoplasia in the subject.

4. A method of treating prostate cancer in a subject in need thereof comprising:
   a) administering an aptamer-shRNA chimera to the subject, wherein the aptamer-shRNA chimera comprises a 2'fluoro-modified pyrimidine RNA aptamer-shRNA chimera, wherein the aptamer-shRNA chimera specifically binds prostate-specific membrane antigen (PSMA), and wherein the shRNA decreases the expression of DNA-activated protein kinase (DNAPK); and
   b) exposing the subject to ionizing radiation, thereby treating prostate cancer in the subject.

5. The method of claim 4, wherein the aptamer-shRNA chimera comprises an A10-3 aptamer, wherein the A10-3 aptamer comprises SEQ ID NO: 11 or SEQ ID NO: 63.

6. The method of claim 4, wherein the aptamer-shRNA chimera comprises A10-3 aptamer-DNAPK shRNA, wherein said A10-3 aptamer-DNAPK shRNA comprises SEQ ID NO: 44.

7. The method of claim 4, wherein the DNAPK shRNA comprises SEQ ID NO: 50, SEQ ID NO: 51, SEQ ID NO: 64, or SEQ ID NO: 65.

8. The method of claim 1, wherein the aptamer-shRNA chimera comprises an A10-3 aptamer, wherein the A10-3 aptamer comprises SEQ ID NO: 11 or SEQ ID NO: 63.

9. The method of claim 1, wherein the shRNA comprises SEQ ID NO: 50, SEQ ID NO: 51, SEQ ID NO: 64, or SEQ ID NO: 65.

10. The method of claim 1, wherein the aptamer-shRNA chimera comprises A10-3 aptamer-DNAPK shRNA, wherein said A10-3 aptamer-DNAPK shRNA comprises SEQ ID NO: 44.

* * * * *